(12) United States Patent
Takahashi et al.

(10) Patent No.: US 6,569,899 B1
(45) Date of Patent: May 27, 2003

(54) 4-AMINOBUTANOIC ACID DERIVATIVES AND DRUGS CONTAINING THESE DERIVATIVES AS THE ACTIVE INGREDIENT

(75) Inventors: Kanji Takahashi, Osaka (JP); Tsuneyuki Sugiura, Osaka (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/958,093

(22) PCT Filed: Apr. 5, 2000

(86) PCT No.: PCT/JP00/02191

§ 371 (c)(1), (2), (4) Date: Oct. 5, 2001

(87) PCT Pub. No.: WO00/59865

PCT Pub. Date: Oct. 12, 2000

(30) Foreign Application Priority Data

Apr. 6, 1999 (JP) .......................................... 11-098453

(51) Int. Cl.$^7$ ...................... A61K 31/166; C07C 233/00

(52) U.S. Cl. ...................... 514/522; 564/155; 562/465; 558/415; 558/169; 558/170; 560/170; 560/173; 514/140; 514/506; 514/616

(58) Field of Search ................................ 558/415, 169, 558/170; 564/155; 514/506, 522, 616, 140; 562/465; 560/170, 173

(56) References Cited

PUBLICATIONS

Renil, Manet et al, "PEGA supports for combinatorial peptide synthesis and solid–phase enzymic library assays," J. Pept. Sci., 1998, vol. 4, No. 3, pp. 195–210.

Luo, Jin et al, "Efficient Syntheses of Pyrofolic Acid and Pteroyl Azide, Reagents for the Production of Carboxyl–Differentiated Derivatives of Folic Acid", J. Am. Chem. Sco., 1997, vol. 119, No. 42, pp. 10004–10013.

*Primary Examiner*—Joseph K. McKane
*Assistant Examiner*—Golam M. M. Shameem
(74) *Attorney, Agent, or Firm*—Stevens, Davis, Miller & Mosher, L.L.P.

(57) ABSTRACT

Aminobutylic acid derivatives of the formula (I)

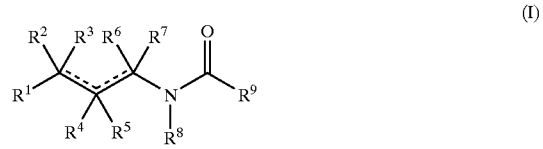

wherein the symbols are as defined in specification; and non-toxic salts thereof. Because of inhibiting matrix metalloproteinase, the compounds of the formula (I) are useful for prevention and/or treatment of diseases, for example, rheumatoid diseases, arthrosteitis, osteoarthritis, unusual bone resorption, osteoporosis, periodontitis, interstitial nephritis, arteriosclerosis, pulmonary emphysema, cirrhosis, cornea injury, cornea ulcer, metastasis, invasion or growth of tumor cells, autoimmune disease, disease caused by vascular emigration or infiltration of leukocytes, arterialization, multiple sclerosis, arota aneurysm, endometriosis, restenosis after PTCA, unstable angina, acute myocardial infarction, transient ischemic attack.

9 Claims, No Drawings

4-AMINOBUTANOIC ACID DERIVATIVES AND DRUGS CONTAINING THESE DERIVATIVES AS THE ACTIVE INGREDIENT

CROSS-REFERENCE TO RELATED APPLICATIONS

This application is a 371 application of International Application No. PCT/JP00/02191, filed Apr. 5, 2000, claiming the benefit of Japanese Patent Application No.11-98453, filed Apr. 6, 1999, the entire disclosures of which are incorporated herein by reference.

TECHNICAL FIELD

This invention relates to aminobutyric acid derivatives, processes for the preparation thereof and pharmaceutical agents comprising aminobutyric acid derivatives as active ingredient.

More particularly, this invention relates to:
[1] aminobutyric acid derivatives of the formula (I):

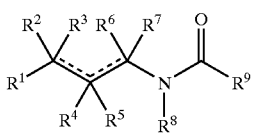

(I)

wherein all the symbols are as hereinafter defined, and non-toxic salts thereof, processes for the preparation thereof and pharmaceutical agents comprising aminobutyric acid derivatives as active ingredient, and

[2] a compound which is selected from
(1) 5-ethoxymethoxy-4(S)-[N-(4-iodophenylcarbonyl)amino]pentanoic acid,
(2) 5-ethoxymethoxy-4(S)-[N-(4-cyanophenylcarbonyl)amino]-2(R)-methoxymethylpentanoic acid,
(3) 2(R)-ethoxymethyl-5-ethoxymethoxy-4 (S)-[N-(4-nitrophenylcarbonyl)amino]pentanoic acid,
(4) 5-ethoxymethoxy-2 (S)-(3-thienylmethyl)-4(S)-[N-(4-nitrophenylcarbonyl)amino]pentanoic acid,
(5) 5-ethoxymethoxy-2(S)-(3-furylmethyl)-4(S)-[N-(4-nitrophenylcarbonyl)amino]pentanoic acid,
(6) 2(S)-benzyl-5-pivaroyloxy-4(S)-[N-(4-nitrophenylcarbonyl)amino]pentanoic acid,
(7) 5-acetyloxy-2(S)-benzyl-4(S)-[N-(4-nitrophenylcarbonyl)amino]pentanoic acid,
(8) 5-ethoxymethoxy-2(R)-methoxymethyl-4(S)-[N-(4-phenoxyhenylcarbonyl)amino]pentanoic acid,
(9) 5-ethoxymethoxy-2(R)-methoxymethyl-4(S)-[N-(4-(2-furyl)phenylcarbonyl)amino]pentanoic acid,
(10) 5-ethoxymethoxy-4(S)-[N-(4-cyanophenylcarbonyl)amino]-2(R)-ethoxymethylpentanoic acid,
(11) 5-ethoxymethoxy-2(S)-methoxymethyl-4(R)-[N-(4-nitrophenylcarbonyl)amino]pentanoic acid,
(12) 5-ethoxymethoxy-2(S)-methoxymethyl-4(R)-[N-(4-chlorophenylcarbonyl)amino]pentanoic acid,
(13) 5-ethoxymethoxy-2(S)-methoxymethyl-4(R)-[N-(4-bromophenylcarbonyl)amino]pentanoic acid,
(14) 5-ethoxymethoxy-2(S)-methoxymethyl-4(R)-[N-(4-cyanophenylcarbonyl)amino]pentanoic acid,
(15) 5-ethoxymethoxy-2(S)-benzyl-4(S)-[N-(4-chlorocyclohexylcarbonyl)amino]pentanoic acid,
(16) 5-ethoxymethoxy-4(S)-[N-(4-nitrophenylcarbonyl)amino]pentanoic acid,
(17) 5-methoxyethoxymethoxy-2(S)-methyl-4(S)-[N-methyl-N-(4-nitrophenylcarbonyl)amino]pentanoic acid,
(18) trans-2-[(4-nitrophenylcarbonyl)aminomethyl]cyclohexanoic acid,
(19) trans-2-[(4-(3-methoxy-1-propynyl)phenylcarbonyl)aminomethyl]cyclohexanoic acid,
(20) trans-2-[(4-nitrophenylcarbonyl)amino]cyclohexylacetic acid,
(21) N-hydroxy-5-ethoxymethoxy-2(R)-methoxymethyl-4(S)-[N-(4-cyanophenylcarbonyl)amino]pentanamide,
(22) N-hydroxy-2(R)-ethoxymethyl-5-ethoxymethoxy-4(S)-[N-(4-nitrophenylcarbonyl)amino]pentanamide,
(23) N-hydroxy-5-ethoxymethoxy-2(S)-(3-thienylmethyl)-4(S)-[N-(4-nitrophenylcarbonyl)amino]pentanamide,
(24) N-hydroxy-5-ethoxymethoxy-2(S)-(3-furylmethyl)-4(S)-[N-(4-nitrophenylcarbonyl)amino]pentanamide,
(25) N-hydroxy-2(S)-benzyl-5-pivaroyloxy-4(S)-[N-(4-nitrophenylcarbonyl)amino]pentanamide,
(26) N-hydroxy-5-acetyloxy-2(S)-benzyl-4(S)-[N-(4-nitrophenylcarbonyl)amino]pentanamide,
(27) N-hydroxy-5-ethoxymethoxy-2(R)-methoxymethyl-4(S)-[N-(4-phenoxyphenylcarbonyl)amino]pentanamide,
(28) N-hydroxy-5-ethoxymethoxy-2(R)-methoxymethyl-4(S)-[N-(4-(2-furyl)phenylcarbonyl)amino]pentanamide,
(29) N-hydroxy-5-ethoxymethoxy-2(R)-ethoxymethyl-4(S)-[N-(4-cyanophenylcarbonyl)amino]pentanamide,
(30) N-hydroxy-5-ethoxymethoxy-2(S)-methoxymethyl-4(R)-[N-(4-nitrophenylcarbonyl)amino]pentanamide,
(31) N-hydroxy-5-ethoxymethoxy-2(S)-methoxymethyl-4(R)-[N-(4-chlorophenylcarbonyl)amino]pentanamide,
(32) N-hydroxy-5-ethoxymethoxy-2(S)-methoxymethyl-4(R)-[N-(4-bromophenylcarbonyl)amino]pentanamide,
(33) N-hydroxy-5-ethoxymethoxy-2(S)-methoxymethyl-4(R)-[N-(4-cyanophenylcarbonyl)amino]pentanamide,
(34) N-hydroxy-5-ethoxymethoxy-2(S)-benzyl-4(S)-[N-(4-chlorocyclohexylcarbonyl)amino]pentanamide,
(35) N-hydroxy-5-ethoxymethoxy-4(S)-[N-(4-nitrophenylcarbonyl)amino]pentanamide,
(36) N-hydroxy-2(S)-methyl-5-methoxyethoxymethoxy-4(S)-[N-methyl-N-(4-nitrophenylcarbonyl)amino]pentanamide,
(37) N-hydroxy-5-hydroxy-2(R)-methoxymethyl-4(S)-[N-(4-nitrophenylcarbonyl)amino]pentanamide,
(38) N-hydroxy-5-hydroxy-2(R)-methoxymethyl-4(S)-[N-(4-chlorophenylcarbonyl)amino]pentanamide,
(39) N-hydroxy-2(S)-(2-benzothiophen-3-yl)methyl)-5-hydroxy-4(S)-[N-methyl-N-(4-nitrophenylcarbonyl)amino]pentanamide,
(40) N-hydroxy-2(S)-allyl-5-hydroxy-4(S)-[N-methyl-N-(4-nitrophenylcarbonyl)amino]pentanamide,
(41) N-hydroxy-2(S)-(3-phenylpropyl)-5-hydroxy-4(S)-[N-methyl-N-(4-bromophenylcarbonyl)amino]pentanamide,
(42) N-hydroxy-2(S)-(3-phenylpropyl)-5-hydroxy-4(S)-[N-methyl-N-(4-nitrophenylcarbonyl)amino]pentanamide,
(43) N-hydroxy-2(S)-methyl-5-hydroxy-4(S)-[N-methyl-N-[(5-nitro-2-thienyl)carbonyl]amino]pentanamide,
(44) N-hydroxy-2(S)-benzyl-5-hydroxy-4(S)-[N-methyl-N-[(5-bromo-2-thienyl)carbonyl]amino]pentanamide,
(45) trans-1-(N-hydroxyaminocarbonyl)-2-[(4-nitrophenylcarbonyl)aminomethyl]cyclohexane,
(46) trans-1-(N-hydroxyaminocarbonyl)-2-[(4-(3-methoxy-1-propynyl)phenylcarbonyl)aminomethyl]cyclohexane,
(47) trans-1-(N-hydroxyaminocarbonylmethyl)-2-[(4-nitrophenylcarbonyl)amino]cyclohexane,
and methyl ester, t-butyl ester, benzyl ester, allyl ester, and non-toxic salts thereof, and pharmaceutical agents comprising the compound and non-toxic salts thereof as active ingredient.

BACKGROUND ART

The matrix metalloproteinases (MMPs) are neutral metalloproteinases and zinc ($Zn^{2+}$) is essential in the active site for their activation. They degrade collagen, laminin, proteoglycans, fibronectin, elastin, gelatin etc. under physiological conditions and therefore, are effective on growth and tissue remodeling of articulation tissue, bone tissue and connective tissue. At least 10 classes of MMPs, which differ in primary structure, are identified. Concretely, there are Interstitial Collagenase (MMP-1), Neutrophil Collagenase (MMP-8), Gelatinase A (MMP-2), Gelatinase B (MMP-9), Stromelysin-1 (MMP-3), Stromelysin-2 (MMP-10), Matrilysin (MMP-7), metalloelastase (MMP-12) etc.

As common characteristics of these enzymes, MMPs
(1) have $Zn^{2+}$ in the active site and the activity depends on calcium ion ($Ca^{2+}$)
(2) are secreted as an inactive proenzyme and activated outside of cells,
(3) have high homology on amino acid sequence,
(4) have an ability to degrade on various extracellular matrix components in vivo,
(5) are regulated by tissue inhibitors of metalloproteinases (TIMP) which are specific to MMPs.

MMP inhibitors are useful for prevention and/or treatment of various diseases induced by overexpression and excess activation of MMP. Such diseases are, for example, rheumatoid diseases, arthrosteitis, osteoarthritis, unusual bone resorption, osteoporosis, periodontitis, interstitial nephritis, arteriosclerosis, pulmonary emphysema, cirrhosis, cornea injury, cornea ulcer, metastasis, invasion or growth of tumor cells, autoimmune disease (Crohn's disease, Sjogren's syndrome), disease caused by vascular emigration or infiltration of leukocytes, arterialization, multiple sclerosis, aorta aneurysm, endometriosis, restenosis after PTCA, unstable angina, acute myocardial infarction, transient ischemic attack.

Some compounds possessing inhibitory activity against MMP are known. A sequence in the vicinity of cleavage site of collagen (Gly-Ile-Ala-Gly or Gly-Leu-Ala-Gly) has high affinity for collagenase. Much research and development on substrate analogous MMP inhibitors, which are chemically modified so as to have zinc affinity groups on a cleaving site of the substrate, has energetically been carried out [Inhibitors of matrix metalloproteinases (MMP's), Nigel R A Beeley, Phillip R J Ansell, Andrew J P Docherty et. al., Curr. Opin. Ther. Patents., A, 7–16 (1994), Current Drugs Ltd ISSN 0962–2594]. However, these substrate-analogues inhibitors might have various problems. Therefor, it is desired to obtain a non-peptide inhibitor and some compounds are reported.

For example, in the specification of EP 757037 as the Example, sulfonylamino acid derivatives of the formula (W):

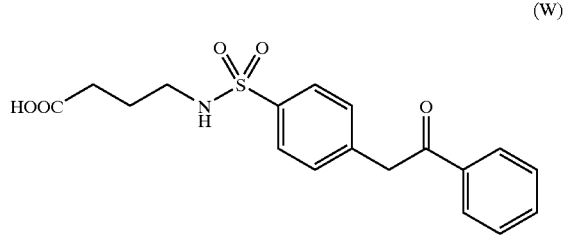

are disclosed to have an activity of inhibiting matrix metalloproteinase.

In the specification of EP 757984 as the Example, hydroxamic acid derivatives of the formula (X):

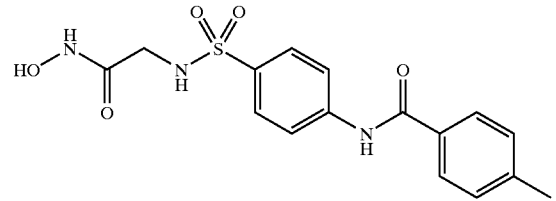

are disclosed to have an activity of inhibiting matrix metalloproteinase.

DISCLOSURE OF THE INVENTION

Energetic investigations have been carried out in order to make an inhibitor for matrix metalloproteinase, e.g. gelatinase, stromelysin or collagenase. The present inventors have found that aminobutyric acid derivatives of the formula (I), which are carboxylic amino derivatives of γ-amino acid accomplished the present purpose.

The present invention relates to:
[1] aminobutyric acid derivatives of the formula (I):

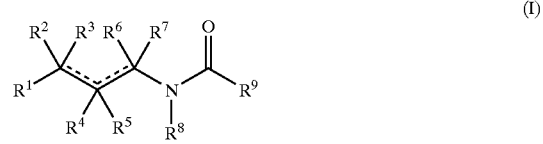

wherein
$R^1$ is —COOR$^{10}$, —CONHOR$^{10}$, —CONHNHR$^{10}$, —(CH$_2$)$_n$SR$^{50}$ or —Y—PO(OR$^{51}$)$_2$;
$R^{10}$ is (i) hydrogen, (ii) C1–8 alkyl, (iii) C2–8 alkenyl, (iv) phenyl, (v) C1–8 alkyl substituted by phenyl or C1–8 alkoxy, or (vi) oxycarbonyl substituted by phenyl, benzyl or C1–8 alkyl;
n is 0–3;
$R^{50}$ is (i) hydrogen, (ii) C1–8 alkyl, (iii) —COR$^{52}$, in which R$^{52}$ is C1–8 alkyl or phenyl, (iv) —SR$^{53}$, in which R$^{53}$ is hydrogen, C1–8 alkyl or phenyl;
$R^{51}$ is hydrogen, C1–8 alkyl or phenyl;
Y is a single bond, —CH$_2$— or —O—;
$R^2$, $R^3$, $R^4$, $R^5$, $R^6$ and $R^7$ each, independently, is
  (1) hydrogen,
  (2) C1–8 alkyl,
  (3) C2–8 alkenyl,
  (4) —OR$^{11}$,
  (5) —SR$^{11}$,
  (6) —NR$^{12}$R$^{13}$,
  (7) Cyc1,
  (8) C1–8 alkyl substituted by one or more groups selected from —OR$^{11}$, —SR$^{11}$, —NR$^{12}$R$^{13}$, —COR$^{14}$, guanidino and Cyc1,
  (9) C2–8 alkenyl substituted by one or more groups selected from —OR$^{11}$, —SR$^{11}$, —NR$^{12}$R$^{13}$, —COR$^{14}$, guanidino and Cyc1,
  (10) C2–8 alkynyl,
  (11) C1–8 alkyl substituted by one or more groups selected from C3–8 alkenyloxy, with the proviso that a group having a double bond at 1-position is excluded; and C3–8 alkynyloxy, with the proviso that a group having a triple bond at 1-position is excluded; or R³ and R⁴, taken together is C1–8 alkylene, R⁵ and R⁶, taken together is C1–8 alkylene, R³ and R⁶, taken together is C1–8 alkylene, R² and R³, taken together is C2–8 alkylene, R⁴ and R⁵, taken together is C2–8 alkylene, or R⁶ and R⁷, taken together is C2–8 alkylene;

in which Cyc1 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atoms, (vii) cyano (viii) hydroxy, (ix) benzyloxy, (x) —NR¹⁰¹R¹⁰², in which R¹⁰¹ and R¹⁰² each, independently, is hydrogen or C1–8 alkyl, (xi) —COOR¹⁰³, in which R¹⁰³ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR¹⁰⁴R¹⁰⁵, in which R¹⁰⁴ and R¹⁰⁵ each, independently, is hydrogen, C1–8 alkyl or phenyl;

R¹¹ is
(i) hydrogen,
(ii) C1–8 alkyl,
(iii) Cyc1,
(iv) —COR¹⁸,
(v) C1–8 alkyl substituted by one or more groups selected from —OR¹⁵, —SR¹⁵, —NR¹⁶R¹⁷, —COR¹⁸, guanidino and Cyc1;

R¹⁵ is hydrogen, C1–8 alkyl, Cyc1 or C1–8 alkyl substituted by Cyc1 or C1–8 alkoxy;

R¹⁶ is hydrogen or C1–8 alkyl;

R¹⁷ is hydrogen, C1–8 alkyl or —COR¹⁹, in which R¹⁹ is C1–8 alkyl, Cyc1, C1–8 alkyl substituted by Cyc1;

R¹⁸ is hydroxy, C1–8 alkyl, C1–8 alkoxy or —N²⁰R²¹, in which R²⁰ and R²¹, each independently, is hydrogen, C1–8 alkyl, Cyc1 or C1–8 alkyl substituted by Cyc1;

R¹² is hydrogen, C1–8 alkyl, Cyc1 or C1–8 alkyl substituted by Cyc1;

R¹³ is hydrogen, C1–8 alkyl, Cyc1, C1–8 alkyl substituted by Cyc1, or —COR²², in which R²² is C1–8 alkyl, Cyc1 or C1–8 alkyl substituted by Cyc1;

R¹⁴ is hydroxy, C1–8 alkyl, C1–8 alkoxy, Cyc1, C1–8 alkyl substituted by Cyc1, or —NR²³R²⁴, in which R²³ and R²⁴, each ndependently, is (i) hydrogen, (ii) C1–8 alkyl, (iii) Cyc1 or (iv) C1–8 alkyl substituted by Cyc1 or hydroxy;

(1) when R⁸ is
1) hydrogen,
2) C1–8 alkyl,
3) C1–8 alkoxycarbonyl,
4) C1–8 alkyl substituted by one or more groups selected from —OR²⁶, —SR²⁶, —NR²⁷R²⁸ and —COR²⁹, or
5) C1–8 alkoxycarbonyl substituted by Cyc2, R⁹ is

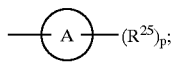

(2) when R⁸ is

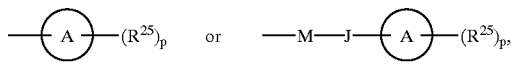

R⁹ is
1) C1–8 alkyl,
2) C1–8 alkoxy,
3) C1–8 alkoxy substituted by Cyc2,
4) C1–8 alkyl substituted by one or more groups selected from —OR²⁶, —SR²⁶, —NR²⁷R²⁸, —COR²⁹ and Cyc2, or
5)

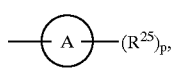

in which Cyc2 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR²⁰¹R²⁰², in which R²⁰¹ and R²⁰² each, independently, is hydrogen or C1–8 alkyl, (xi) —COOR²⁰³, in which R²⁰³ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR²⁰⁴R²⁰⁵ in which R²⁰⁴ and R²⁰⁵ each, independently, is hydrogen, C1–8 alkyl or phenyl;

R²⁶ is hydrogen, C1–8 alkyl, Cyc2 or C1–8 alkyl substituted by Cyc2;

R²⁷ is hydrogen, C1–8 alkyl, Cyc2 or C1–8 alkyl substituted by Cyc2;

R²⁸ is hydrogen, C1–8 alkyl, Cyc2, C1–8 alkyl substituted by Cyc2, or —COR³⁰, in which R³⁰ is C1–8 alkyl, Cyc2 or C1–8 alkyl substituted by Cyc2;

R²⁹ is hydroxy, C1–8 alkyl, Cyc2, C1–8 alkyl substituted by Cyc2, or —NR³¹R³², in which R³¹ and R³², each independently, is hydrogen, C1–8 alkyl, Cyc2 or C1–8 alkyl substituted by Cyc2;

is carbocyclic ring or heterocyclic ring;

R²⁵ is —E—G;

E is
1) a single bond,
2) —CONR³³—,
3) —NR³³CO—,
4) —CO—O—,
5) —O—CO—,
6) —NR³³—CO—NR³⁴—,
7) —CO—CH₂—,
8) —CO—,
9) —O—CO—NR³³—,
10) —NR³³—CO—O—,
11) —O—CO—O—,
12) —CS—NR³³—, 13) —NR³³—CS—,
14) —CS—O—,
15) —O—CS—,
16) —NR³³—CS—NR³⁴—,
17) —CS—CH₂—,
18) —CS—,
19) —O—CS—NR³³—,
20) —NR³³—CS—O—,
21) —O—CS—O—,
22) —CH₂—CH₂—,
23) —HC=CH—,
24) —C≡C—,
25) —SO₂—NR³³—,
26) —NR³³—SO₂—,
27) —SO₂—CH₂— or
28) —CH₂—SO₂—;

R³³ and R³⁴, each independently, is hydrogen, C1–8 alkyl, Cyc3 or C1–8 alkyl substituted by Cyc3;

Cyc3 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR³⁰¹R³⁰², in which R³⁰¹ and R³⁰² each, independently, is hydrogen or C1–8 alkyl, (xi) —COOR³⁰³, in which R³⁰³ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR³⁰⁴R³⁰⁵, in which R³⁰⁴ and R³⁰⁵ each, independently, is hydrogen, C1–8 alkyl or phenyl;

G is
1) hydrogen,
2) C1-8 alkyl,
3) Cyc4,
4) —OR³⁵,
5) —SR³⁵,
6) halogen atoms,
7) nitro,
8) cyano,
9) —NR³⁶R³⁷,
10) —COR³⁸,
11) C1–8 alkyl substituted by one or more groups selected from Cyc4, —OR³⁵, —SR³⁵, halogen atoms, —NR³⁶R³⁷ and —COR³⁸;

in which Cyc4 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR⁴⁰¹R⁴⁰², in which R⁴⁰¹ and R⁴⁰² each, independently, is hydrogen or C1–8 alkyl, (xi) —COOR⁴⁰³, in which R⁴⁰³ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR⁴⁰⁴R⁴⁰⁵ in which R⁴⁰⁴ and R⁴⁰⁵ each, independently, is hydrogen, C1–8 alkyl or phenyl;

R³⁵ is hydrogen, C1–8 alkyl, C1–8 alkoxy, Cyc4 or C1–8 alkyl substituted by Cyc4;

R³⁶ is hydrogen, C1–8 alkyl, Cyc4, C1–8 alkyl substituted by Cyc4;

R³⁷ is hydrogen, C1–8 alkyl, Cyc4, C1–8 alkyl substituted by Cyc4, or —COR³⁹, in which R³⁹ is C1–8 alkyl, Cyc4 or C1–8 alkyl substituted by Cyc4;

R³⁸ is hydroxy, C1–8 alkyl, Cyc4, C1–8 alkyl substituted by Cyc4, or —NR⁴⁰R⁴¹, in which R⁴⁰ and R⁴¹, each independently, is hydrogen, C1–8 alkyl, Cyc4 or C1–8 alkyl substituted by Cyc4; or —E—G taken together, is C1–4 alkylidene;

p is 1–5;

M is C1–8 alkylene;

J is a single bond, an oxygen atom, a sulfur atom or —NR⁴²—, in which R⁴² is hydrogen or C1–8 alkyl;

═════ is a single bond, or a double bond which prepared by two hydrogens are released, in the case of two of R², R³, R⁴, R⁵, R⁶ and R⁷ which do not bond to a same carbon atom but bond to a neighboring carbon, are hydrogens; with the proviso that ═════ is not a double bond, when R³ and R⁴, taken together is C1–8 alkylene, R⁵ and R⁶, taken together is C1–8 alkylene, R³ and R⁶, taken together is C1–8 alkylene;

with the proviso that (1) at least one of R², R³, R⁴, R⁵, R⁶ and R⁷ is C2–8 alkynyl, or C1–8 alkyl substituted by one or more groups selected from C3–8 alkenyloxy and C3–8 alkynyloxy, (2) when

is benzene, and E is a single bond, then G is not hydrogen;

non-toxic acid thereof, a process for the preparation thereof, and a pharmaceutical agent comprising the same,

[2] a compound which is selected from
(1)5-ethoxymethoxy-4(S)-[N-(4-iodophenylcarbonyl) amino]pentanoic acid,
(2)5-ethoxymethoxy-4(S)-[N-(4-cyanophenylcarbonyl) amino]-2(R)-methoxymethylpentanoic acid,
(3)2(R)-ethoxymethyl-5-ethoxymethoxy-4(S)-[N-(4-nitrophenylcarbonyl)amino]pentanoic acid,
(4)5-ethoxymethoxy-2(S)-(3-thienylmethyl)-4(S)-[N-(4-nitrophenylcarbonyl)amino]pentanoic acid,
(5)5-ethoxymethoxy-2(S)-(3-furylmethyl)-4(S)-[N-(4-nitrophenylcarbonyl)amino]pentanoic acid,
(6)2(S)-benzyl-5-pivaroyloxy-4(S)-[N-(4-nitrophenylcarbonyl)amino]pentanoic acid,
(7)5-acetyloxy-2(S)-benzyl-4(S)-[N-(4-nitrophenylcarbonyl)amino]pentanoic acid,
(8)5-ethoxymethoxy-2(R)-methoxymethyl-4(S)-[N-(4-phenoxy-henylcarbonyl)amino]pentanoic acid,
(9)5-ethoxymethoxy-2(R)-methoxymethyl-4(S)-[N-(4-(2-furyl)phenylcarbonyl)amino]pentanoic acid,
(10)5-ethoxymethoxy-4(S)-[N-(4-cyanophenylcarbonyl) amino]-2(R)-ethoxymethylpentanoic acid,
(11)5-ethoxymethoxy-2(S)-methoxymethyl-4(R)-[N-(4-nitrophenylcarbonyl)amino]pentanoic acid,
(12)5-ethoxymethoxy-2(S)-methoxymethyl-4(R)-[N-(4-chlorophenylcarbonyl)amino]pentanoic acid,
(13)5-ethoxymethoxy-2(S)-methoxymethyl-4(R)-[N-(4-bromophenylcarbonyl)amino]pentanoic acid,
(14)5-ethoxymethoxy-2(S)-methoxymethyl-4(R)-[N-(4-cyanophenylcarbonyl)amino]pentanoic acid,
(15)5-ethoxymethoxy-2(S)-benzyl-4(S)-[N-(4-chlorocyclohexylcarbonyl)amino]pentanoic acid,

(16) 5-ethoxymethoxy-4(S)-[N-(4-nitrophenylcarbonyl) amino]pentanoic acid,
(17) 5-methoxyethoxymethoxy-2(S)-methyl-4(S)-[N-methyl-N-(4-nitrophenylcarbonyl)amino]pentanoic acid,
(18) trans-2-[(4-nitrophenylcarbonyl)aminomethyl] cyclohexanoic acid,
(19) trans-2-[(4-(3-methoxy-1-propynyl)phenylcarbonyl) aminomethyl]cyclohexanoic acid,
(20) trans-2-[((nitrophenylcarbonyl)amino]cyclohexylacetic acid,
(21) N-hydroxy-5-ethoxymethoxy-2(R)-methoxymethyl-4 (S)-[N-(4-cyanophenylcarbonyl)amino]pentanamide,
(22) N-hydroxy-2(R)-ethoxymethyl-5-ethoxymethoxy-4(S)- [N-(4-nitrophenylcarbonyl)amino]pentanamide,
(23) N-hydroxy-5-ethoxymethoxy-2(S)-(3-thienylmethyl)-4 (S)-[N-(4-nitrophenylcarbonyl)amino]pentanamide,
(24) N-hydroxy-5-ethoxymethoxy-2(S)-(3-furylmethyl)-4 (S)-[N-(4-nitrophenylcarbonyl)amino]pentanamide,
(25) N-hydroxy-2(S)-benzyl-5-pivaroyloxy-4(S)-[N-(4-nitrophenylcarbonyl)amino]pentanamide,
(26) N-hydroxy-5-acetyloxy-2(S)-benzyl-4(S)-[N-(4-nitrophenylcarbonyl)amino]pentanamide,
(27) N-hydroxy-5-ethoxymethoxy-2(R)-methoxymethyl-4 (S)-[N-(4-phenoxyphenylcarbonyl)amino]pentanamide,
(28) N-hydroxy-5-ethoxymethoxy-2(R)-methoxymethyl-4 (S)-[N-(4-(2-furyl)phenylcarbonyl)amino]pentanamide,
(29) N-hydroxy-5-ethoxymethoxy-2(R)-ethoxymethyl-4(S)- [N-(4-cyanophenylcarbonyl)amino]pentanamide,
(30) N-hydroxy-5-ethoxymethoxy-2(S)-methoxymethyl-4 (R)-[N-(4-nitrophenylcarbonyl)amino]pentanamide,
(31) N-hydroxy-5-ethoxymethoxy-2(S)-methoxymethyl-4 (R)-[N-(4-chlorophenylcarbonyl)amino]pentanamide,
(32) N-hydroxy-5-ethoxymethoxy-2(S)-methoxymethyl-4 (R)-[N-(4-bromophenylcarbonyl)amino]pentanamide,
(33) N-hydroxy-5-ethoxymethoxy-2(S)-methoxymethyl-4 (R)-[N-(4-cyanophenylcarbonyl)amino]pentanamide,
(34) N-hydroxy-5-ethoxymethoxy-2(S)-benzyl-4(S)-[N-(4-chlorocyclohexylcarbonyl)amino]pentanamide,
(35) N-hydroxy-5-ethoxymethoxy-4(S)-[N-(4-nitrophenylcarbonyl)amino]pentanamide,
(36) N-hydroxy-2(S)-methyl-5-methoxyethoxymethoxy-4 (S)-[N-methyl-N-(4-nitrophenylcarbonyl)amino] pentanamide,
(37) N-hydroxy-5-hydroxy-2(R)-methoxymethyl-4(S)-[N- (4-nitrophenylcarbonyl)amino]pentanamide,
(38) N-hydroxy-5-hydroxy-2(R)-methoxymethyl-4(S)-[N- (4-chlorophenylcarbonyl)amino]pentanamide,
(39) N-hydroxy-2(S)-(2-benzothiophen-3-yl)methyl)-5-hydroxy-4(S)-[N-methyl-N-(4-nitrophenylcarbonyl) amino]pentanamide,
(40) N-hydroxy-2(S)-allyl-5-hydroxy-4(S)-[N-methyl-N-(4-nitrophenylcarbonyl)amino]pentanamide,
(41) N-hydroxy-2(S)-(3-phenylpropyl)-5-hydroxy-4(S)-[N-methyl-N-(4-bromophenylcarbonyl)amino]pentanamide,
(42) N-hydroxy-2(S)-(3-phenylpropyl)-5-hydroxy-4(S)-[N-methyl-N-(4-nitrophenylcarbonyl)amino]pentanamide,
(43) N-hydroxy-2(S)-methyl-5-hydroxy-4(S)-[N-methyl-N- [(5-nitro-2-thienyl)carbonyl]amino]pentanamide,
(44) N-hydroxy-2(S)-benzyl-5-hydroxy-4(S)-[N-methyl-N- [(5-bromo-2-thienyl)carbonyl]amino]pentanamide,
(45) trans-1-(N-hydroxyaminocarbonyl)-2-[(4-nitrophenylcarbonyl)aminomethyl]cyclohexane,
(46) trans-1-(N-hydroxyaminocarbonyl)-2-[(4-(3-methoxy-1-propynyl)phenylcarbonyl)aminomethyl]cyclohexane,
(47) trans-1-(N-hydroxyaminocarbonylmethyl)-2-[(4-nitrophenylcarbonyl)amino]cyclohexane, and methyl ester, t-butyl ester, benzyl ester, allyl ester, and non-toxic salts thereof, and pharmaceutical agents comprising the compound and non-toxic salts thereof as active ingredient.

More particularly, this invention relates to:

[1] (A) the compound of the formula (I) wherein at least one of $R^2$, $R^3$, $R^4$, $R^5$, $R^6$ and $R^7$ is C1–8 alkyl substituted by one or more groups selected from C3–8 alkenyloxy and C3–8 alkynyloxy, non-toxic salts thereof, a process for the preparation thereof, and a pharmaceutical agent comprising the same, (B) the compound of the formula (I) wherein $R^2$, $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, (9) C2–8 alkenyl substituted by one or more groups selected from —$OR^{11}$, —$SR^{11}$, —$NR^{12}R^{13}$, —$COR^{14}$, guanidino and Cyc1, (10) C2–8 alkynyl, or $R^3$ and $R^4$, taken together is C1–8 alkylene, $R^5$ and $R^6$, taken together is C1–8 alkylene, $R^3$ and $R^6{}_1$, taken together is C1–8 alkylene, $R^2$ and $R^3$, taken together is C2–8 alkylene, $R^4$ and $R^5$s taken together is C2–8 alkylene, or $R^6$ and $R^7$, taken together is C2–8 alkylene, and at least one of $R^2$, $R^3$, $R^4$, $R^5$, $R^6$ and $R^7$ is C2–8 alkynyl, non-toxic salts thereof, a process for the preparation thereof, and a pharmaceutical agent comprising the same,

[2] the above compound (1)–compound (47), non-toxic salts thereof and a pharmaceutical agent comprising the same.

More particularly about (B) in the above [1], (B-a) the compound of the formula (I) wherein $R^2$ is 2-propynyl, and $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, or (9) C2–8 alkenyl substituted by one or more groups selected from —$OR^{11}$, —$SR^{11}$, —$NR^{12}R^{13}$, —$COR^{14}$, guanidino and Cyc1, or $R^3$ and $R^4$, takentogether is C1–8 alkylene, $R^5$ and $R^6$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene, non-toxic salts thereof, a process for the preparation thereof, and a pharmaceutical agent comprising the same, and (B-b) the compound of the formula (I) wherein $R^2$, $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —SR11, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, (9) C2–8 alkenyl substituted by one or more groups selected from —$OR^{11}$, —$SR^{11}$, —$NR^{12}R^{13}$, —$COR^{14}$, guanidino and Cyc1, or (10) C2–8 alkynyl, or $R^3$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene, and at least one of $R^2$, $R^3$, $R^4$, $R^5$, $R^6$ and $R^7$ is C2–8 alkynyl, with the exclusion of the following compound:

the compound wherein $R^2$ is 2-propynyl, and $R^3$, $R^4$, $R^5$, $R^6$ and $R^7$ each, independently, is the above groups (1)–(9), or $R^3$ and $R^4$, taken together is C1–8 alkylene, $R^5$ and $R^6$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene;

non-toxic salts thereof, a process for the preparation thereof, and a pharmaceutical agent comprising the same. More particularly about the above (B-b), (B-b1) the compound of the formula (I) wherein $R^2$ is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, or (9) C2–8 alkenyl substituted by one or more groups selected from —$OR^{11}$, —$SR^{11}$, —$NR^{12}R^{13}$, —$COR^{14}$, guanidino and Cyc1, and $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, (9) C2–8 alkenyl substituted by one or more groups selected from —$OR^{11}$, —$SR^{11}$, —$NR^{12}R^{13}$, —$COR^{14}$, guanidino and Cyc1, or (10) C2–8 alkynyl, or $R^3$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene, and at least one of $R^3$, $R^4$, $R^5$, $R^6$ and $R^7$ is C2–8 alkynyl, non-toxic salts thereof, a process for the preparation thereof, and a pharmaceutical agent comprising the same, (B-b2) the compound of the formula (I) wherein $R^2$ is C2–8 alkynyl, and $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}$, —$COR^{14}$, guanidino and Cyc1, (9) C2–8 alkenyl substituted by one or more groups selected from —$OR^{11}$, —$SR^{11}$, —$NR^{12}R^{13}$, —$COR^{14}$, guanidino and Cyc1, or (10) C2–8 alkynyl, or $R^3$ and $R^4$, taken together is C1–8 alkylene, $R^5$ and $R^6{}_1$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene, and at least one of $R^3$, $R^4$, $R^5$, $R^6$ and $R^7$ is C2–8 alkynyl, non-toxic salts thereof, a process for the preparation thereof, and a pharmaceutical agent comprising the same, and (B-b3) the compound of the formula (I) wherein $R^2$ is C2 alkynyl, 1-propynyl, C4–8 alkynyl, and $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) Cyc1, (8) C1–8 alkyl substituted by one or more groups selected from —$OR^{11}$, —$SR^{11}$, —$NR^{12}R^{13}{}_1$, —$COR^{14}$, guanidino and Cyc1, or (9) C2–8 alkenyl substituted by one or more groups selected from —$OR^{11}$, —$SR^{11}$, —$NR^{12}R^{13}$, —$COR^{14}$, guanidino and Cyc1, or $R^3$ and $R^4$, taken together is C1–8 alkylene, $R^5$ and $R^6$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene, non-toxic salts thereof, a process for the preparation thereof, and a pharmaceutical agent comprising the same.

In the present invention, C1–8 alkyl is methyl, ethyl, propyl, butyl, pentyl, hexyl, heptyl, octyl and isomeric groups thereof.

C1–8 alkoxy is methoxy, ethoxy, propoxy, butoxy, pentyloxy, hexyloxy, heptyloxy, octyloxy and isomeric groups thereof.

C1–8 alkyl substituted byphenyl is methyl, ethyl, propyl, butyl, pentyl, hexyl, heptyl, octyl and isomeric groups thereof substituted by one of phenyl.

C1–8 alkyl substituted by C1–8 alkoxy is methyl, ethyl, propyl, butyl, pentyl, hexyl, heptyl, octyl and isomeric groups thereof substituted by one of methoxy, ethoxy, propoxy, butoxy, pentyloxy, hexyloxy, heptyloxy, octyloxy and isomeric groups thereof.

C1–8 alkyl substituted by cyano is methyl, ethyl, propyl, butyl, pentyl, hexyl, heptyl, octyl and isomeric groups thereof substituted by one of cyano.

C1–8 alkyl substituted by C3–8 alkenyloxy is methyl, ethyl, propyl, butyl, pentyl, hexyl, heptyl, octyl and isomeric groups thereof substituted by 2-propenyloxy, 2-butenyloxy, 3-butenyloxy, pentenyloxy, hexenyloxy, heptenyloxy, octenyloxy, pentadienyloxy, hexadienyloxy, heptadienyloxy, octadienyloxy, hexatrienyloxy, heptatrienyloxy, octatrienyloxy and isomeric groups thereof.

C1–8 alkyl substituted by C3–8 alkynyloxy is methyl, ethyl, propyl, butyl, pentyl, hexyl, heptyl, octyl and isomeric groups thereof substituted by 2-propynyloxy, 2-butynyloxy, 3-butynyloxy, pentynyloxy, hexynyloxy, heptynyloxy, octynyloxy and isomeric groups thereof.

C1–8 alkyl substituted by hydroxy is methyl, ethyl, propyl, butyl, pentyl, hexyl, heptyl, octyl and isomeric groups thereof substituted by one of hydroxy.

Oxycarbonyl substituted by phenyl is phenyloxycarbonyl.

Oxycarbonyl substituted by benzyl is benzyloxycarbonyl.

Oxycarbonyl substituted by C1–8 alkyl is methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl and isomeric groups thereof.

C2–8 alkenyl is vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and isomeric groups thereof.

C2–8 alkynyl is ethynyl, 1-propynyl, 2-propynyl, butynyl, pentynyl, hexynyl, heptynyl, octynyl and isomeric groups thereof.

C1–8 alkylene is methylene, ethylene, trimethylene, tetramethylene, pentamethylene, hexamethylene, heptamethylene, octamethylene, and isomeric groups thereof.

C2–8 alkylene is ethylene, trimethylene, tetramethylene, pentamethylene, hexamethylene, heptamethylene, octamethylene, and isomeric groups thereof.

Halogen atom is chlorine, bromine, fluorine, or iodine.

C1–8 alkoxycarbonyl is methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl and isomeric groups thereof.

C1–4 alkylidene is methylidene, ethylidene, propylidene, butylidene and isomeric groups thereof.

Carbocyclic ring is C3–15 mono-, bi- or tri-carbocyclic ring, for example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantane, norcarane.

Heterocyclic ring is 5–18 membered mono-, bi- or tri-heterocyclic ring containing 1–4 of nitrogen(s), 1–2 of oxygen(s) and/or 1–2 of sulfur(s). 5–18 membered mono-, bi- or tri-heterocyclic ring containing 1–4 of nitrogen(s), 1–2 of oxygen(s) and/or 1–2 of sulfur(s) includes 5–18 membered mono-, bi- or tri-heterocyclic aryl containing 1–4 of nitrogen(s), 1–2 of oxygen(s) and/or 1–2 of sulfur(s), partially or fully saturated thereof.

5–18 membered mono-, bi- or tri-heterocyclic aryl containing 1–4 of nitrogen(s), 1–2 of oxygen(s) and/or 1–2 of sulfur(s), is, for example, pyrrole, imidazole, triazole, tetrazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, carbazole or acridine.

Partially or fully saturated 5–18 membered mono-, bi- or tri-heterocyclic ring containing 1–4 of nitrogen(s), 1–2 of oxygen(s) and/or 1–2 of sulfur(s) is, for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzoazepine, benzodiazepine, indolooxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dithiolane, dithiane, dioxazine, dithiazine, 7-oxabicyclo [4.1.0]heptane.

Unless otherwise specified, all isomers are included in the present invention. For example, alkyl, alkenylene, alkynylene, alkoxy, and alkylene include straight-chain and branched-chain ones. Moreover, the isomers in the structure of a double bond, ring, fused ring (E, Z. cis, trans), the isomers generated by the presence of asymmetric carbon atom(s) etc. (R, S isomers, α, β isomers, enantiomers, diastereomers) optically active isomers having optical rotation (D, L, d, l isomers), isomers separated by chromatography (more polar or less polar isomers), equilibrium compounds, compounds of arbitrary ratio of these compounds, racemic mixtures are included in the present invention.

[Salts]

Non-toxic salts of the compound (I) of the present invention include all pharmaceutically acceptable salts, for example, general salts, acid addition salts, hydrate salts.

The compounds of formula (I) and the present compounds of (1)–(47) may be converted into the corresponding salts. Non-toxic and water-soluble salts are preferred. Suitable salts, for example, include:

salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl) amine, lysine, arginine, N-methyl-D-glucamine).

The compounds of the present invention of formula (I) and the present compound (1)–compound (47) may be converted into the corresponding acid addition salts. Non-toxic salts and water-soluble salts are preferred. Suitable salts, for example, include:

salts of inorganic acids e.g. hydrochloride, hydrobromide, hydroiodide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of the present invention of formula (I), the present compound (1)–compound (47) and salts thereof may be converted into the corresponding hydrates by conventional means.

In the compound of the formula (I), a preferred combination of $R^2$, $R^3$, $R^4$, $R^5$, $R^6$ and $R^7$ is that:

[1] $R^2$ is C1–8 alkyl substituted by one or more groups selected from C3–8 alkenyloxy and C3–8 alkynyloxy, $R^3$, $R^4$, $R^5$ and $R^7$ are hydrogen, and $R^6$ is 1) hydrogen, 2) C1–8 alkyl, 3)C2–8 alkenyl, 4) —$OR^{11}$, 5) —$SR^{11}$, 6) —$NR^{12}R^{13}$, 7) Cyc1, 8) C1–8 alkyl substituted by one or more groups selected from —$OR^{11}$, —$SR^{11}$, —$NR^{12}R^{13}$, —$COR^{14}$, guanidino and Cyc1, 9) C2–8 alkenyl substituted by one or more groups selected from —$OR^{11}$, —$SR^{11}$, —$NR^{12}R^{13}$, —$COR^{14}$, guanidino and Cyc1, 10) C2–8 alkynyl, 11) C1–8 alkyl substituted by one or more groups selected from C3–8 alkenyloxy and C3–8 alkynyloxy; specially preferred $R^6$ is 8) C1–8 alkyl substituted by one or more groups selected from —$OR^{11}$, —$SR^{11}$, —$NR^{12}R^{13}$, —$COR^{14}$, guanidino and Cyc1, 9) C2–8 alkenyl substituted by one or more groups selected from —$OR^{11}$, —$SR^{11}$, —$NR^{12}R^{13}$, —$COR^{14}$, guanidino and Cyc1;

[2] $R^2$ is 2-propynyl, $R^3$, $R^4$, $R^5$ and $R^7$ are hydrogen, and $R^6$ is 1) hydrogen, 2) C1–8 alkyl, 3) C2–8 alkenyl, 4) —$OR^{11}$, 5) —$SR^{11}$, 6) —$NR^{12}R^{13}$, 7) Cyc1, 8) C1–8 alkyl substituted by one or more groups selected from —$OR^{11}$, —$SR^{11}$, —$NR^{12}R^{13}$, —$COR^{14}$, guanidino and Cyc1, 9) C2–8 alkenyl substituted by one or more groups selected from —$OR^{11}$, —$SR^{11}$, —$NR^{12}R^{13}$, —$COR^{14}$, guanidino and Cyc1; specially preferred $R^6$ is 8) C1–8 alkyl substituted by one or more groups selected from —$OR^{11}$, —$SR^{11}$, —$NR^{12}R^{13}$, —$COR^{14}$, guanidino and Cyc1, 9) C2–8 alkenyl substituted by one or more groups selected from —OR$^{11}$, —SR$^{11}$, —NR$^{12}$R$^{13}$, —COR$^{14}$, guanidino and Cyc1;

[3] R$^6$ is C2–8 alkynyl, R$^3$, R$^4$, R$^5$ and R$^7$ are hydrogen, and R$^2$ is 1) hydrogen, 2) C1–8 alkyl, 3) C2–8 alkenyl, 4) —OR$^{11}$, 5) —SR$^{11}$, 6) —NR$^{12}$R$^{13}$, 7) Cyc1, 8) C1–8 alkyl substituted by one or more groups selected from —OR$^{11}$, —SR$^{11}$, —NR$^{12}$R$^{13}$, —COR$^{14}$, guanidino and Cyc1, 9) C2–8 alkenyl substituted by one or more groups selected from —OR$^{11}$, —SR$^{11}$, —NR$^{12}$R$^{13}$, —COR$^{14}$, guanidino and Cyc1; specially preferred R$^2$ is 2) C1–8 alkyl, 8) C1–8 alkyl substituted by one or more groups selected from —OR$^{11}$, —SR$^{11}$, —NR$^{12}$R$^{13}$, —COR$^{14}$, guanidino and Cyc1, 9) C2–8 alkenyl substituted by one or more groups selected from —OR$^{11}$, —SR$^{11}$, —NR$^{12}$R$^{13}$, —COR$^{14}$, guanidino and Cyc1;

[4] R$^2$ is C2–8 alkynyl, R$^3$, R$^4$, R$^5$ and R$^7$ are hydrogen, and R$^6$ is C2–8 alkynyl;

[5] R$^2$ is C2 alkynyl (ethynyl), 1-propynyl, C4–8 alkynyl (butynyl, pentynyl, hexynyl, heptynyl, octynyl or isomeric groups thereof), R$^3$, R$^4$, R$^5$ and R$^7$ are hydrogen, and R$^6$ is 1) hydrogen, 2) C1–8 alkyl, 3) C2–8 alkenyl, 4) —OR$^{11}$, 5) —SR$^{11}$, 6) —NR$^{12}$R$^{13}$, 7) Cyc1, 8) C1–8 alkyl substituted by one or more groups selected from —OR$^{11}$, —SR$^{11}$, —NR$^{12}$R$^{13}$, —COR$^{14}$, guanidino and Cyc1, 9) C2–8 alkenyl substituted by one or more groups selected from —OR$^{11}$, —SR$^{11}$, —NR$^{12}$R$^{13}$, —COR$^{14}$, guanidino and Cyc1; specially preferred R$^6$ is 8) C1–8 alkyl substituted by one or more groups selected from —OR$^{11}$, —SR$^{11}$, —NR$^{12}$R$^{13}$, —COR$_{14}$, guanidino and Cyc1, 9) C2–8 alkenyl substituted by one or more groups selected from —OR$^{11}$, —SR$^{11}$, —NR$^{12}$R$^{13}$, —COR$^{14}$.

In the compound of formula (I), preferred are the compound of the formula (Ia)

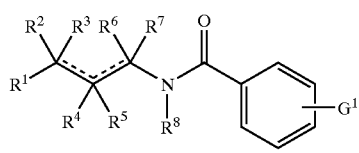

(Ia)

wherein G$^1$ is methyl, halogen atoms, nitro, cyano or phenoxy, and the other symbols are as hereinbefore defined; or the compound of the formula (Ib):

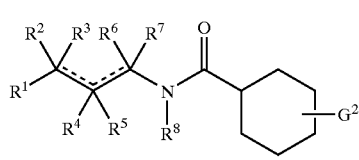

(Ib)

wherein G$^2$ is methyl, halogen atoms, nitro or cyano, the other symbols are as hereinbefore defined.

Concretely, the compounds in the Table 1–Table 25, non-toxic salts thereof and the compounds described in Example are preferable. Besides, in the following table, EOM means ethoxymethyl, a mark "*" in the formula means an asymmetric carbon, and each of R, S and RS isomers is included.

TABLE 1

(I-A1)

| No. | R$^1$ | R$^8$ | R$^9$ |
|---|---|---|---|
| 1 | COOH | H | —C$_6$H$_4$-Cl (4-Cl-phenyl) |
| 2 | COOH | H | 4-Br-phenyl |
| 3 | COOH | H | 4-NO$_2$-phenyl |
| 4 | COOH | H | 4-CN-phenyl |
| 5 | COOH | H | 4-phenoxy-phenyl |
| 6 | COOH | H | 4-CH$_3$-cyclohexyl |
| 7 | COOH | —CH$_3$ | 4-Cl-phenyl |
| 8 | COOH | —CH$_3$ | 4-Br-phenyl |
| 9 | COOH | —CH$_3$ | 4-NO$_2$-phenyl |
| 10 | COOH | —CH$_3$ | 4-CN-phenyl |
| 11 | COOH | —CH$_3$ | 4-phenoxy-phenyl |
| 12 | COOH | —CH$_3$ | 4-CH$_3$-cyclohexyl |

TABLE 2

(I-A2)

| No. | R¹ | R⁸ | R⁹ |
|---|---|---|---|
| 1 | CONHOH | H |  4-Cl-C₆H₄ |
| 2 | CONHOH | H | 4-Br-C₆H₄ |
| 3 | CONHOH | H | 4-NO₂-C₆H₄ |
| 4 | CONHOH | H | 4-CN-C₆H₄ |
| 5 | CONHOH | H | 4-PhO-C₆H₄ |
| 6 | CONHOH | H | 4-CH₃-C₆H₁₀ |
| 7 | CONHOH | —CH₃ | 4-Cl-C₆H₄ |
| 8 | CONHOH | —CH₃ | 4-Br-C₆H₄ |
| 9 | CONHOH | —CH₃ | 4-NO₂-C₆H₄ |
| 10 | CONHOH | —CH₃ | 4-CN-C₆H₄ |
| 11 | CONHOH | —CH₃ | 4-PhO-C₆H₄ |
| 12 | CONHOH | —CH₃ | 4-CH₃-C₆H₁₀ |

TABLE 3

(I-A3)

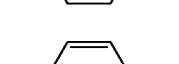

| No. | R¹ | R⁸ | R⁹ |
|---|---|---|---|
| 1 | CONHNH₂ | H | 4-Cl-C₆H₄ |
| 2 | CONHNH₂ | H | 4-Br-C₆H₄ |
| 3 | CONHNH₂ | H | 4-NO₂-C₆H₄ |
| 4 | CONHNH₂ | H | 4-CN-C₆H₄ |
| 5 | CONHNH₂ | H | 4-PhO-C₆H₄ |
| 6 | CONHNH₂ | H | 4-CH₃-C₆H₁₀ |
| 7 | CONHNH₂ | —CH₃ | 4-Cl-C₆H₄ |
| 8 | CONHNH₂ | —CH₃ | 4-Br-C₆H₄ |
| 9 | CONHNH₂ | —CH₃ | 4-NO₂-C₆H₄ |
| 10 | CONHNH₂ | —CH₃ | 4-CN-C₆H₄ |
| 11 | CONHNH₂ | —CH₃ | 4-PhO-C₆H₄ |
| 12 | CONHNH₂ | —CH₃ | 4-CH₃-C₆H₁₀ |

TABLE 4

(I-A4)

| No. | R¹ | R⁸ | R⁹ |
|---|---|---|---|
| 1 | CH₂—SH | H |  4-Cl-C₆H₄ |
| 2 | CH₂—SH | H |  4-Br-C₆H₄ |
| 3 | CH₂—SH | H |  4-NO₂-C₆H₄ |
| 4 | CH₂—SH | H | 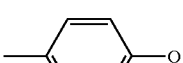 4-CN-C₆H₄ |
| 5 | CH₂—SH | H | 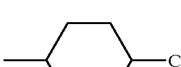 4-PhO-C₆H₄ |
| 6 | CH₂—SH | H | 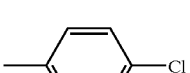 4-CH₃-cyclohexyl |
| 7 | CH₂—SH | —CH₃ | 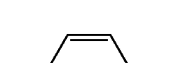 4-Cl-C₆H₄ |
| 8 | CH₂—SH | —CH₃ | 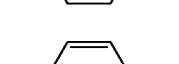 4-Br-C₆H₄ |
| 9 | CH₂—SH | —CH₃ |  4-NO₂-C₆H₄ |
| 10 | CH₂—SH | —CH₃ | 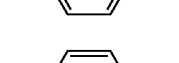 4-CN-C₆H₄ |
| 11 | CH₂—SH | —CH₃ | 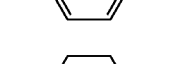 4-PhO-C₆H₄ |
| 12 | CH₂—SH | —CH₃ |  4-CH₃-cyclohexyl |

TABLE 5

(I-A5)

| No. | R¹ | R⁸ | R⁹ |
|---|---|---|---|
| 1 | PO(OH)₂ | H |  4-Cl-C₆H₄ |
| 2 | PO(OH)₂ | H | 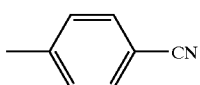 4-Br-C₆H₄ |
| 3 | PO(OH)₂ | H | 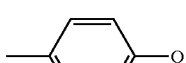 4-NO₂-C₆H₄ |
| 4 | PO(OH)₂ | H | 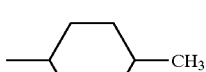 4-CN-C₆H₄ |
| 5 | PO(OH)₂ | H |  4-PhO-C₆H₄ |
| 6 | PO(OH)₂ | H | 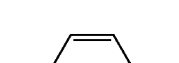 4-CH₃-cyclohexyl |
| 7 | PO(OH)₂ | —CH₃ |  4-Cl-C₆H₄ |
| 8 | PO(OH)₂ | —CH₃ | 4-Br-C₆H₄ |
| 9 | PO(OH)₂ | —CH₃ | 4-NO₂-C₆H₄ |
| 10 | PO(OH)₂ | —CH₃ |  4-CN-C₆H₄ |
| 11 | PO(OH)₂ | —CH₃ | 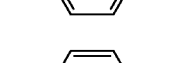 4-PhO-C₆H₄ |
| 12 | PO(OH)₂ | —CH₃ | 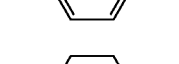 4-CH₃-cyclohexyl |

TABLE 6
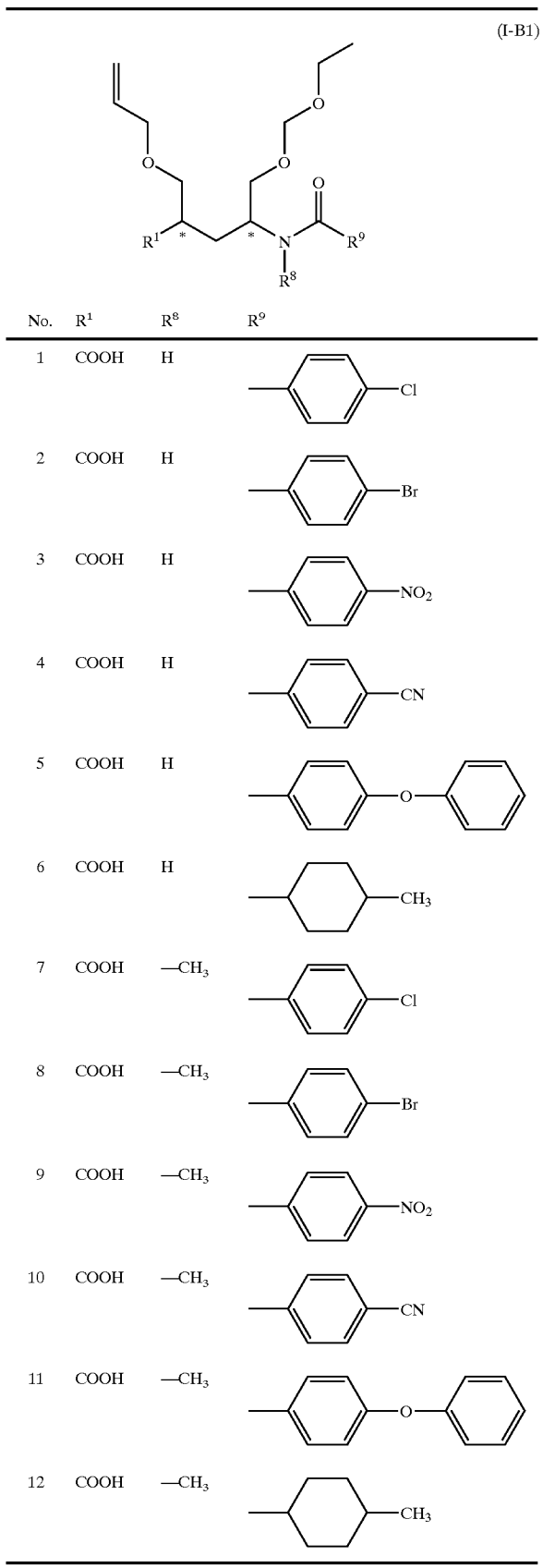
TABLE 7
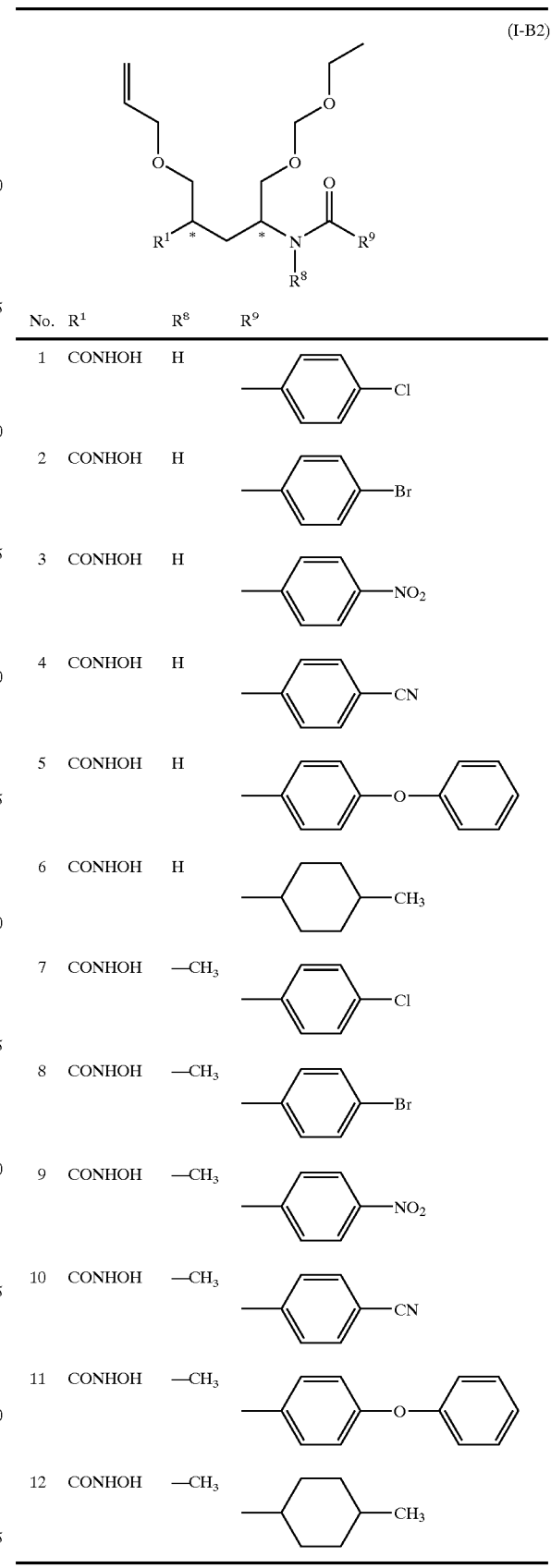

TABLE 8
(I-B3)
| No. | R¹ | R⁸ | R⁹ |
|---|---|---|---|
| 1 | CONHNH₂ | H | 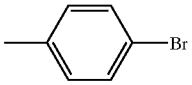 |
| 2 | CONHNH₂ | H | 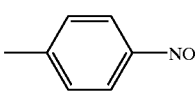 |
| 3 | CONHNH₂ | H | 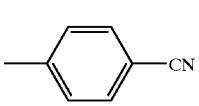 |
| 4 | CONHNH₂ | H | 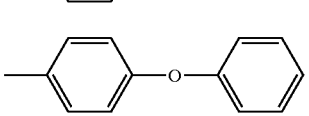 |
| 5 | CONHNH₂ | H | 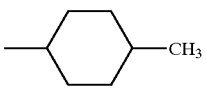 |
| 6 | CONHNH₂ | H | 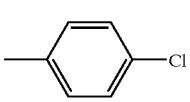 |
| 7 | CONHNH₂ | —CH₃ | 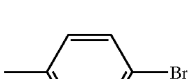 |
| 8 | CONHNH₂ | —CH₃ | 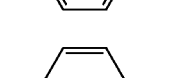 |
| 9 | CONHNH₂ | —CH₃ | 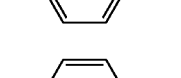 |
| 10 | CONHNH₂ | —CH₃ | 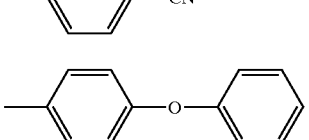 |
| 11 | CONHNH₂ | —CH₃ |  |
| 12 | CONHNH₂ | —CH₃ |  |
TABLE 9
(I-B4)
| No. | R¹ | R⁸ | R⁹ |
|---|---|---|---|
| 1 | CH₂—SH | H |  |
| 2 | CH₂—SH | H | 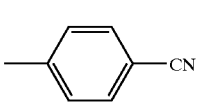 |
| 3 | CH₂—SH | H | 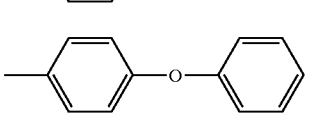 |
| 4 | CH₂—SH | H | 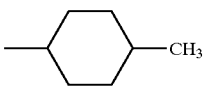 |
| 5 | CH₂—SH | H | 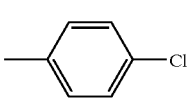 |
| 6 | CH₂—SH | H | 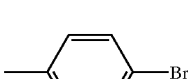 |
| 7 | CH₂—SH | —CH₃ | 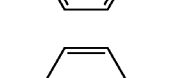 |
| 8 | CH₂—SH | —CH₃ | 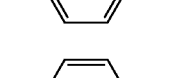 |
| 9 | CH₂—SH | —CH₃ | 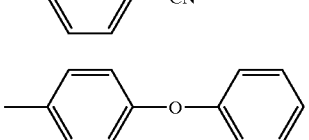 |
| 10 | CH₂—SH | —CH₃ |  |
| 11 | CH₂—SH | —CH₃ | |
| 12 | CH₂—SH | —CH₃ | |

TABLE 10

(I-B5)

Structure: Allyl-O-CH2-CH(R1)-CH2-CH(N(R8)(C(=O)R9))-CH2-O-CH2-O-Ethyl (with * chiral centers)

| No. | R¹ | R⁸ | R⁹ |
|---|---|---|---|
| 1 | PO(OH)₂ | H | 4-Cl-C₆H₄- |
| 2 | PO(OH)₂ | H | 4-Br-C₆H₄- |
| 3 | PO(OH)₂ | H | 4-NO₂-C₆H₄- |
| 4 | PO(OH)₂ | H | 4-CN-C₆H₄- |
| 5 | PO(OH)₂ | H | 4-PhO-C₆H₄- |
| 6 | PO(OH)₂ | H | 4-CH₃-cyclohexyl |
| 7 | PO(OH)₂ | —CH₃ | 4-Cl-C₆H₄- |
| 8 | PO(OH)₂ | —CH₃ | 4-Br-C₆H₄- |
| 9 | PO(OH)₂ | —CH₃ | 4-NO₂-C₆H₄- |
| 10 | PO(OH)₂ | —CH₃ | 4-CN-C₆H₄- |
| 11 | PO(OH)₂ | —CH₃ | 4-PhO-C₆H₄- |
| 12 | PO(OH)₂ | —CH₃ | 4-CH₃-cyclohexyl |

TABLE 11

(I-C1)

Structure: CH≡C-CH2-CH(N(R8)(C(=O)R9))-CH2-CH(CH3)(R1) (with * chiral centers)

| No. | R¹ | R⁸ | R⁹ |
|---|---|---|---|
| 1 | COOH | H | 4-Cl-C₆H₄- |
| 2 | COOH | H | 4-Br-C₆H₄- |
| 3 | COOH | H | 4-NO₂-C₆H₄- |
| 4 | COOH | H | 4-CN-C₆H₄- |
| 5 | COOH | H | 4-PhO-C₆H₄- |
| 6 | COOH | H | 4-CH₃-cyclohexyl |
| 7 | COOH | —CH₃ | 4-Cl-C₆H₄- |
| 8 | COOH | —CH₃ | 4-Br-C₆H₄- |
| 9 | COOH | —CH₃ | 4-NO₂-C₆H₄- |
| 10 | COOH | —CH₃ | 4-CN-C₆H₄- |
| 11 | COOH | —CH₃ | 4-PhO-C₆H₄- |
| 12 | COOH | —CH₃ | 4-CH₃-cyclohexyl |

TABLE 12 (I-C2)

| No. | R¹ | R⁸ | R⁹ |
|---|---|---|---|
| 1 | CONHOH | H | 4-Cl-C₆H₄ |
| 2 | CONHOH | H | 4-Br-C₆H₄ |
| 3 | CONHOH | H | 4-NO₂-C₆H₄ |
| 4 | CONHOH | H | 4-CN-C₆H₄ |
| 5 | CONHOH | H | 4-PhO-C₆H₄ |
| 6 | CONHOH | H | 4-CH₃-C₆H₁₀ |
| 7 | CONHOH | —CH₃ | 4-Cl-C₆H₄ |
| 8 | CONHOH | —CH₃ | 4-Br-C₆H₄ |
| 9 | CONHOH | —CH₃ | 4-NO₂-C₆H₄ |
| 10 | CONHOH | —CH₃ | 4-CN-C₆H₄ |
| 11 | CONHOH | —CH₃ | 4-PhO-C₆H₄ |
| 12 | CONHOH | —CH₃ | 4-CH₃-C₆H₁₀ |

TABLE 13 (I-C3)

| No. | R¹ | R⁸ | R⁹ |
|---|---|---|---|
| 1 | CONHNH₂ | H | 4-Cl-C₆H₄ |
| 2 | CONHNH₂ | H | 4-Br-C₆H₄ |
| 3 | CONHNH₂ | H | 4-NO₂-C₆H₄ |
| 4 | CONHNH₂ | H | 4-CN-C₆H₄ |
| 5 | CONHNH₂ | H | 4-PhO-C₆H₄ |
| 6 | CONHNH₂ | H | 4-CH₃-C₆H₁₀ |
| 7 | CONHNH₂ | —CH₃ | 4-Cl-C₆H₄ |
| 8 | CONHNH₂ | —CH₃ | 4-Br-C₆H₄ |
| 9 | CONHNH₂ | —CH₃ | 4-NO₂-C₆H₄ |
| 10 | CONHNH₂ | —CH₃ | 4-CN-C₆H₄ |
| 11 | CONHNH₂ | —CH₃ | 4-PhO-C₆H₄ |
| 12 | CONHNH₂ | —CH₃ | 4-CH₃-C₆H₁₀ |

TABLE 14

(I-C4)

Structure: R¹—*CH(CH₃)—CH₂—*CH(CH₂—C≡CH)—N(R⁸)—C(=O)—R⁹

| No. | R¹ | R⁸ | R⁹ |
|---|---|---|---|
| 1 | CH₂—SH | H | 4-Cl-C₆H₄— |
| 2 | CH₂—SH | H | 4-Br-C₆H₄— |
| 3 | CH₂—SH | H | 4-NO₂-C₆H₄— |
| 4 | CH₂—SH | H | 4-CN-C₆H₄— |
| 5 | CH₂—SH | H | 4-PhO-C₆H₄— |
| 6 | CH₂—SH | H | 4-CH₃-C₆H₁₀— |
| 7 | CH₂—SH | —CH₃ | 4-Cl-C₆H₄— |
| 8 | CH₂—SH | —CH₃ | 4-Br-C₆H₄— |
| 9 | CH₂—SH | —CH₃ | 4-NO₂-C₆H₄— |
| 10 | CH₂—SH | —CH₃ | 4-CN-C₆H₄— |
| 11 | CH₂—SH | —CH₃ | 4-PhO-C₆H₄— |
| 12 | CH₂—SH | —CH₃ | 4-CH₃-C₆H₁₀— |

TABLE 15

(I-C5)

Structure: R¹—*CH(CH₃)—CH₂—*CH(CH₂—C≡CH)—N(R⁸)—C(=O)—R⁹

| No. | R¹ | R⁸ | R⁹ |
|---|---|---|---|
| 1 | PO(OH)₂ | H | 4-Cl-C₆H₄— |
| 2 | PO(OH)₂ | H | 4-Br-C₆H₄— |
| 3 | PO(OH)₂ | H | 4-NO₂-C₆H₄— |
| 4 | PO(OH)₂ | H | 4-CN-C₆H₄— |
| 5 | PO(OH)₂ | H | 4-PhO-C₆H₄— |
| 6 | PO(OH)₂ | H | 4-CH₃-C₆H₁₀— |
| 7 | PO(OH)₂ | —CH₃ | 4-Cl-C₆H₄— |
| 8 | PO(OH)₂ | —CH₃ | 4-Br-C₆H₄— |
| 9 | PO(OH)₂ | —CH₃ | 4-NO₂-C₆H₄— |
| 10 | PO(OH)₂ | —CH₃ | 4-CN-C₆H₄— |
| 11 | PO(OH)₂ | —CH₃ | 4-PhO-C₆H₄— |
| 12 | PO(OH)₂ | —CH₃ | 4-CH₃-C₆H₁₀— |

TABLE 16

(I-D1)

Structure: R¹-*CH(CH₂C≡CH)-CH₂-*CH(CH₂C≡CH)-N(R⁸)-C(=O)-R⁹

| No. | R¹ | R⁸ | R⁹ |
|---|---|---|---|
| 1 | COOH | H | 4-Cl-C₆H₄ |
| 2 | COOH | H | 4-Br-C₆H₄ |
| 3 | COOH | H | 4-NO₂-C₆H₄ |
| 4 | COOH | H | 4-CN-C₆H₄ |
| 5 | COOH | H | 4-PhO-C₆H₄ |
| 6 | COOH | H | 4-CH₃-cyclohexyl |
| 7 | COOH | —CH₃ | 4-Cl-C₆H₄ |
| 8 | COOH | —CH₃ | 4-Br-C₆H₄ |
| 9 | COOH | —CH₃ | 4-NO₂-C₆H₄ |
| 10 | COOH | —CH₃ | 4-CN-C₆H₄ |
| 11 | COOH | —CH₃ | 4-PhO-C₆H₄ |
| 12 | COOH | —CH₃ | 4-CH₃-cyclohexyl |

TABLE 17

(I-D2)

Structure: R¹-*CH(CH₂C≡CH)-CH₂-*CH(CH₂C≡CH)-N(R⁸)-C(=O)-R⁹

| No. | R¹ | R⁸ | R⁹ |
|---|---|---|---|
| 1 | CONHOH | H | 4-Cl-C₆H₄ |
| 2 | CONHOH | H | 4-Br-C₆H₄ |
| 3 | CONHOH | H | 4-NO₂-C₆H₄ |
| 4 | CONHOH | H | 4-CN-C₆H₄ |
| 5 | CONHOH | H | 4-PhO-C₆H₄ |
| 6 | CONHOH | H | 4-CH₃-cyclohexyl |
| 7 | CONHOH | —CH₃ | 4-Cl-C₆H₄ |
| 8 | CONHOH | —CH₃ | 4-Br-C₆H₄ |
| 9 | CONHOH | —CH₃ | 4-NO₂-C₆H₄ |
| 10 | CONHOH | —CH₃ | 4-CN-C₆H₄ |
| 11 | CONHOH | —CH₃ | 4-PhO-C₆H₄ |
| 12 | CONHOH | —CH₃ | 4-CH₃-cyclohexyl |

TABLE 18

(I-D3)

| No. | R¹ | R⁸ | R⁹ |
|---|---|---|---|
| 1 | CONHNH₂ | H |  4-Cl-C₆H₄ |
| 2 | CONHNH₂ | H | 4-Br-C₆H₄ |
| 3 | CONHNH₂ | H | 4-NO₂-C₆H₄ |
| 4 | CONHNH₂ | H | 4-CN-C₆H₄ |
| 5 | CONHNH₂ | H | 4-PhO-C₆H₄ |
| 6 | CONHNH₂ | H | 4-CH₃-C₆H₁₀ |
| 7 | CONHNH₂ | —CH₃ | 4-Cl-C₆H₄ |
| 8 | CONHNH₂ | —CH₃ | 4-Br-C₆H₄ |
| 9 | CONHNH₂ | —CH₃ | 4-NO₂-C₆H₄ |
| 10 | CONHNH₂ | —CH₃ | 4-CN-C₆H₄ |
| 11 | CONHNH₂ | —CH₃ | 4-PhO-C₆H₄ |
| 12 | CONHNH₂ | —CH₃ | 4-CH₃-C₆H₁₀ |

$R^1 = CONHNH_2$; structures shown in images above.

TABLE 19

(I-D4)

| No. | R¹ | R⁸ | R⁹ |
|---|---|---|---|
| 1 | CH₂—SH | H | 4-Cl-C₆H₄ |
| 2 | CH₂—SH | H | 4-Br-C₆H₄ |
| 3 | CH₂—SH | H | 4-NO₂-C₆H₄ |
| 4 | CH₂—SH | H | 4-CN-C₆H₄ |
| 5 | CH₂—SH | H | 4-PhO-C₆H₄ |
| 6 | CH₂—SH | H | 4-CH₃-C₆H₁₀ |
| 7 | CH₂—SH | —CH₃ | 4-Cl-C₆H₄ |
| 8 | CH₂—SH | —CH₃ | 4-Br-C₆H₄ |
| 9 | CH₂—SH | —CH₃ | 4-NO₂-C₆H₄ |
| 10 | CH₂—SH | —CH₃ | 4-CN-C₆H₄ |
| 11 | CH₂—SH | —CH₃ | 4-PhO-C₆H₄ |
| 12 | CH₂—SH | —CH₃ | 4-CH₃-C₆H₁₀ |

TABLE 20

(I-D5)

| No. | R¹ | R⁸ | R⁹ |
|---|---|---|---|
| 1 | PO(OH)₂ | H |  4-Cl-C₆H₄ |
| 2 | PO(OH)₂ | H | 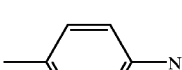 4-Br-C₆H₄ |
| 3 | PO(OH)₂ | H | 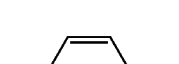 4-NO₂-C₆H₄ |
| 4 | PO(OH)₂ | H | 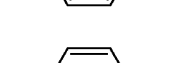 4-CN-C₆H₄ |
| 5 | PO(OH)₂ | H | 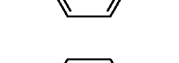 4-PhO-C₆H₄ |
| 6 | PO(OH)₂ | H | 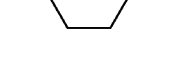 4-CH₃-C₆H₁₀ |
| 7 | PO(OH)₂ | —CH₃ | 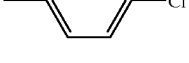 4-Cl-C₆H₄ |
| 8 | PO(OH)₂ | —CH₃ | 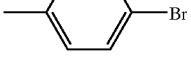 4-Br-C₆H₄ |
| 9 | PO(OH)₂ | —CH₃ |  4-NO₂-C₆H₄ |
| 10 | PO(OH)₂ | —CH₃ |  4-CN-C₆H₄ |
| 11 | PO(OH)₂ | —CH₃ | 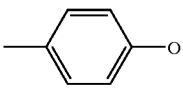 4-PhO-C₆H₄ |
| 12 | PO(OH)₂ | —CH₃ |  4-CH₃-C₆H₁₀ |

TABLE 21

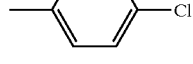
(I-E1)

| No. | R¹ | R⁸ | R⁹ |
|---|---|---|---|
| 1 | COOH | H | 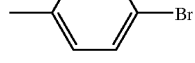 4-Cl-C₆H₄ |
| 2 | COOH | H | 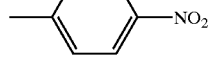 4-Br-C₆H₄ |
| 3 | COOH | H | 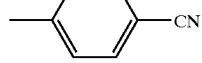 4-NO₂-C₆H₄ |
| 4 | COOH | H | 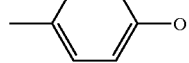 4-CN-C₆H₄ |
| 5 | COOH | H |  4-PhO-C₆H₄ |
| 6 | COOH | H |  4-CH₃-C₆H₁₀ |
| 7 | COOH | —CH₃ |  4-Cl-C₆H₄ |
| 8 | COOH | —CH₃ | 4-Br-C₆H₄ |
| 9 | COOH | —CH₃ | 4-NO₂-C₆H₄ |
| 10 | COOH | —CH₃ |  4-CN-C₆H₄ |
| 11 | COOH | —CH₃ | 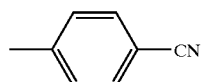 4-PhO-C₆H₄ |
| 12 | COOH | —CH₃ | 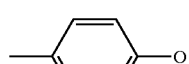 4-CH₃-C₆H₁₀ |

TABLE 22
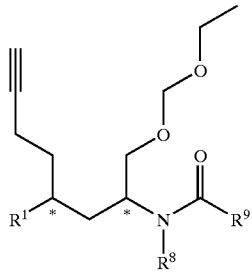
(I-E2)
| No. | R¹ | R⁸ | R⁹ |
|---|---|---|---|
| 1 | CONHOH | H | 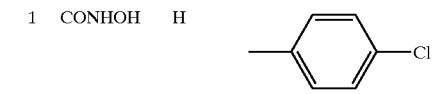 |
| 2 | CONHOH | H | 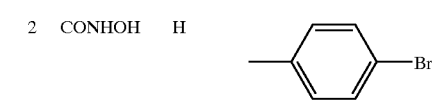 |
| 3 | CONHOH | H | 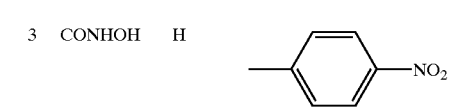 |
| 4 | CONHOH | H | 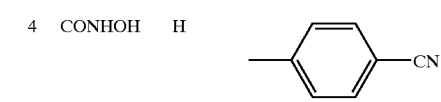 |
| 5 | CONHOH | H | 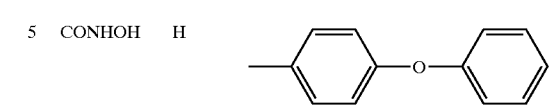 |
| 6 | CONHOH | H | 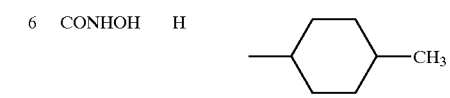 |
| 7 | CONHOH | —CH₃ | 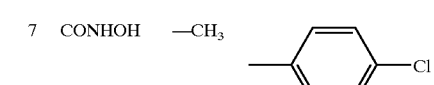 |
| 8 | CONHOH | —CH₃ | 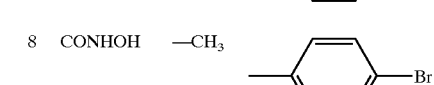 |
| 9 | CONHOH | —CH₃ | 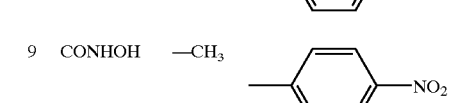 |
| 10 | CONHOH | —CH₃ | 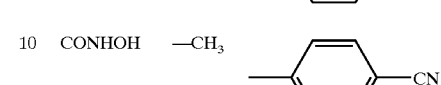 |
| 11 | CONHOH | —CH₃ | 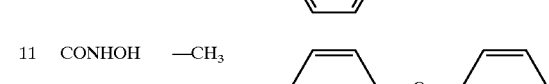 |
| 12 | CONHOH | —CH₃ | 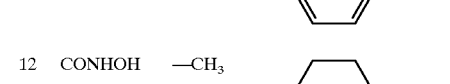 |
TABLE 23
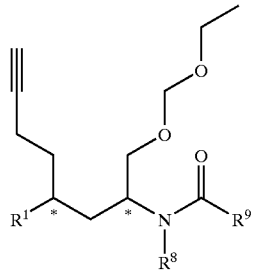
(I-E3)
| No. | R¹ | R⁸ | R⁹ |
|---|---|---|---|
| 1 | CONHNH₂ | H | 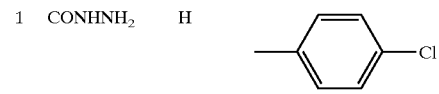 |
| 2 | CONHNH₂ | H | 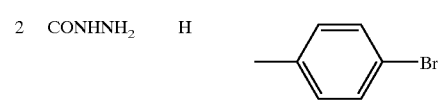 |
| 3 | CONHNH₂ | H | 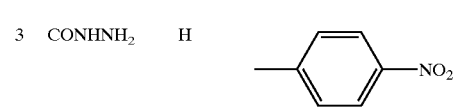 |
| 4 | CONHNH₂ | H | 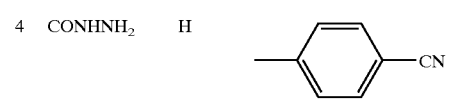 |
| 5 | CONHNH₂ | H | 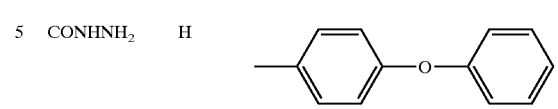 |
| 6 | CONHNH₂ | H | 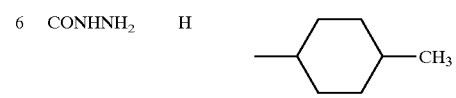 |
| 7 | CONHNH₂ | —CH₃ | 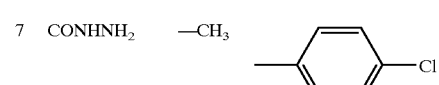 |
| 8 | CONHNH₂ | —CH₃ | 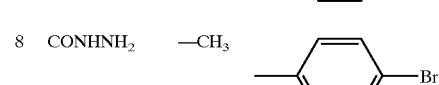 |
| 9 | CONHNH₂ | —CH₃ | 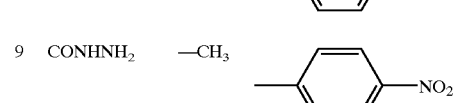 |
| 10 | CONHNH₂ | —CH₃ | 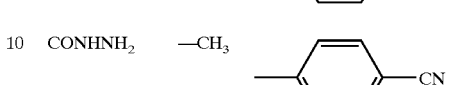 |
| 11 | CONHNH₂ | —CH₃ |  |
| 12 | CONHNH₂ | —CH₃ | 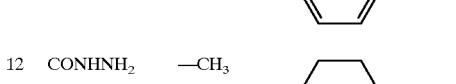 |

TABLE 24

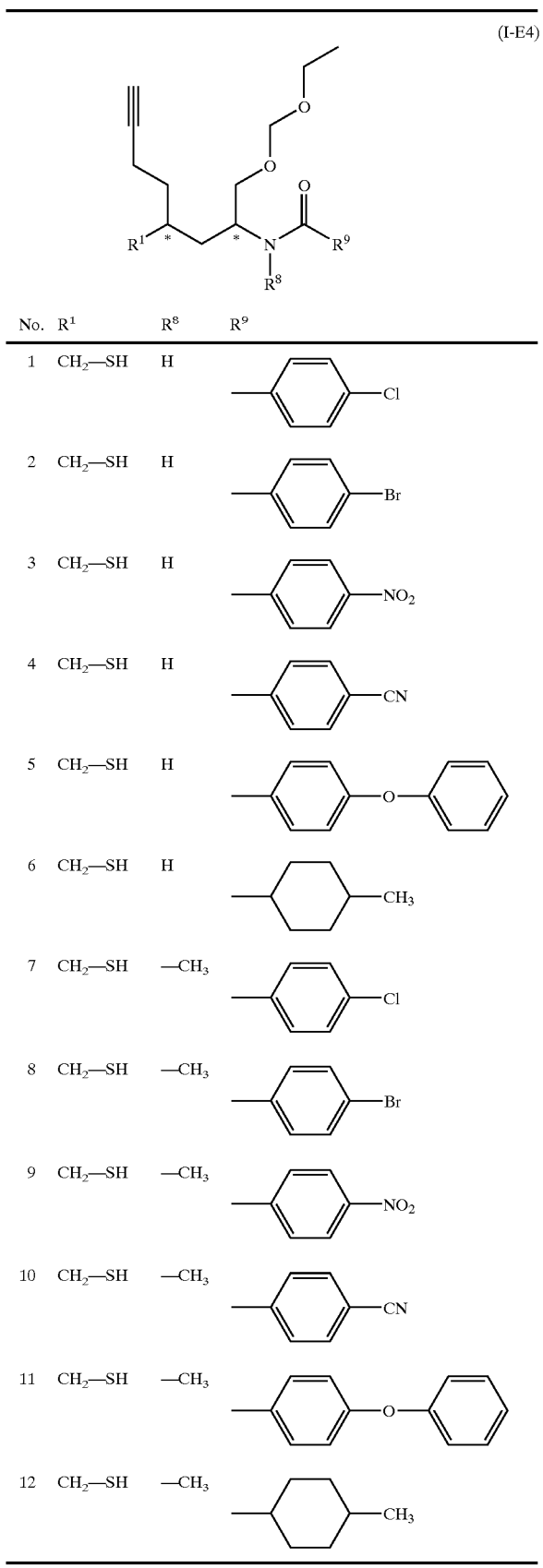

(I-E4)

| No. | R¹ | R⁸ | R⁹ |
|---|---|---|---|
| 1 | CH₂—SH | H | 4-Cl-C₆H₄ |
| 2 | CH₂—SH | H | 4-Br-C₆H₄ |
| 3 | CH₂—SH | H | 4-NO₂-C₆H₄ |
| 4 | CH₂—SH | H | 4-CN-C₆H₄ |
| 5 | CH₂—SH | H | 4-PhO-C₆H₄ |
| 6 | CH₂—SH | H | 4-CH₃-C₆H₁₀ |
| 7 | CH₂—SH | —CH₃ | 4-Cl-C₆H₄ |
| 8 | CH₂—SH | —CH₃ | 4-Br-C₆H₄ |
| 9 | CH₂—SH | —CH₃ | 4-NO₂-C₆H₄ |
| 10 | CH₂—SH | —CH₃ | 4-CN-C₆H₄ |
| 11 | CH₂—SH | —CH₃ | 4-PhO-C₆H₄ |
| 12 | CH₂—SH | —CH₃ | 4-CH₃-C₆H₁₀ |

TABLE 25

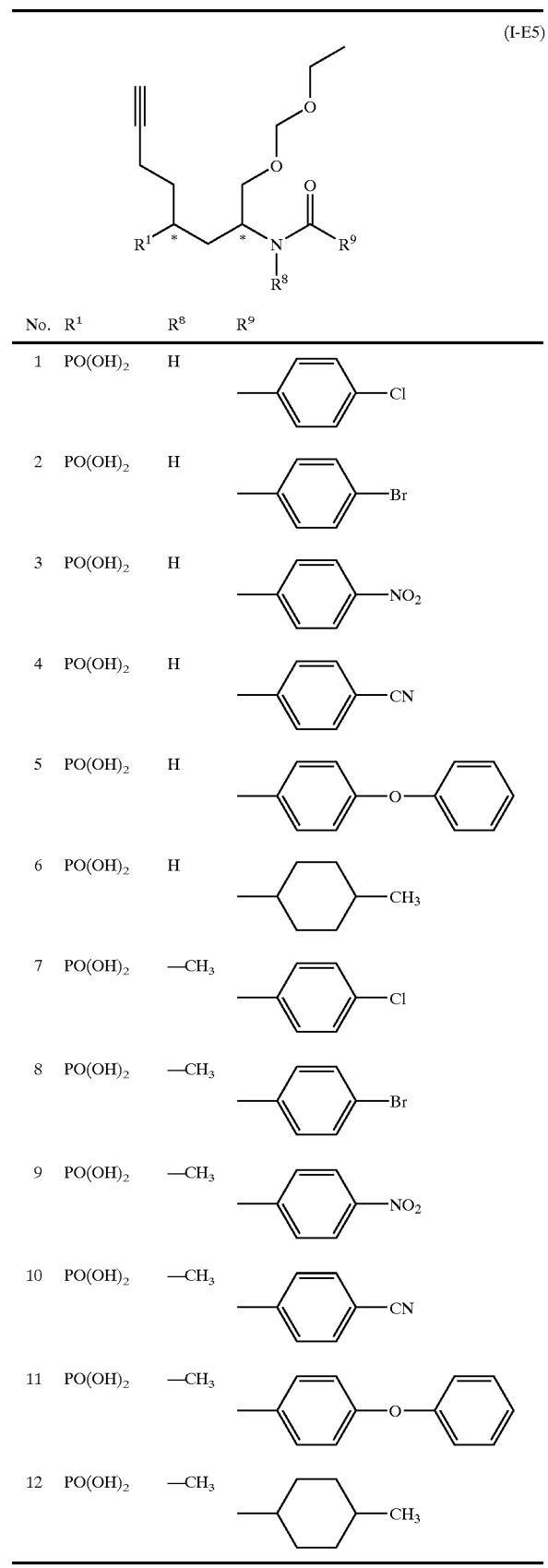

(I-E5)

| No. | R¹ | R⁸ | R⁹ |
|---|---|---|---|
| 1 | PO(OH)₂ | H | 4-Cl-C₆H₄ |
| 2 | PO(OH)₂ | H | 4-Br-C₆H₄ |
| 3 | PO(OH)₂ | H | 4-NO₂-C₆H₄ |
| 4 | PO(OH)₂ | H | 4-CN-C₆H₄ |
| 5 | PO(OH)₂ | H | 4-PhO-C₆H₄ |
| 6 | PO(OH)₂ | H | 4-CH₃-C₆H₁₀ |
| 7 | PO(OH)₂ | —CH₃ | 4-Cl-C₆H₄ |
| 8 | PO(OH)₂ | —CH₃ | 4-Br-C₆H₄ |
| 9 | PO(OH)₂ | —CH₃ | 4-NO₂-C₆H₄ |
| 10 | PO(OH)₂ | —CH₃ | 4-CN-C₆H₄ |
| 11 | PO(OH)₂ | —CH₃ | 4-PhO-C₆H₄ |
| 12 | PO(OH)₂ | —CH₃ | 4-CH₃-C₆H₁₀ |

[Process for the Preparation]

The compounds of the present invention of the formula (I), may be prepared by following methods or the methods described in the Examples.

[1] The compound in which $R^1$ is —COOR$^{10}$, that is the compound of the formula (I-1)

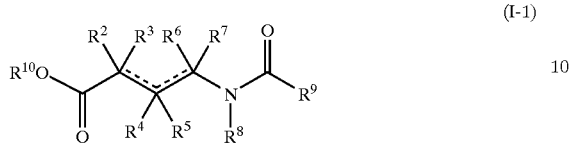

(I-1)

wherein all the symbols are as hereinbefore defined; may be prepared by following methods (a)–(c).

(a) The compound in which —COOR$^{10}$ of $R^1$ is not —COOH, and all of $R^2$, $R^3$, $R^4$, $R^5$, $R^6$, $R^7$, $R^8$ and $R^9$ are not hydroxy, amino, or a group including —COOH, hydroxy or amino, that is the compound of the formula (I-1a):

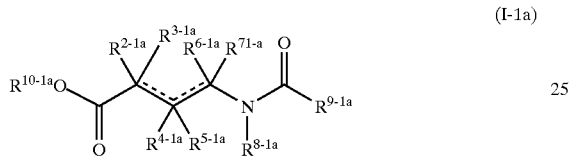

(I-1a)

wherein $R^{10-1a}$ is C1–8 alkyl, C2–8 alkenyl, phenyl, C1–8 alkyl substituted by phenyl or C1–8 alkoxy, oxycarbonyl substituted by phenyl, benzyl or C1–8 alkyl, each of $R^{2-1a}$, $R^{3-1a}$, $R^{4-1a}$, $R^{5-1a}$, $R^{6-1a}$, $R^{7-1a}$, $R^{8-1a}$ and $R^{9-1a}$ is the same meaning as $R^2$, $R^3$, $R^4$, $R^5$, $R^6$, $R^7$, $R^8$ and $R^9$, with the proviso that, all of $R^{2-1a}$, $R^{3-1a}$, $R^{4-1a}$, $R^{5-1a}$, $R^{6-1a}$, $R^{7-1a}$, $R^{8-1a}$, $R^{9-1a}$ are not hydroxy, amino, or group including —COOH, hydroxy or amino, and the other symbols are as hereinbefore defined;

may be prepared by amidation of the compound of the formula (II):

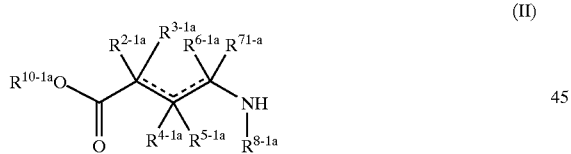

(II)

wherein all the symbols are as hereinbefore defined; with the compound of the formula (III):

(III)

wherein all the symbols are as hereinbefore defined.

The method of amidation of the compound of the formula (II) with the compound of the formula (III) is known. It includes the method
(1) via an acyl halide,
(2) via a mixed acid anhydride,
(3) using a condensing agent.
These methods are explained as follows.
(1) The method via an acyl halide, for example, may be carried out in an organic solvent (e.g. chloroform, methylene chloride, diethyl ether or tetrahydrofuran) or without a solvent, using an acyl halide (e.g. oxalyl chloride or thionyl chloride etc.) at −20° C. to reflux temperature, and the obtained acyl halide derivative may be reacted with an amine in an organic solvent (e.g. chloroform, methylene chloride, diethyl ether or tetrahydrofuran) in the presence of a tertiary amine (e.g. pyridine, triethyl amine, dimethyl aniline or dimethylaminopyridine) at 0–40° C.

(2) The method via a mixed acid anhydride may be carried out, for example, by reacting a carboxylic acid with an acyl halide (e.g. pivaloyl chloride, tosyl chloride or mesyl chloride) or an acid derivative (e.g. ethyl chloroformate or isobutyl chloroformate) in an organic solvent (e.g. chloroform, methylene chloride, diethyl ether or tetrahydrofuran) or without a solvent, in the presence of a tertiary amine (e.g. pyridine, triethylamine, dimethylaniline or dimethylaminopyridine) at 0–40° C., and the obtained mixed acid anhydride derivative may be reacted with a corresponding amine in an organic solvent (e.g. chloroform, methylene chloride, diethyl ether or tetrahydrofuran) at 0–40° C.

(3) The method using a condensing agent (e.g. 1,3-dicyclohexyl carbodiimide (DCC), 1-ethyl-3-[3-(dimethylamino)propl]carbodiimide (EDC), 1,1'-carbonyldiimidazole (CDI) or 2-chloro-1-methylpyridinium iodide) maybe carried out, for example, by reacting a carboxylic acid with an amine in an organic solvent (e.g. chloroform, methylene chloride, dimethylformamide, diethyl ether or tetrahydrofuran) or without a solvent, optionally in the presence of a tertiary amine (e.g. pyridine, triethylamine, dimethylaniline or dimethylaminopyridine) using a condensing agent, and optionally in the presence of 1-hydroxybenzotriazole (HOBt) at 0–40° C.

The reaction described in (1), (2) and (3) may be carried out under an inert gas (e.g. argon, nitrogen) to avoid water in order to obtain a preferable result.

Besides, a different ester of the formula (I-1a) may be prepared by subjecting the compound of the formula (I-1aa)

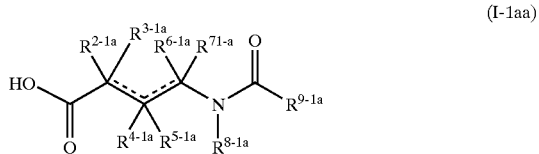

(I-1aa)

wherein all the symbols are as hereinbefore defined;
that was obtained by deprotection under alkaline conditions, deprotection under acidic conditions, hydrogenelysis, or deprotection of allyl ester from the compound of the formula (I-1a); to esterification reaction.

The esterification reaction is known, for example, it may be carried out in organic solvent (e.g. acetone, acetonitrile, DMF), in the presence of alkali carbonate (e.g. potassium carbonate, sodium carbonate, cesium carbonate), using a catalyst (e.g. sodium iodide) or without a catalyst, at 0–100° C.

Further, the compound of the formula (I-1a) may be also prepared by reacting the compound of the formula (I-1a) in which $R^{8-1a}$ is hydrogen, that is the compound of the formula (I-1ab)

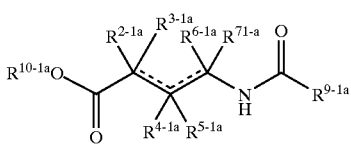

(I-1ab)

wherein all the symbols are as hereinbefore defined; with the compound of the formula (XIII)

X—R$^{8-1ab}$ (XIII)

wherein X is halogen atoms, R$^{8-1ab}$ is the same meaning as R$^{8-1a}$, with the proviso that it is not represented hydrogen, and by reacting the compound of the formula (I-1a) in which R$^{2-1a}$ is hydrogen, that is the compound of the formula (I-1ac)

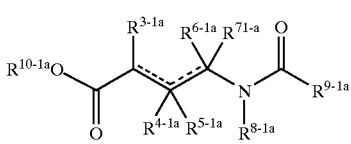

(I-1ac)

wherein all the symbols are as hereinbefore defined; with the compound of the formula (XIV)

X—R$^{2-1a}$ (XIV)

wherein all the symbols are as hereinbefore defined.

Furthermore, the compound of the formula (I-1a) maybe also prepared by reacting the compound of the formula (I-1ac) in which R$^{8-1a}$ is hydrogen, with the compound of the formula (XIV) and then the compound of the formula (XIII)

X—R$^{8-1ab}$ (XIII)

wherein all the symbols are as hereinbefore defined.

The reaction of the compound of the formula (I-11ab) and the compound of the formula (XIII), and the compound prepared by reacting the compound in which R$^{8-1a}$ is hydrogen in the compound of the formula (I-1ac) with the compound of the formula (XIV), and the compound of the formula (XIII), is known, for example, may be carried out in an organic solvent (e.g. THF), in the presence of a base (e.g. sodium hydroxide), at −20–50° C.

The reaction of the compound of the formula (I-1ac) and the compound of the formula (XIV), for example, may be carried out in an organic solvent (e.g. THF, ethyleneglycol dimethyl ether), in the presence of a base (e.g. lithium bis (trimethylsilyl) amide, lithium diisopropylamide), adding an addition (e.g. 1,3-dimethyl-2-imidazolidinone, hexamethylphospholamide) or without an addition, at −78° C.

(b) The compound in which —COOR$^{10}$ of R$^1$ is not —COOH, and at least one of R$^2$, R$^3$, R$^4$, R$^5$, R$^6$, R$^7$, R$^8$ and R$^9$ is hydroxy, amino, or a group including —COOH, hydroxy or amino, that is the compound of the formula (I-1b):

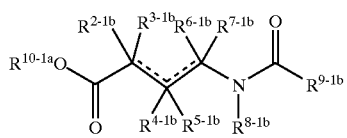

(I-1b)

wherein each of R$^{2-1b}$, R$^{3-1b}$, R$^{4-1b}$, R$^{5-1b}$, R$^{6-1b}$, R$^{7-1b}$, R$^{8-1b}$, R$^{9-1b}$ is the a same meaning as R$^2$, R$^3$, R$^4$, R$^5$, R$^6$, R$^7$, R$^8$, R$^9$, with the proviso that, at least one of R$^{2-1b}$, R$^{3-1b}$, R$^{4-1b}$, R$^{5-1b}$, R$^{6-1b}$, R$^{7-1b}$, R$^{8-1b}$, R$^{9-1b}$ is hydroxy, amino, or a group including —COOH, hydroxy or amino, and the other symbols are as hereinbefore defined;

may be prepared by deprotection under alkaline conditions, deprotection under acidic conditions, deprotection of a silyl group or hydrogenolysis of the compound having protected hydroxy or amino, or groups including protected —COOH, hydroxy or amino in the compound of the formula (I-1a), that is the compound of the formula (I-1a1):

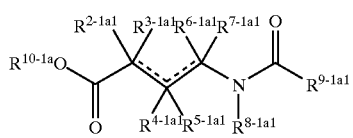

(I-1a1)

wherein each of R$^{2-1a1}$, R$^{3-1a1}$, R$^{4-1a1}$, R$^{5-1a1}$, R$^{6-1a1}$, R$^{7-1a1}$, R$^{8-1a1}$, R$^{9-1a1}$ is the a same meaning as R$^2$, R$^3$, R$^4$, R$^5$, R$^6$, R$^7$, R$^8$, R$^9$, with the proviso that, at least one of R$^{2-1a1}$, R$^{3-1a1}$, R$^{4-1a1}$, R$^{5-1a1}$, R$^{6-1a1}$, R$^{7-1a1}$, R$^{8-1a1}$, R$^{9-1a1}$ is protected hydroxy (e.g. protected by methoxymethyl, ethoxymethyl, methoxyethyl, tetrahydropyranyl, t-butyldimethylsilyl, acetyl, benzyl), protected amino (e.g. protected by benzyloxycarboyl, t-butoxycarbonyl, trifluoroacetyl), or a group including protected —COOH (e.g. protected by methyl, ethyl, t-butyl and benzyl), protected hydroxy or protected amino, and the other symbols are as hereinbefore defined.

Deprotection under alkaline conditions is known, for example, it may be carried out in an organic solvent (e.g. methanol, tetrahydrofuran or dioxane), using an alkali metal hydroxide (e.g. sodium hydroxide, potassium hydroxide or lithium hydroxide), an alkaline earth metal hydroxide (e.g. barium hydroxide or calcium hydroxide) or a carbonate (e.g. sodium carbonate or potassium carbonate), an aqueous solution thereof or mixture thereof at 0–40° C.

Deprotection under acidic conditions is known, for example, it may be carried out in an organic solvent (e.g. methylene chloride, chloroform, dioxane, ethyl acetate, anisole), using an organic acid (e.g. acetic acid, trifluoroacetic acid, methanesulfonic acid or trimethylsilyl iodide), or an inorganic acid (e.g. hydrochloric acid or sulfuric acid) or a mixture thereof (e.g. hydrogen bromide in acetic acid) at 0–100° C.

Deprotection of a silyl group is known, for example, it may be carried out in a water miscible organic solvent (e.g. tetrahydrofuran or acetonitrile), using tetrabutylammonium fluoride at 0–40° C.

Hydrogenolysis is known, for example, it may be carried out in a solvent [e.g. ether (such as tetrahydrofuran, dioxane, dimethoxyethane or diethyl ether), alcohol (such as methanol or ethanol), benzene (such as benzene or toluene), ketone (such as acetone or methyl ethyl ketone), nitrile (such as acetonitrile), amide (such as dimethylformamide), water, ethyl acetate, acetic acid or two more mixture thereof], in the presence of a catalyst (e.g. palladium on carbon, palladium black, palladium, palladium hydroxide, platinum dioxide, nickel or Raney-nickel), optionally in the presence of an inorganic acid (e.g. hydrochloric acid, sulfuric acid, hypochlorous acid, boric acid or tetrafluoroboric acid) or an organic acid (e.g. acetic acid, p-toluenesulfonic acid, oxalic acid, trifluoroacetic acid or formic acid), at ordinary or elevated pressure of hydrogen gas or ammonium formate at 0–200° C. It has no difficulty in using a salt of acid, when it is carried out using an acid.

(c) The compound in which —COOR$^{10}$ of R$^1$ is —COOH, that is the compound of the formula (I-1c):

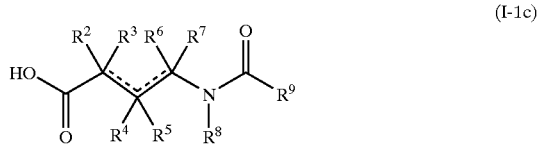

(I-1c)

wherein all the symbols are the same meaning as hereinbefore defined;

may be prepared by deprotection under alkaline conditions, deprotection under acidic conditions, hydrogenolysis or deprotection of allyl ester of the above compounds of the formula (I-1a) and the formula (I-1b).

The reaction of deprotection under alkaline conditions, deprotection under acidic conditions and hydrogenolysis are known and they may be carried out by the same method as hereinbefore described.

The reaction of deprotection of allyl ester is known, for example, it may be carried out in an organic solvent [e.g. ether (such as THF, dioxane, dimethoxyethane or diethyl ether), alcohol (such as methanol or ethanol), benzene (such as benzene or toluene), ketone (such as acetone or methyl ethyl ketone), nitrile (such as acetonitrile), amide (such as DMF)], in the presence of a catalyst (e.g. palladium, such as tetrakis(triphenylphosphin)palladium(0)), in the presence of secondary amine (e.g. morphorine, piperadine) or/and trimethylsilyl halide, at 0–100° C.

[2] In the compounds of the present invention of the formula (I), the compound in which R$^1$ is —CONHOR$^{10}$ or —CONHNHR$^{10}$, that is the compound of the formula (I-2):

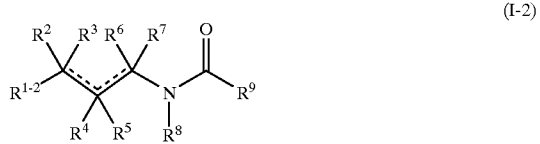

(I-2)

wherein R$^{2-1}$ is —CONHOR$^{10}$ or —CONHNHR$^{10}$, and the other symbols are as hereinbefore defined; may be prepared by following methods (a) and (b).

(a) The compound in which R$^1$ is —CONHOR$^{10}$ or —CONHNHR$^{10}$, and all of R$^2$, R$^3$, R$^4$, R$^5$, R$^6$, R$^7$, R$^8$ and R$^9$ are not a group including —COOH, that is the compound of the formula (I-2a):

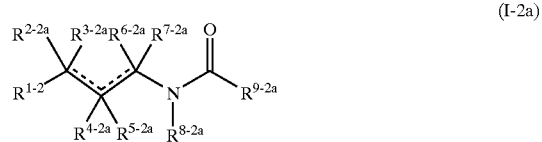

(I-2a)

wherein each of R$^{2-2a}$, R$^{3-2a}$, R$^{4-2a}$, R$^{5-2a}$, R$^{6-2a}$, R$^{7-2a}$, R$^{8-2a}$, R$^{9-2a}$ is the a same meaning as R$^2$, R$^3$, R$^4$, R$^5$, R$^6$, R$^7$, R$^8$, R$^9$, with the proviso that, all of R$^{2-2a}$, R$^{3-2a}$, R$^{4-2a}$, R$^{5-2a}$, R$^{6-2a}$, R$^{7-2a}$, R$^{8-2a}$, R$^{9-2a}$ are not a group including —COOH, and the other symbols are as hereinbefore defined;

may be prepared by amidation of the compound of the above formula (I-1) in which R$^1$ is COOH, and all of R$^2$, R$^3$, R$^4$, R$^5$, R$^6$, R$^7$, R$^8$, R$^9$, are not a group including —COOH, that is the compound of the formula (I-1d):

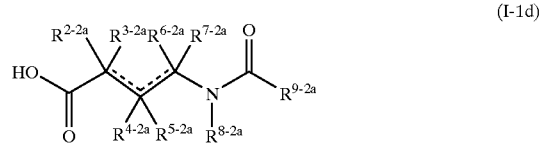

(I-1d)

wherein all the symbols are as hereinbefore defined; with the compound of the formula (IV):

$$H_2N—OR^{10}$$ (IV)

wherein R$^{10}$ is as hereinbefore defined; or the compound of the formula (V):

$$H_2N—NHR^{10}$$ (V)

wherein R$^{10}$ is the same meaning as hereinbefore defined; if necessary, continuously, by deprotection under alkaline conditions and/or deprotection under acidic conditions and/or hydrogenolysis.

This reaction of amidation, the reactions of deprotection under alkaline conditions, deprotection under acidic conditions and hydrogenolysis are known, and may be carried out by the same method as hereinbefore described.

(b) The compound in which R$^1$ is —CONHOR$^{10}$ or —CONHNHR$^{10}$, and at least one of R$^2$, R$^3$, R$^4$, R$^5$, R$^6$, R$^7$, R$^8$ and R$^9$ is a group including —COOH, that is the compound of the formula (I-2b)

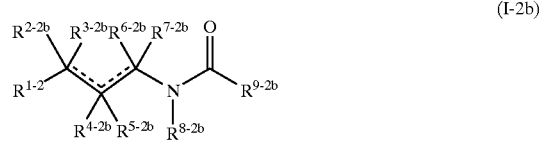

(I-2b)

wherein each of R$^{2-2b}$, R$^{3-2b}$, R$^{4-2b}$, R$^{5-2b}$, R$^{6-2b}$, R$^{7-2b}$, R$^{8-2b}$, R$^{9-2b}$ is the a same meaning as R$^2$, R$^3$, R$^4$, R$^5$, R$^6$, R$^7$, R$^8$, R$^9$, with the proviso that, at least one of R$^{2-2b}$, R$^{3-2b}$, R$^{4-2b}$, R$^{5-2b}$, R$^{6-2b}$, R$^{7-2b}$, R$^{8-2b}$, R$^{9-2b}$ is a group including —COOH, and the other symbols are as hereinbefore defined;

may be prepared by deprotection under alkaline conditions, deprotection under acidic conditions or hydrogenolysis of the compound of the above formula (I-2a) having a group including protected —COOH, that is the compound of the formula (I-2a1)

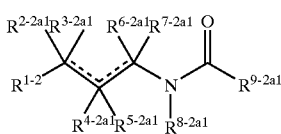

(I-2a1)

wherein each of $R^{2-2a1}$, $R^{3-2a1}$, $R^{4-2a1}$, $R^{5-2a1}$, $R^{6-2a1}$, $R^{7-2a1}$, $R^{8-2a1}$, $R^{9-2a1}$ is the a same meaning as $R^2$, $R^3$, $R^4$, $R^5$, $R^6$, $R^7$, $R^8$, $R^9$, with the proviso that, at least one of $R^{2-2a1}$, $R^{3-2a1}$, $R^{4-2a1}$, $R^{5-2a1}$, $R^{6-2a1}$, $R^{7-2a1}$, $R^{8-2a1}$, $R^{9-2a1}$ is a group including protected —COOH (e.g. protected by methyl, ethyl, t-butyl and benzyl), and the other symbols are as hereinbefore defined.

The reactions of deprotection under alkaline conditions, deprotection under acidic conditions and hydrogenolysis are known, and may be carried out by the same method as hereinbefore described.

[3] In the compounds of the present invention of the formula (I), the compound in which $R^1$ is —$(CH_2)_nSR^{50}$, that is the compound of the formula (I-3)

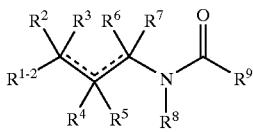

(I-3)

wherein $R^{1-3}$ is —$(CH_2)_nSR^{50}$, and the other symbols are as hereinbefore defined;

may be prepared by following methods (a) and (b).

(a) The compound in which $R^1$ is —$(CH_2)_nSR^{50}$, and all of $R^2$, $R^3$, $R^4$, $R^5$, $R^6$, $R^7$, $R^8$ and $R^9$ are not hydroxy, amino, or a group including —COOH, hydroxy or amino, that is the compound of the formula (I-3a)

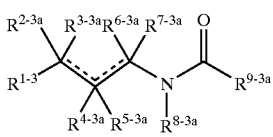

(I-3a)

wherein each of $R^{2-3a}$, $R^{3-3a}$, $R^{4-3a}$, $R^{5-3a}$, $R^{6-3a}$, $R^{7-3a}$, $R^{8-3a}$, $R^{9-3a}$ is the a same meaning as $R^2$, $R^3$, $R^4$, $R^5$, $R^6$, $R^7$, $R^8$, $R^9$, with the proviso that, all of $R^{2-3a}$, $R^{3-3a}$, $R^{4-3a}$, $R^{5-3a}$, $R^{6-3a}$, $R^{7-3a}$, $R^{8-3a}$, $R^{9-3a}$ are not hydroxy, amino, or a group including —COOH, hydroxy or amino, and the other symbols are as hereinbefore defined;

may be prepared by reaction of the compound of the formula (VI)

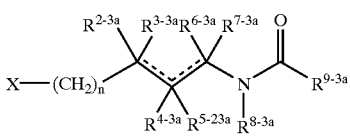

(VI)

wherein X is halogen atoms and the other symbols are as hereinbefore defined;

with the compound of the formula (VII)

$R^{501}SK$ (VII)

wherein $R^{501}$ is C1–8 alkyl, —$COR^{52}$, —$SR^{531}$, in which $R^{531}$ is C1–8 alkyl or phenyl.

The compound of the formula (I-3a) in which $R^{50}$ is hydrogen or —SH may be prepared by a reaction of deprotection of the compound obtained by the above method.

The above method is known, for example, it may be carried out by refluxing in an organic solvent (e.g. acetone, tetrahydrofuran).

The continuous reaction, that is deprotection is known, for example, it may be carried out in an organic solvent (e.g. methanol, tetrahydrofuran or dioxane), using an alkali metal hydroxide (e.g. sodium hydroxide, potassium hydroxide or lithium hydroxide), an alkaline earth metal hydroxide (e.g. barium hydroxide or calcium hydroxide) or a carbonate (e.g. sodium carbonate or potassium carbonate), an aqueous solution thereof or mixture thereof at 0–40° C.

(b) The compound in which $R^1$ is —$(CH_2)_nSR^{50}$, and at least one of $R^2$, $R^3$, $R^4$, $R^5$, $R^6$, $R^7$, $R^8$ and $R^9$ is a group including —COOH, hydroxy or a group including it, amino or a group including it, that is the compound of the formula (I-3b)

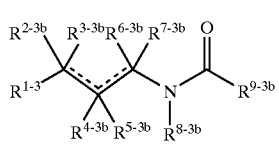

(I-3b)

wherein each of $R^{2-3b}$, $R^{3-3b}$, $R^{4-3b}$, $R^{5-3b}$, $R^{6-3b}$, $R^{7-3b}$, $R^{8-3b}$, $R^{9-3b}$ is the a same meaning as $R^2$, $R^3$, $R^4$, $R^5$, $R^6$, $R^7$, $R^8$, $R^9$, with the proviso that, at least one of $R^{2-3b}$, $R^{3-3b}$, $R^{4-3b}$, $R^{5-3b}$, $R^{6-3b}$, $R^{7-3b}$, $R^{8-3b}$, $R^{9-3b}$ is hydroxy, amino, or a group including —COOH, hydroxy or amino, and the other symbols are as hereinbefore defined;

may be prepared by deprotection under alkaline conditions, deprotection under acidic conditions or hydrogenolysis of the compound of the above formula (I-3a) having protected hydroxy, protected amino, or a group including protected —COOH, hydroxy or amino, that is the compound of the formula (I-3a1)

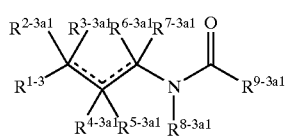

(I-3a1)

wherein each of $R^{2-3a1}$, $R^{3-3a1}$, $R^{4-3a1}$, $R^{5-3a1}$, $R^{6-3a1}$, $R^{7-3a1}$, $R^{8-3a1}$, $R^{9-3a1}$ is the a same meaning as $R^2$, $R^3$, $R^4$, $R^5$, $R^6$, $R^7$, $R^8$, $R^9$, with the proviso that, at least one of $R^{2-3a1}$, $R^{3-3a1}$, $R^{4-3a1}$, $R^{5-3a1}$, $R^{6-3a1}$, $R^{7-3a1}$, $R^{8-3a1}$, $R^{9-3a1}$ is protected hydroxy (e.g. protected by methoxymethyl, ethyoxymethyl, methoxyethyl, tetrahydropyranyl, t-butyldimethylsilyl, acetyl or benzyl), or protected amino (e.g. protected by benzyloxycarboyl, t-butoxycarbonyl, trifluoroacetyl), or a group including protected —COOH (e.g. protected by methyl, ethyl, t-butyl and benzyl), protected hydroxy or protected amino, and the other symbols are as hereinbefore defined.

The reactions of deprotection under alkaline conditions, deprotection under acidic conditions and hydrogenolysis are known, and may be carried out by the same method as hereinbefore described.

[4] In the compounds of the present invention of the formula (I), the compound in which $R^1$ is —Y—PO(OR$^{51}$)$_2$, that is the compound of the formula (I-4)

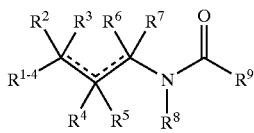
(I-4)

wherein $R^{1-4}$ is —Y—PO(OR$^{51}$)$_2$, and the other symbols are as hereinbefore defined;

may be prepared by following methods (a)–(d).

(a) The compound in which $R^1$ is —Y$^1$—PO(OR$^{51}$)$_2$, in which $Y^1$ is —O— and the other symbols are as hereinbefore defined; and all of $R^2$, $R^3$, $R^4$, $R^5$, $R^6$, $R^7$, $R^8$ and $R^9$ are not hydroxy, amino, or a group including —COOH, hydroxy or amino, that is the compound of the formula (I-4a)

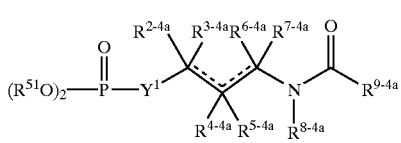
(I-4a)

wherein each of $R^{2-4a}$, $R^{3-4a}$, $R^{4-4a}$, $R^{5-4a}$, $R^{6-4a}$, $R^{7-4a}$, $R^{8-4a}$, $R^{9-4a}$ is the a same meaning as $R^2$, $R^3$, $R^4$, $R^5$, $R^6$, $R^7$, $R^8$, $R^9$, with the proviso that, all of $R^{2-4a}$, $R^{3-4a}$, $R^{4-4a}$, $R^{5-4a}$, $R^{6-4a}$, $R^{7-4a}$, $R^{8-4a}$, $R^{9-4a}$ are not hydroxy, amino, or a group including —COOH, hydroxy or amino, and the other symbols are as hereinbefore defined;

may be prepared by reaction of the compound of the formula (VIII)

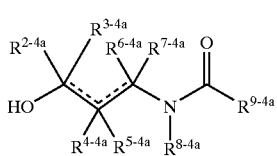
(VIII)

wherein all the symbols are as hereinbefore defined; with the compound of the formula (IX)

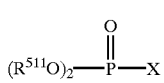
(IX)

wherein $R^{511}$ is C1–8 alkyl, phenyl or a known protecting group of phosphoric acid and the other symbols are as hereinbefore defined;

when using the compound of the formula (IX) in which $R^{511}$ is protected phosphoric acid, continuously, by deprotection.

The above reaction is known, for example, it may be carried out in an organic solvent (e.g. pyridine) at 0–40° C.

The reaction of deprotection of phosphoric acid is known, for example, it may be carried out in an organic solvent (e.g. pyridine), using zinc acetate at 0–40° C.

(b) The compound in which $R^1$ is —Y$^1$—PO(OR$^{51}$)$_2$, and at least one of $R^2$, $R^3$, $R^4$, $R^5$, $R^6$, $R^7$, $R^8$ and $R^9$ is hydroxy, amino, or a group including —COOH, hydroxy or amino, that is the compound of the formula (I-4b)

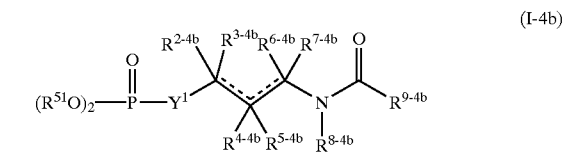
(I-4b)

wherein each of $R^{2-4b}$, $R^{3-4b}$, $R^{4-4b}$, $R^{5-4b}$, $R^{6-4b}$, $R^{7-4b}$, $R^{8-4b}$, $R^{9-4b}$ is the a same meaning as $R^2$, $R^3$, $R^4$, $R^5$, $R^6$, $R^7$, $R^8$, $R^9$, with the proviso that, at least one of $R^{2-4b}$, $R^{3-4b}$, $R^{4-4b}$, $R^{5-4b}$, $R^{6-4b}$, $R^{7-4b}$, $R^{8-4b}$, $R^{9-4b}$ is hydroxy, amino, or a group including —COOH, hydroxy or amino, and the other symbols are as hereinbefore defined;

may be prepared by deprotection under alkaline conditions, deprotection under acidic conditions or hydrogenolysis of the compound of the above formula (I-4a) having a group including protected hydroxy, protected amino, or a group including protected —COOH, protected hydroxy or protected amino, that is the compound of the formula (I-4a1)

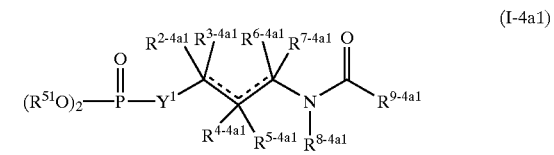
(I-4a1)

wherein each of $R^{2-4a1}$, $R^{3-4a1}$, $R^{4-4a1}$, $R^{5-4a1}$, $R^{6-4a1}$, $R^{7-4a1}$, $R^{8-4a1}$, $R^{9-4a1}$ is the a same meaning as $R^2$, $R^3$, $R^4$, $R^5$, $R^6$, $R^7$, $R^8$, $R^9$, with the proviso that, at least one of $R^{2-4a1}$, $R^{3-4a1}$, $R^{4-4a1}$, $R^{5-4a1}$, $R^{6-4a1}$, $R^{7-4a1}$, $R^{8-4a1}$, $R^{9-4a1}$ is protected hydroxy (e.g. protected by methoxymethyl, ethoxymethyl, methoxyethyl, tetrahydropyranyl, t-butyldimethylsilyl, acetyl, benzyl), protected amino (e.g. protected by benzyloxycarboyl, t-butoxycarbonyl, trifluoroacetyl), or a group including protected —COOH (e.g. protected by methyl, ethyl, t-butyl and benzyl), protected hydroxy or protected amino, and the other symbols are as hereinbefore defined.

The reactions of deprotection under alkaline conditions, deprotection under acidic conditions and hydrogenolysis are known, and may be carried out by the same method as hereinbefore described.

(c) The compound in which $R^1$ is —Y$^2$—PO(OR$^{51}$)$_2$, in which $Y^2$ is a single bond or —CH$_2$— and the other symbols are as hereinbefore defined; and all of $R^2$, $R^3$, $R^4$, $R^5$, $R^6$, $R^7$, $R^8$ and $R^9$ are not hydroxy, amino, or a group including —COOH, hydroxy or amino, that is the compound of the formula (I-4c)

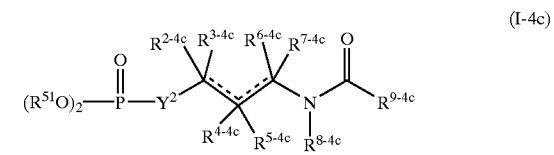
(I-4c)

wherein each of $R^{2-4c}$, $R^{3-4c}$, $R^{4-4c}$, $R^{5-4c}$, $R^{6-4c}$, $R^{7-4c}$, $R^{8-4c}$, $R^{9-4c}$ is the a same meaning as $R^2$, $R^3$, $R^4$, $R^5$, $R^6$, $R^7$, $R^8$, $R^9$, with the proviso that, all of $R^{2-4c}$, $R^{3-4c}$, $R^{4-4c}$, $R^{5-4c}$, $R^{6-4c}$, $R^{7-4c}$, $R^{8-4c}$, $R^{9-4c}$ are not hydroxy, amino or a group including —COOH, hydroxy or amino, and the other symbols are as hereinbefore defined;

may be prepared by reaction of the compound of the formula (X):

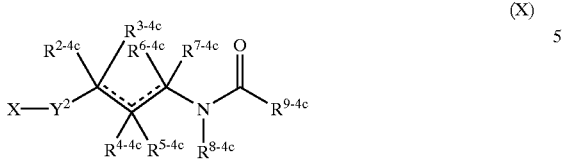

wherein all the symbols are as hereinbefore defined; with the compound of the formula (XI)

$$(R^{511}O)_3P \qquad (XI)$$

or the compound of the formula (XII)

$$(R^{511}O)_2POK \qquad (XII)$$

wherein all the symbols are as hereinbefore defined; when using the compound of the formula (XI) or the compound of the formula (XII) in which $R^{511}$ is protected phosphoric acid, continuously, by deprotection.

The above reaction is known, for example, it maybe carried out in an organic solvent (e.g. tetrahydrofuran, dimethylformamide) at 0–120° C.

The reaction of deprotection of phosphoric acid is known, and it may be carried out by the same method as hereinbefore described.

(d) The compound in which $R^1$ is $-Y^2-PO(OR^{51})_2$, and at least one of $R^2$, $R^3$, $R^4$, $R^5$, $R^6$, $R^7$, $R^8$ and $R^9$ is hydroxy, amino, or a group including —COOH, hydroxy or amino, that is the compound of the formula (I-4d)

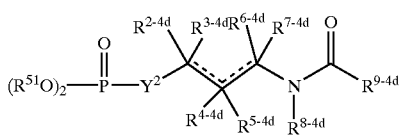

wherein each of $R^{2-4d}$, $R^{3-4d}$, $R^{4-4d}$, $R^{5-4d}$, $R^{6-4d}$, $R^{7-4d}$, $R^{8-4d}$, $R^{9-4d}$ is the a same meaning as $R^2$, $R^3$, $R^4$, $R^5$, $R^6$, $R^7$, $R^8$, $R^9$, with the proviso that, at least one of $R^{2-4d}$, $R^{3-4d}$, $R^{4-4d}$, $R^{5-4d}$, $R^{6-4d}$, $R^{7-4d}$, $R^{8-4d}$, $R^{9-4d}$ is hydroxy, amino, or a group including —COOH, hydroxy or amino, it, and the other symbols are as hereinbefore defined; may be prepared by deprotection under alkaline conditions, deprotection under acidic conditions or hydrogenolysis of the compound of the above formula (I-4c) having protected a group including protected hydroxy, protected amino or a group including protected —COOH, hydroxy or amino, that is the compound of the formula (I-4c1)

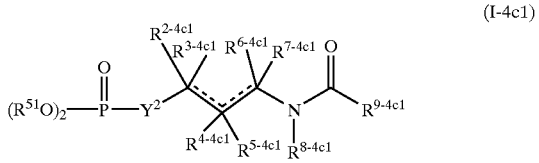

wherein each of $R^{2-4c1}$, $R^{3-4c1}$, $R^{4-4c1}$, $R^{5-4c1}$, $R^{6-4c1}$, $R^{7-4c1}$, $R^{8-4c1}$, $R^{9-4c1}$ is the a same meaning as $R^2$, $R^3$, $R^4$, $R^5$, $R^6$, $R^7$, $R^8$, $R^9$, with the proviso that, at least one of $R^{2-4c1}$, $R^{3-4c1}$, $R^{4-4c1}$, $R^{5-4c1}$, $R^{6-4c1}$, $R^{7-4c1}$, $R^{8-4c1}$, $R^{9-4c1}$ is protected hydroxy, protected amino or a group including protected —COOH (e.g. protected by methyl, ethyl, t-butyl and benzyl), protected hydroxy or protected amino and the other symbols are as hereinbefore defined.

The reactions of deprotection under alkaline conditions, deprotection under acidic conditions and hydrogenolysis are known, and may be carried out by the same method as hereinbefore described.

The reactions of deprotection in the present invention are a common reactions of deprotection as will be apparent to those skilled in the art, for example, deprotection under alkaline conditions, deprotection under acidic conditions or hydrogenolysis. The desired compound of the present invention may be easily prepared using these protecting groups.

As will be apparent to those skilled in the art, methyl, ethyl, t-butyl or benzyl may be used protecting groups for carboxyl, but other groups, which may be removed easily and selectively, are also preferred. For example, the groups described in T. W. Greene, Protective Groups in Organic Synthesis, Wiley, N.Y., 1991, may be used.

Methoxymethyl, tetrahydropyranyl, t-butyldimethylsilyl, acetyl or benzyl may be used protecting groups for hydroxy, but other groups, which may be removed easily and selectively, are also preferred. For example, the groups described in T. W. Greene, Protective Groups in Organic Synthesis, Wiley, N.Y., 1991, may be used.

Benzyloxycarbonyl, t-butoxycarbonyl or trifluoroacetyl may be used as protecting groups for amino, but other groups which may be removed easily and selectively are also preferred. For example, the groups described in T. W. Greene, Protective Groups in Organic Synthesis, Wiley, N.Y., 1991, may be used.

The compounds of the formulae (II), (III), (IV), (V), (VI), (VII), (VIII), (IX), (X) , (XI), (XII), (XIII) and (XIV) are known per se or may be prepared by known methods.

In each reaction in the present specification, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Pharmacological Activities]

The potency of inhibitory activity against each matrix metalloproteinases of the compound of the formula (I) was confirmed as below.

(1) Inhibitory Activity Against Gelatinase A

Method

The progelatinase A (5 µl; in assay buffer (40 µl)) was purified from human normal skin dermal fibroblasts (HNDF). It was activated by adding thereto 10 mM of p-aminophenylmercuric acetate (APMA) (5 µl) and preincubating for 1 hour at 37° C.

A mixture of the synthetic substrate (MOCAc-Pro-Leu-Gly-A2pr(Dnp)-Ala-Arg-NH$_2$) (130 µl; a final concentration 13.5 µM) and a solution (20 µl) with or without various concentrations of the test compound was preincubated for 5 minutes at 37° C.

The solution of activated gelatinase A (50 µl/well) was mixed with the mixture and the mixture was incubated for 15 minutes at 37° C. The enzyme reaction was started. The enzyme activity was represented by increasing value of fluorescent intensity [Ex=325 nm (Ex)/393 nm (Em)] per 1 minute. Inhibitory activity was represented by inhibitory percentage (%) per enzyme activity without the test compound.

The result was showed in Table 26.

TABLE 26

| Example No. | IC$_{50}$ ($\mu$M) |
|---|---|
| 8(6) | 0.0017 |
| 16(2) | 0.0042 |

(2) Inhibitory Activity Against Collagenase
Method

The procollagenase (5 $\mu$l; in assay buffer (105 $\mu$l)) was purified from human normal skin dermal fibroblasts (HNDF). It was activated by adding thereto 1 mg/ml Trypsin (45 $\mu$l) and preincubating for 1 minute at 37° C. Trypsin was inactivated by addition of 5 mg/ml soybean trypsin inhibitor (SBTI; 50 $\mu$l).

A mixture of the synthetic substrate (Ac-Pro-Leu-Gly-[2-mercapto-4-methyl-pentanoyl]-Leu-Gly-OEt) (105 $\mu$l; a final concentration 1.33 mM) and a solution (20 $\mu$l) with or without various concentrations of the test compound was preincubated for 5 minutes at 26° C.

The solution of activated enzyme (75 $\mu$l /tube, 50 $\mu$l) was mixed with the mixture and the mixture was incubated for 10 minutes at 26° C.

Absorption at 324 nm was measured 40 points in the course of 10 minutes. Vmax value was determined as measured value in 30 points therein.

The result was showed in Table 27.

TABLE 27

| Example No. | IC$_{50}$ ($\mu$M) |
|---|---|
| 8 | 0.014 |
| 20(3) | 0.0068 |
| 21(2) | 0.0076 |

(3) Inhibitory Activity Against Stromelysin
Method

The mixture of human stromelysin (Yagai; 9 volume) and 10 mM p-aminophenylmercury acetate (1 volume) was activated for 20 hours at 37° C. A solution of the test compound in dimethylsulfoxide (10 $\mu$l) and 0.5 mM solution (10 $\mu$l) of 10 mM solution of the synthetic substrate NFF-3 (Mca-Arg-Pro-Lys-Pro-Val-Glu-Nva-Trp-Arg-Lys(DNP)-NH$_2$., Nva: norvaline, Peptide Laboratory) in dimethylsulfoxide diluted by water were added to assay buffer (50 mM tris-HCl, 10 mM CaCl$_2$, 0.05% Brij35, 0.02% NaN$_3$ (pH7.5)) (150 $\mu$l). Furthermore, assay buffer (30 $\mu$l) was added to the mixture. The mixture was incubated for 10 minutes at 37° C. The reaction was started by addition of a solution of the above activated stromelysin solution (50 $\mu$l). The enzyme activity was represented by increasing value of fluorescent intensity [Ex=325 nm (Ex)/393 nm (Em)] per 1 minute. Inhibitory activity was represented by inhibitory percentage (%) per enzyme activity without the test compound.

The result was showed in Table 28.

TABLE 28

| Example No. | IC$_{50}$ ($\mu$M) |
|---|---|
| 8(6) | 0.029 |
| 8(7) | 0.040 |

[Toxicity]

The toxicity of the compounds of the present invention is very low and therefore, the compounds may be considered safe for pharmaceutical use.

[Application for Pharmaceuticals]

Inhibition of matrix metalloproteinase, for example, gelatinase, stromelysin or collagenase, is useful for prevention and/or treatment of diseases, for example, rheumatoid diseases, arthrosteitis, osteoarthritis, unusual bone resorption, osteoporosis, periodontitis, interstitial nephritis, arteriosclerosis, pulmonary emphysema, cirrhosis, cornea injury, cornea ulcer, metastasis, invasion or growth of tumor cells, autoimmune disease (Crohn's disease, Sjogren's syndrome), disease caused by vascular emigration or infiltration of leukocytes, arterialization, multiple sclerosis, aorta aneurysm, endometriosis, restenosis after PTCA, unstable angina, acute myocardial infarction, transient ischemic attack in animals including human beings, especially human beings.

For the purpose above described, the compounds of formulae (I) of the present invention and non-toxic salts, acid addition salts or hydrates may be normally by administered systemically or locally usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound (s) maybe admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof.

Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. No. 2,868,691 or U.S. Pat. No. 3,095,355 may be used.

BEST MODE FOR CARRYING OUT THE INVENTION

The following reference examples and examples illustrate the present invention, but do not limit the present invention.

The solvents in the parenthesis show the developing or eluting solvents and the ratios of the solvents used are by volume in chromatographic separations or TLC.

The solvents in the parentheses in NMR show the solvents used in measurement.

Reference Example 1

4(S)-[4-(N-benzyloxycarbonylamino)-5-hydroxy]pentanoic acid methyl ester

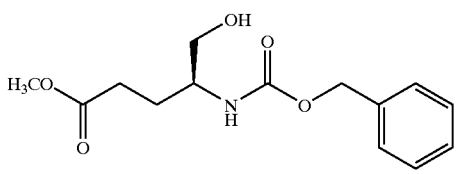

To a solution of 4(S)-carboxy-4-(N-benzyloxycarbonylamino)butanoic acid methyl ester (600 g) and N-hydroxyphtalimide (234 g) in tetrahydrofuran (2.5 L) in the ice-bath, dicyclohexylcarbodiimide (419 g) was added over 1 hour. Ice-bath was removed and the solution was stirred for 2 hours. To the reaction mixture, acetic acetate was added. The mixed solution was filtered, and the filtrate was concentrated. The obtained solid was wash with ethyl acetate/hexane (1:9). The obtained solid was dissolved into tetrahydrofuran (8 L), and in the ice-bath, sodium borohydride (50 g) was added, and then tetrahydrofuran/water (1:1, 184 ml) was added over 4 hours. 2N hydrochloric acid was added to the reaction mixture, and the solution was extracted with ethyl acetate. The extract was washed with an aqueous solution of sodium bicarbonate and a saturated aqueous solution of sodium chloride, dried over anhydrous magnesium sulfate and concentrated. The obtained solid was washed with ethyl acetate/hexane (1:9) to give the title compound (240 g) having the following physical data.

TLC: Rf 0.40 (ethyl acetate:hexane=9:1).

Reference Example 2

4(S)-[5-ethoxymethoxy-4-(N-benzyloxycarbonylamino)]pentanoic acid methyl ester

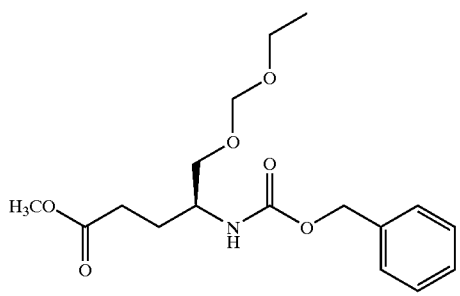

To a solution of the compound prepared in Reference example 1 (320 g) in methylene chloride (700 ml) in the ice-bath, diisopropylethylamine (596 ml) was added. Ethoxymethyl chloride (209 ml) was added to the mixture over 1 hour. Ice-bath was removed, and then the solution was stirred for 2 hours. Ether was added to the reaction mixture. The solution was washed with water, 1N hydrochloric acid and a saturated aqueous solution of sodium chloride, dried over anhydrous sodium sulfate, and concentrated. The residue was washed with ethyl acetate/hexane (1:9) to give the title compound (358 g) having the following physical data.

TLC: Rf 0.60 (ethyl acetate:hexane=8:2).

Reference Example 3

4(S)-(5-ethoxymethoxy-4-amino)pentanoic acid methyl ester

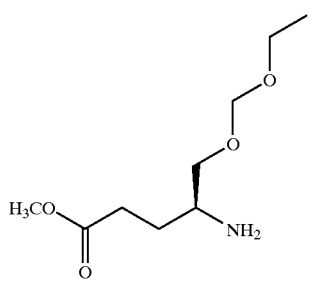

To a solution of the compound prepared in Reference example 2 (5.0 g) in methanol (30 ml), 10% palladium carbon (wet) was added under an atmosphere of argon. The mixture was stirred for 50 minutes under an atmosphere of hydrogen gas. The reaction mixture was filtered, and the filtrate was concentrated to give the title compound having the following physical data.

TLC: Rf 0.32 (chloroform:methanol=9:1).

EXAMPLE 1

5-ethoxymethoxy-4(S)-[N-(4-iodophenylcarbonyl) amino]pentanoic acid methyl ester

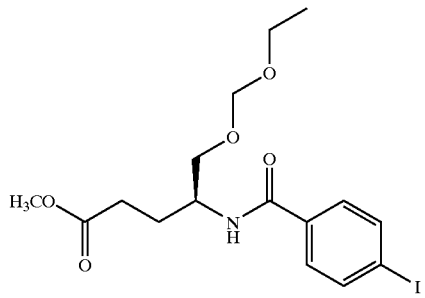

To a solution of the compound prepared in Reference example 3 in methylene chloride (30 ml), triethylamine (2.1 ml) and 4-iodobenzoly chloride (3.54 g) was added under an atmosphere of argon. The mixture was stirred for 20 minutes. The reaction mixture was extracted with ethyl acetate. The extract was dried over anhydrous magnesium sulfate and concentrated. The residue was recrystallized from hexane/ethyl acetate (3:2) to give the title compound (3.88 g) having the following physical data.

TLC: Rf 0.21 (hexane:ethyl acetate=2:1);

NMR (CDCl$_3$): δ7.79(2H, d, J=8.6 Hz), 7.52(2H, d, J=8.6 Hz), 6.74(1H, d, J=8.7 Hz), 4.71(1H, d, J=6.6 Hz), 4.68(1H, d, J=6.6 Hz), 4.36–4.25(1H, m), 3.80–3.55(7H, m), 2.56–2.36(2H, m), 2.12–1.93(2H, m), 1.21(3H, t, J=7.1 Hz).

EXAMPLE 2

5-ethoxymethoxy-4(S)-[N-(4-iodophenylcarbonyl) amino]pentanoic acid

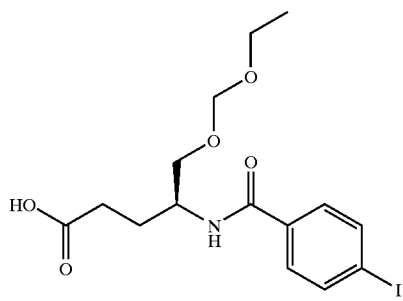

To a solution of the compound prepared in Example 1 (3.37 g) in THF/methanol (20 ml/30 ml), 1N aqueous solution of sodium hydroxide (9 ml) was added. The mixture was stirred for 2 hours. The reaction mixture was neutralized by adding 1N aqueous solution of hydrochloric acid and extracted with ethyl acetate. The solution was 5% aqueous solution of citric acid and a saturated aqueous solution of sodium chloride. The organic layer was dried over anhydrous magnesium sulfate and concentrated to give the title compound (2.82 g) having the following physical data.

NMR (d$_6$-DMSO): δ12.06(1H, brs), 8.23(1H, d, J=8.4 Hz), 7.84(2H, d, J=8.6 Hz), 7.62(2H, d, J=8.6 Hz), 4.59(2H, s), 4.16–4.05(1H, m), 3.54–3.45(4H, m), 2.29–2.20(2H, m), 1.92–1.80(1H, m), 1.77–1.63(1H, m), 1.08(3H, t, J=7.4 Hz).

EXAMPLE 3

5-ethoxymethoxy-4(S)-[N-(4-iodophenylcarbonyl) amino]pentanoic acid allyl ester

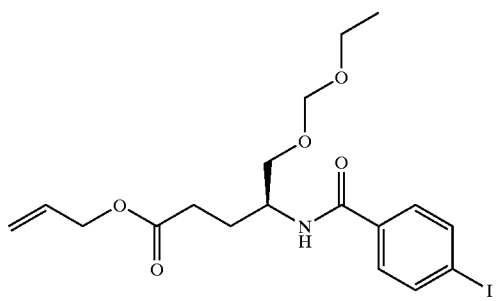

To a solution of the compound prepared in Example 2 (4.11 g) in dimethylformamide (DMF; 20 ml), potassium carbonate (1.62 g), sodium iodide (small amount) and allyl bromide (5 ml) were added. The mixture was vigorously stirred overnight. The reaction mixture was extracted with ethyl acetate, dried over anhydrous magnesium sulfate and concentrated. The residue was washed with hexane to give the title compound having the following physical data.

NMR (CDCl$_3$): δ7.78(2H, d, J=8.4 Hz), 7.52(2H, d, J=8.4 Hz), 6.74(1H, d, J=8.7 Hz), 5.92–5.78(1H, m), 5.32–5.16 (2H, m), 4.71(1H, d, J=6.9 Hz), 4.68(1H, d, J=6.9 Hz), 4.60–4.47(2H, m), 4.36–4.25(1H, m), 3.75(1H, dd, J=10.2 Hz, 3.0 Hz), 3.66–3.56(3H, m), 2.60–2.49(2H, m), 2.16–1.93(2H, m), 1.20(3H, t, J=7.2 Hz).

EXAMPLE 3(1)

5-ethoxymethoxy-4(S)-[N-(4-nitrophenylcarbonyl) amino]pentanoic acid allyl ester

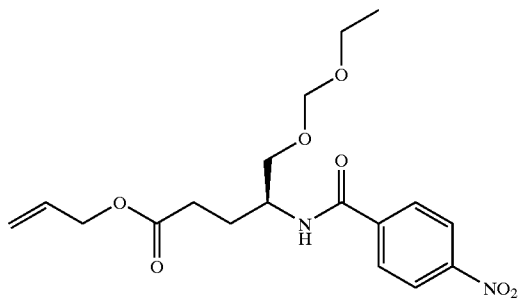

The title compounds having the following physical data was obtained by the same procedure as a series of reaction of Example 1→Example 2→Example 3, using 4-nitrobenzoyl chloride in stead of 4-iodobenzoyl chloride.

TLC: Rf 0.50 (toluene:ethyl acetate=1:1).

EXAMPLE 4

5-ethoxymethoxy-4(S)-[N-(4-cyanophenylcarbonyl)amino]pentanoic acid allyl ester

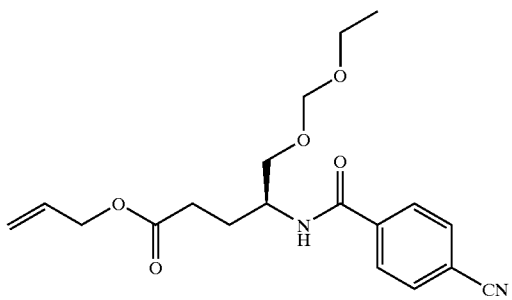

To a solution of the compound prepared in Example 3 (2.00 g) in DMF (40 ml), copper cyanide (520 mg) was added. The mixture was vigorously stirred for 3 hours at 50° C. The reaction mixture was cooled, and diluted with ethyl acetate and water. The solution was filtered, the filtrate was extracted with ethyl acetate. The organic layer was washed with a saturated aqueous solution of sodium chloride, dried over anhydrous magnesium sulfate and concentrated to give the title compound (1.12 g) having the following physical data.

NMR (300 MHz, CDCl$_3$): $\delta$7.90(2H, d, J=8.1 Hz), 7.74 (2H, d, J=8.1 Hz), 6.96(1H, d, J=8.4 Hz), 5.92–5.79(1H, m), 5.32–5.16(2H, m), 4.72(1H, d, J=6.7 Hz), 4.68(1H, d, J=6.7 Hz), 4.57–4.51(2H, m), 4.37–4.27(1H, m), 3.79(1H, dd, J=10.1 Hz, 3.1 Hz), 3.67–3.57(3H, m), 2.62–2.41(2H, m), 2.16–1.97(2H, m), 1.20(3H, t, J=7.0 Hz).

EXAMPLE 5

5-ethoxymethoxy-4(S)-[N-(4-cyanophenylcarbonyl)amino]-2(R)-methoxymethylpentanoic acid allyl ester

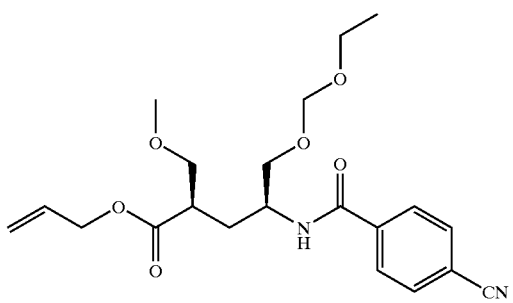

To a solution of the compound prepared in Example 4 (1.87 g) and 1,3-dimethyl-2-imidazolidinone (1.7 ml) in tetrahydrofuran (THF; 20 ml), 1M lithium bis(trimethylsilyl)amide (11.4 ml; in THF) was dropped at −78° C., and then the mixture was stirred for 30 minutes at same temperature. Methoxymethyl chloride (1.2 ml) was added to the reaction mixture, and the mixture was stirred for 3 hours. The reaction mixture was diluted with a saturated aqueous solution of ammonium chloride, and warmed to room temperature, and then the solution was extracted with ethyl acetate. The extract was dried over anhydrous magnesium sulfate and concentrated. The residue was purified by column chromatography (toluene:ethyl acetate=2:1) to give the title compound (1.45 g) having the following physical data.

NMR (200 MHz, CDCl$_3$): $\delta$7.89(2H, d, J=8.8 Hz), 7.73 (2H, d, J=8.8 Hz), 6.82(1H, d, J=8.8 Hz), 5.90–5.71(1H, m), 5.29–5.11(2H, m), 4.76–4.66(2H, m), 4.63–4.28(3H, m), 3.82–3.74(1H, m), 3.69–3.54(5H, m), 3.34(3H, s), 2.86–2.72(1H, m), 2.33–2.12(1H, m), 2.00–1.86(1H, m), 1.20(3H, t, J=7.2 Hz).

EXAMPLE 6

5-ethoxymethoxy-4(S)-[N-(4-cyanophenylcarbonyl)amino]-2(R)-methoxymethylpentanoic acid

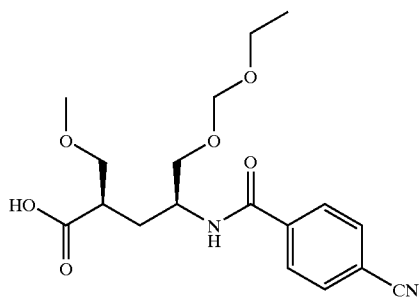

To the solution of the compound prepared in Example 5 (1.45 g) and morpholine (0.38 ml) in THF (3.6 ml), tetrakis(triphenylphosphine) palladium(0) (20 mg) was added, and the mixture was stirred for 3 hours at room temperature. The reaction mixture was diluted with ethyl acetate, and washed with 1N aqueous solution of hydrochloride and a saturated aqueous solution of sodium chloride. The organic layer was dried over anhydrous magnesium sulfate and concentrated to give the title compound (1.33 g) having the following physical data.

NMR (300 MHz, d$_6$-DMSO): $\delta$12.19(s, 1H), 8.47(d, J=8.4 Hz, 2H), 8.00–7.92(m, 3H), 4.59(s, 2H), 4.24–4.11(m, 1H), 3.54–3.41(m, 6H), 3.20(s, 3H), 2.59–2.46(m, 1H), 1.78(t, J=7.2 Hz, 2H), 1.08(t, J=7.0 Hz, 3H).

EXAMPLE 6(1)~6(13)

The following compounds were obtained by the same procedure as a series of reaction of Reference example 1→Reference example 2→Reference example 3→Example 1→Example 2→Example 3 (→Example 4)→Example 5→Example 6, using a corresponding compound, for example, using 4(R)-carboxy-4-(N-benzyloxycarbonylamino)butanoic acid methyl ester instead of 4(S)-carboxy-4-(N-benzyloxycarbonylamino)butanoic acid methyl ester in the Reference example 1, using a corresponding halogen compound instead of ethoxy chloride in Reference example 2, using a corresponding acyl chloride instead of 4-iodobenzoyl chloride in the Example 1, using a corresponding halogen compound instead of methoxymethyl chloride in the Example 5.

EXAMPLE 6(1)

2(R)-ethoxymethyl-5-ethoxymethoxy-4(S)-[N-(4-nitrophenylcarbonyl)amino]pentanoic acid

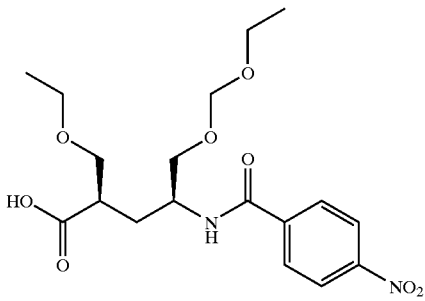

TLC: Rf 0.36 (chloroform:methanol=9:1)

NMR (300MHz, CDCl$_3$): δ8.27(d, J=9.0 Hz, 2H), 7.96(d, J=9.0 Hz, 2H), 7.09(d, J=9.0 Hz, 1H), 4.72(d, J=6.9 Hz, 1H), 4.68(d, J=6.9 Hz, 1H), 4.43–4.32(m, 1H), 3.80(dd, J=10.5, 3.3 Hz, 1H), 3.70–3.50(m, 7H), 2.81–2.71(m, 1H), 2.18 (ddd, J=14.1, 10.2, 7.5 Hz, 1H), 1.87(dt, J=14.1, 4.8 Hz, 1H), 1.21(t, J=6.6 Hz, 3H), 1.20(t, J=7.2 Hz, 3H).

EXAMPLE 6(2)

5-ethoxymethoxy-2(S)-(3-thienylmethyl)-4(S)-[N-(4-nitrophenylcarbonyl)amino]pentanoic acid

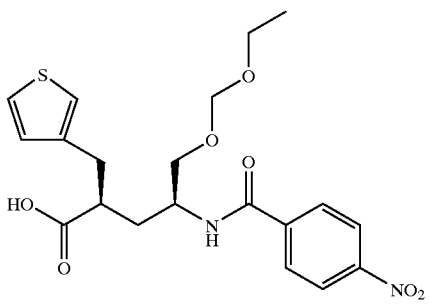

TLC: Rf 0.43 (chloroform:methanol=9:1);

NMR (300MHz, CDCl$_3$): δ8.25(d, J=8.7 Hz, 2H), 7.94(d, J=8.7 Hz, 2H), 7.25(dd, J=5.1, 3.3 Hz, 1H), 7.03–6.92(m, 3H), 4.71(d, J=6.9 Hz, 1H), 4.64(d, J=6.9 Hz, 1H), 4.46–4.34(m, 1H), 3.77(dd, J=10.5, 3.3 Hz, 1H), 3.64–3.49 (m, 3H), 3.04(dd, J=15.0, 6.9 Hz, 1H), 2.92(dd, J=15.0, 6.9 Hz, 1H), 2.83–2.72(m, 1H), 2.10(dt, J=14.1, 9.0 Hz, 1H), 1.81(dt, J=14.1, 5.4 Hz, 1H), 1.19(t, J=7.2 Hz, 3H).

EXAMPLE 6(3)

5-ethoxymethoxy-2(S)-(3-furylmethyl)-4(S)-[N-(4-nitrophenylcarbonyl)amino]pentanoic acid

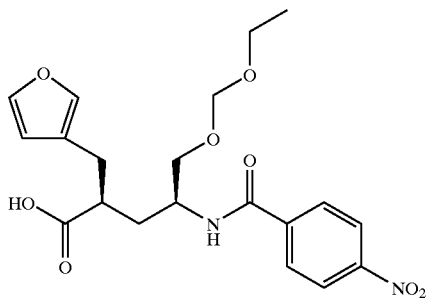

TLC: Rf 0.43 (chloroform:methanol=9:1);

NMR (200 MHz, CDCl$_3$): δ8.19 (d, J=8.8 Hz, 2H), 7.91(d, J=8.8 Hz, 2H), 7.30–7.18(m, 3H), 6.23(m, 1H), 4.68(d, J=d, J=7.0 Hz, 1H), 4.61(d, J=7.0 Hz, 1H), 4.40–4.20 (m, 1H), 3.80(dd, J=10.2, 3.0 Hz, 1H), 3.62–3.42(m, 3H), 3.00–2.50(m, 3H), 2.12–1.92(m, 1H), 1.84–1.68(m, 1H), 1.16(t, J=7.0 Hz, 3H).

EXAMPLE 6(4)

2(S)-benzyl-5-pivaloyloxy-4(S)-[N-(4-nitrophenylcarbonyl)amino]pentanoic acid

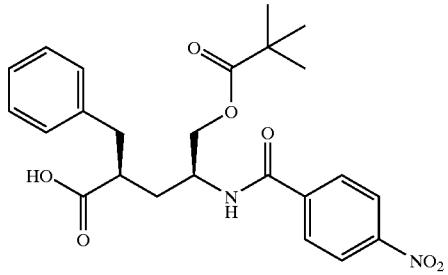

TLC: Rf 0.54 (chloroform:methanol=9:1);

NMR (300 MHz, d$_6$-DMSO): δ10.39(s, 1H), 8.70(d, J=1.8 Hz), 8.54(d, J=8.7 Hz), 8.31(d, J=9.0 Hz), 8.03(d, J=9.0 Hz), 7.25–7.11(m, 5H), 4.38–4.25(m, 1H), 4.10(dd, J=10.8, 4.5 Hz), 4.00(dd, J=10.8, 4.5 Hz), 2.82–2.66(m, 2H), 2.42–2.33(m, 1H), 1.72–1.68(m, 2H), 1.03(s, 9H).

EXAMPLE 6(5)

5-acetyloxy-2(S)-benzyl-4(s)-[N-(4-nitrophenylcarbonyl)amino]pentanoic acid

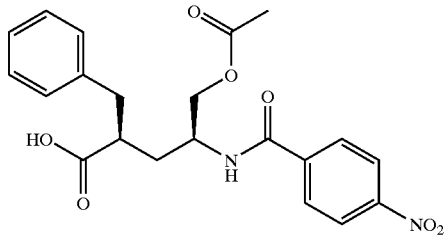

TLC: Rf 0.42 (chloroform:methanol=9:1);
NMR (300 MHz, d$_6$-DMSO): δ8.21–8.18(m, 2H), 7.91–7.87(m, 2H), 7.30–7.16(m, 5H), 6.71(d, J=8.4 Hz), 4.50–4.40(m, 1H), 4.23(dd, J=11.4, 5.4 Hz), 4.12(dd, J=11.4, 5.4 Hz), 3.10–3.01(m, 1H), 2.88–2.78(m, 3H), 2.06–1.95(m, 1H), 1.99(3, 3H), 1.77–1.69(m, 1H).

EXAMPLE 6(6)

5-ethoxymethoxy-2 (R)-methoxymethyl-4(S)-[N-(4-phenoxyphenylcarbonyl)amino]pentanoic acid,

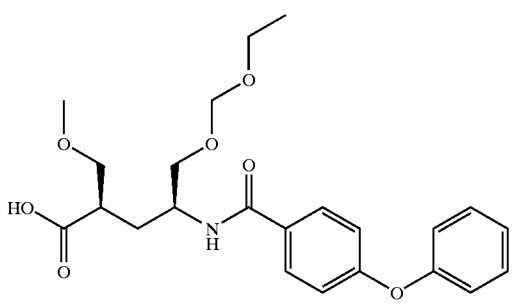

TLC: Rf 0.44 (chloroform:methanol=9:1);

NMR (200 MHz, CDCl₃): δ7.75(d, J=8.8 Hz, 2H), 7.42–7.32(m, 2H), 7.21–7.13(m, 1H), 7.07–6.99(m, 2H), 6.98(d, J=8.8 Hz, 2H), 6.73(d, J=8.8 Hz, 1H), 4.70(d, J=6.6 Hz, 1H), 4.68(d, J=6.6 Hz, 1H), 4.46–4.30(m, 1H), 3.76(dd, J=10.2, 3.2 Hz, 1H), 3.70–3.52(m, 5H), 3.39(s, 3H), 2.83–2.69(m, 1H), 2.17(ddd, J=14.4, 10.2, 7.0 Hz, 1H), 1.87(ddd, J=14.4, 6.2, 4.8 Hz, 1H), 1.21(t, J=7.0 Hz, 3H).

EXAMPLE 6(7)

5-ethoxymethoxy-2(R)-methoxymethyl-4(S)-[N-(4-(2-furyl)phenylcarbonyl)amino]pentanoic acid

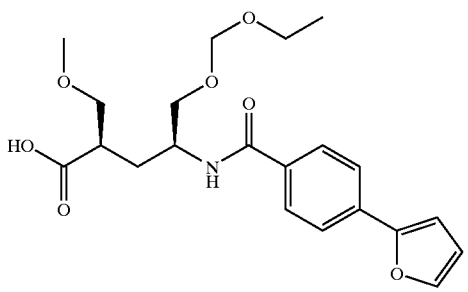

TLC: Rf 0.21 (chloroform:methanol=10:1);

NMR (CDCl₃): δ7.78(2H, d, J=8.5 Hz), 7.68(2H, d, J=8.5 Hz), 7.49(1H, d, J=1.7 Hz), 6.80(1H, d, J=8.8 Hz), 6.73(1H, d, J=3.3 Hz), 6.49(1H, dd, J=1.7, 3.3 Hz), 4.71(1H, d, J=6.6 Hz), 4.68(1H, d, J=6.6 Hz), 4.4(1H, m), 3.71(1H, dd, J=3.3, 10.2 Hz), 3.7–3.55(5H, m), 3.38(3H, s), 2.89(1H, m), 2.17(1H, m), 1.88(1H, m), 1.20(3H, t, J=7.1 Hz).

EXAMPLE 6(8)

5-ethoxymethoxy-4(S)-[N-(4-cyanophenylcarbonyl)amino]-2(R)-ethoxymethylpentanoic acid

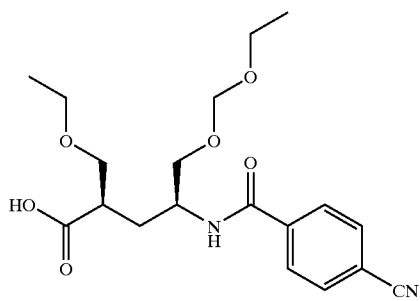

TLC: Rf 0.45 (chloroform:methanol=9:1).

EXAMPLE 6(9)

5-ethoxymethoxy-2(S)-methoxymethyl-4(R)-[N-(4-nitrophenylcarbonyl)amino]pentanoic acid

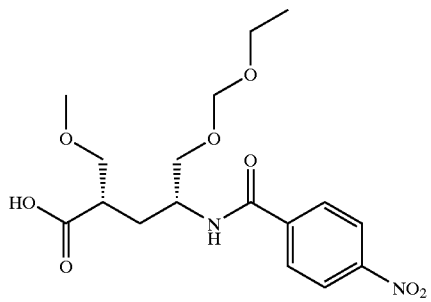

TLC: Rf 0.36 (chloroform:methanol=9:1);

NMR (200 MHz, CDCl₃): δ8.26(d, J=8.6 Hz, 2H), 7.95(d, J=8.6 Hz, 2H), 7.05(d, J=8.8 Hz, 1H), 4.72(d, J=6.6 Hz, 1H), 4.68(d, J=6.6 Hz, 1H), 4.48–4.30(m, 1H), 3.80(dd, J=10.2, 3.2 Hz, 1H), 3.69–3.53(m, 5H), 3.38(s, 3H), 2.83–2.68(m, 1H), 2.16(ddd, J=14.4, 10.0, 7.8 Hz, 1H), 1.87(dt, J=14.4, 5.0 Hz, 1H), 1.20(t, J=7.4 Hz, 3H).

EXAMPLE 6(10)

5-ethoxymethoxy-2(S)-methoxymethyl-4(R)-[N-(4-chlorophenylcarbonyl)aminolpentanoic acid

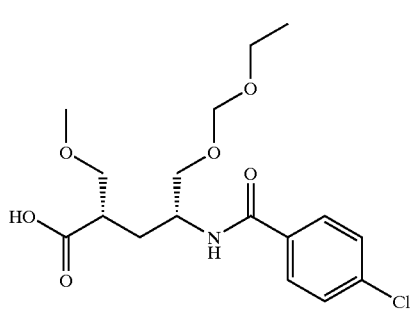

TLC: Rf 0.38 (chloroform:methanol=9:1);
NMR (200 MHz, CDCl₃): δ7.71(d, J=8.8 Hz, 2H), 7.37(d, J=8.8 Hz, 2H), 6.83(d, J=8.7 Hz, 1H), 4.70(d, J=7.0 Hz, 1H), 4.68(d, J=7.0 Hz, 1H), 4.45–4.28(m, 1H), 3.76(dd, J=10.2, 3.2 Hz, 1H), 3.68–3.52(m, 5H), 3.37(s, 3H), 2.82–2.68(m, 1H), 2.13(ddd, J=14.4, 10.0, 7.8 Hz, 1H), 1.87(dt, J=14.4, 5.4 Hz, 1H), 1.19(t, J=6.8 Hz, 3H).

EXAMPLE 6(11)

5-ethoxymethoxy-2(S)-methoxymethyl-4(R)-[N-(4-bromophenylcarbonyl)amino]pentanoic acid

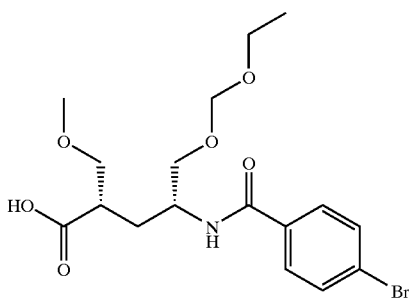

TLC: Rf 0.39 (chloroform:methanol=9:1);

NMR (CD$_3$OD): δ7.73–7.69(m, 2H), 7.65–7.59(m, 2H), 4.67(s, 2H), 4.37–4.28(m, 1H), 3.63–3.53(m, 6H), 3.32(s, 3H), 2.75–2.64(m, 1H), 1.96–1.89(m, 2H), 1.15(t, J=7.2 Hz, 3H).

EXAMPLE 6(12)

5-ethoxymethoxy-2(S)-methoxymethyl-4(R)-[N-(4-cyanophenylcarbonyl)amino]pentanoic acid

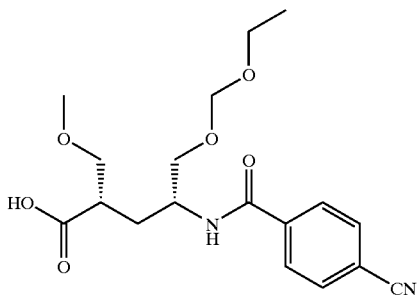

NMR (300 MHz, d$_6$-DMSO): δ12.19(1H, s), 8.47(2H, d, J=8.4 Hz), 8.00–7.92(3H, m), 4.59(2H, s), 4.24–4.11(1H, m), 3.54–3.41(6H, m), 3.20(3H, s), 2.59–2.46(1H, m), 1.78 (2H, t, J=7.2 Hz), 1.08(3H, t, J=7.0 Hz).

EXAMPLE 6(13)

5-ethoxymethoxy-2(S)-benzyl-4(S)-[N-(4-chlorocyclohexylcarbonyl)amino]pentanoic acid

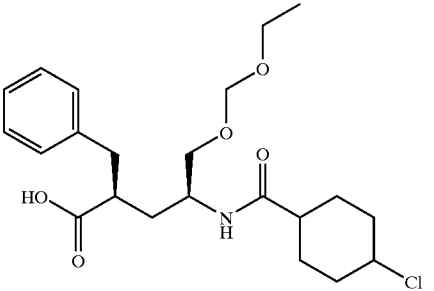

TLC: Rf 0.45 (chloroform:methanol=9:1).

EXAMPLE 7

N-(1-methoxy-1,1-dimethylmethyl)oxy-5-ethoxymethoxy-2(R)-methoxymethyl-4(S)-[N-(4-cyanophenylcarbonyl)amino]pentanamide

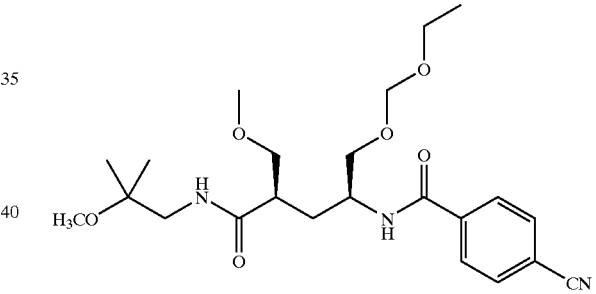

To a solution of the compound prepared in Example 6 (1.32 g) in DMF (15 ml), 1-ethyl-(3-(3-dimethylamino)propyl)-carbodiimide hydrochloride (1.39 g), 1-hydroxybenzotriazole (1.15 g) and N-(1-methoxy-1,1-dimethyloxy)amine (0.8 ml) were added. The mixture was stirred for 2.5 hours at room temperature. The reaction mixture was extracted with ethyl acetate. The extract was dried over anhydrous magnesium sulfate and concentrated to give the title compound having the following physical data.

TLC: Rf 0.31 (chloroform:methanol=19:1);

NMR (300 MHz, d$_6$-DMSO): δ8.71(s, 1H), 7.94(d, J=8.1 Hz, 2H), 7.15 (d, J=8.4 Hz, 1H), 7.02 (d, J=8.1 Hz, 2H), 4.69(d, J=6.9 Hz, 1H), 4.66(d, J=6.9 Hz, 1H), 4.36–4.22(m, 1H), 3.74(dd, J=10.2, 3.6 Hz, 1H), 3.65–3.48(m, 5H), 3.39 (s, 3H), 3.22(s, 3H), 3.58–2.47(m, 1H), 2.23(ddd, J=14.4, 11.1, 8.4 Hz, 1H), 1.78(dt, J=14.4, 3.9 Hz, 1H), 1.37(s, 3H), 1.26(s, 3H), 1.19(t, J=7.2 Hz, 3H).

EXAMPLE 8

N-hydroxy-5-ethoxymethoxy-2(R)-methoxymethyl-4(S)-[N-(4-cyanophenylcarbonyl)amino]pentanamide

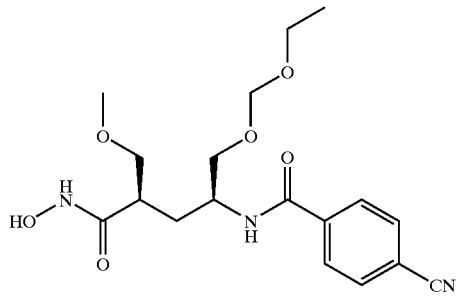

To a solution of the compound prepared in Example 7 in methanol, 1N aqueous solution of hydrochloric acid (10 drops) was added. The mixture was stirred for 5 minutes at room temperature. The reaction mixture was extracted with ethyl acetate/toluene, and the extract was concentrated. The residue was recrystallized from isopropyl ether/methanol to give the title compound (540 mg) having the following physical data.

TLC: Rf 0.38 (chloroform:methanol=9:1);

NMR (300 MHz, $d_6$-DMSO): $\delta$10.44(1H, s), 8.75(1H, s), 8.40(1H, d, J=8.7 Hz), 7.97(2H, d, J=8.8 Hz), 7.95(2H, d, J=8.8 Hz), 4.58(2H, s), 4.16–4.03(1H, m), 3.54–3.28(6H, m), 3.17(3H, s), 2.44–2.33(1H, m), 1.80–1.69(1H, m), 1.68–1.55(1H, m), 1.07(3H, t, J=7.1 Hz).

EXAMPLE 8(1)~8(13)

The following compounds were obtained by the same procedure as a series of reaction of Example 7→Example 8, using the compound prepared in Example 6(1)~6(13).

EXAMPLE 8(1)

N-hydroxy-2(R)-ethoxymethyl-5-ethoxymethoxy-4(S)-[N-(4-nitrophenylcarbonyl)amino]pentanamide

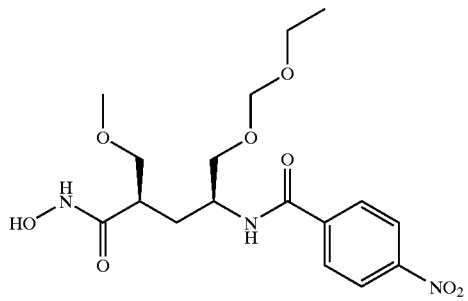

TLC: Rf 0.29 (chloroform:methanol=19:1);

NMR (200 MHz, $d_6$-DMSO): $\delta$10.45(s, 1H), 8.75(s, 1H), 8.49(d, J=8.4 Hz, 1H), 8.30(d, J=8.8 Hz, 2H), 8.06(d, J=8.8 Hz, 2H), 4.59(s, 2H), 4.21–4.00(m, 1H), 3.60–3.28(m, 8H), 2.43–2.26(m, 1H), 1.86–1.50(m, 2H), 1.08(t, J=7.0 Hz, 3H), 1.05(t, J=7.0 Hz, 3H).

EXAMPLE 8(2)

N-hydroxy-5-ethoxymethoxy-2(S)-(3-thienylmethyl)-4(S)-[N-(4-nitrophenylcarbonyl)amino]pentanamide

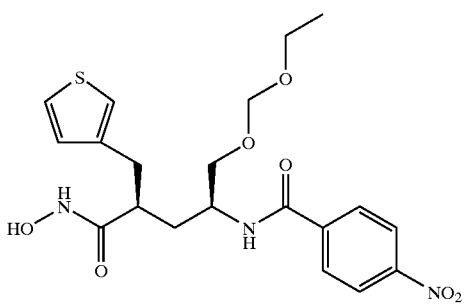

TLC: Rf 0.43 (chloroform:methanol=9:1);

NMR (300 MHz, $d_6$-DMSO): $\delta$10.42(s, 1H), 8.72(s, 1H), 8.50(d, J=8.4 Hz, 1H), 8.30(d, J=8.7 Hz, 2H), 8.07(d, J=8.7 Hz, 2H), 7.39(dd, J=5.1, 3.9 Hz, 1H), 7.07(m, 1H), 6.89(dd, J=5.1, 1.2 Hz, 1H), 4.58(s, 2H), 4.28–4.13(m, 1H), 3.51(d, J=5.7 Hz, 2H), 3.45(q, J=7.2 Hz, 2H), 2.85–2.68(m, 2H), 2.42–2.28(m, 1H), 1.83–1.60(m, 2H), 1.08(t, J=7.2 Hz, 3H).

EXAMPLE 8(3)

N-hydroxy-5-ethoxymethoxy-2(S)-(3-furylmethyl)-4(S)-[N-(4-nitrophenylcarbonyl)amino]pentanamide

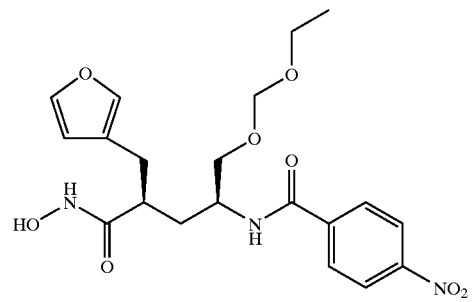

TLC: Rf 0.43 (chloroform:methanol=9:1);

NMR (200 MHz, $d_6$-DMSO): $\delta$10.45(brs, 1H), 8.75(brs, 1H), 8.51(d, J=8.0 Hz, 1H), 8.29(d, J=8.8 Hz, 2H), 8.07(d, J=8.8 Hz, 2H), 7.51(m, 1H), 7.35(m, 1H), 6.28(m, 1H), 4.59(s, 2H), 4.30–4.04(m, 1H), 3.62–3.38(m, 4H), 2.70–2.45(m, 2H), 2.40–2.20(m, 1H), 1.90–1.58(m, 2H), 1.07(t, J=7.0 Hz, 3H).

EXAMPLE 8(4)

N-hydroxy-2(S)-benzyl-5-pivaloyloxy-4(S)-[N-(4-nitrophenylcarbonyl)amino]pentanamide

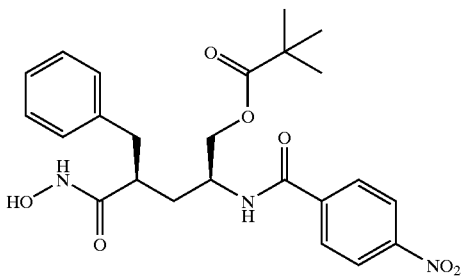

TLC: Rf 0.54 (chloroform:methanol=9:1);

NMR (300 MHz, $d_6$-DMSO): δ10.39(s, 1H), 8.70(d, J=1.8 Hz, 1H), 8.54(d, J=8.7 Hz, 1H), 8.31(d, J=9.0 Hz, 2H), 8.03(d, J=9.0 Hz, 2H), 7.25–7.11(m, 5H), 4.38–4.25(m, 1H), 4.10(dd, J=10.8 Hz, 4.5 Hz, 1H), 4.00(dd, J=10.8, 7.5 Hz, 1H), 2.82–2.66(m, 2H), 2.42–2.33(m, 1H), 1.72–1.68(m, 2H), 1.03(s, 9H).

EXAMPLE 8(5)

N-hydroxy-5-acetyloxy-2(S)-benzyl-4(S)-[N-(4-nitrophenylcarbonyl)amino]pentanamide

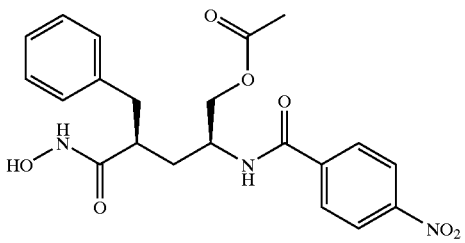

TLC: Rf 0.62 (chloroform:methanol=9:1);

NMR (300 MHz, $d_6$-DMSO): δ10.38(s, 1H), 8.65(brs, 1H), 8.57(d, J=8.4 Hz, 1H), 8.32–8.28(m, 2H), 8.07–8.03(m, 2H), 7.26–7.11(m, 5H), 4.35–4.23(m, 1H), 4.11(dd, J=11.1 Hz, 4.2 Hz, 1H), 4.01(dd, J=11.1, 6.6 Hz, 1H), 2.84–2.68(m, 2H), 2.43–2.34(m, 1H), 1.93(s, 3H), 1.80–1.63(m, 2H).

EXAMPLE 8(6)

N-hydroxy-5-ethoxymethoxy-2(R)-methoxymethyl-4(S)-[N-(4-phenoxyphenylcarbonyl)amino]pentanamide

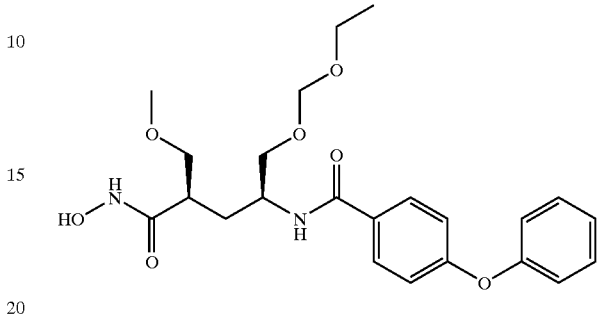

TLC: Rf 0.28 (chloroform:methanol=19:1);

NMR (300 MHz, $d_6$-DMSO): δ10.80–10.00(br, 1H), 9.20–8.40(br, 1H), 8.12(d, J=8.4 Hz, 1H), 7.88 (d, J=8.7 Hz, 2H), 7.47–7.38 (m, 2H), 7.21–7.16(m, 1H), 7.06(d, J=7.8 Hz, 2H), 7.01(d, J=8.7 Hz, 2H), 4.58(s, 2H), 4.16–4.00(m, 1H), 3.57–3.30(m, 6H), 3.17(s, 3H), 2.43–2.34(m, 1H), 1.81–1.53(m, 2H), 1.08(t, J=6.9 Hz, 3H).

EXAMPLE 8(7)

N-hydroxy-5-ethoxymethoxy-2(R)-methoxymethyl-4(S)-(N-(4-(2-furyl)phenylcarbonyl)amino]pentanamide

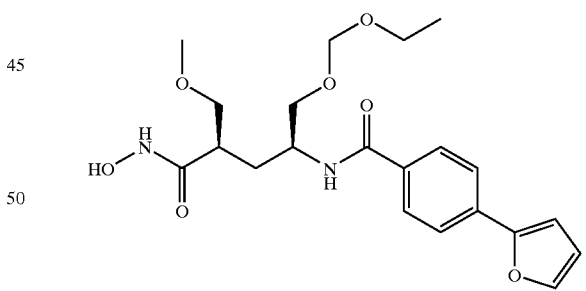

TLC: Rf 0.39 (chloroform:methanol:acetic acid:water= 100:10:1:1);

NMR ($CDCl_3+CD_3OD$(a little)): δ7.82(d, J=8.8 Hz, 2H), 7.71(d, J=8.8 Hz, 2H), 7.51(m, 1H), 7.17(d, J=8.8 Hz, 1H), 6.75(m, 1H), 6.50(m, 1H), 4.71(d, J=6.6 Hz, 1H), 4.67(d, J=6.6 Hz, 1H), 4.31(m, 1H), 3.73–3.46(m, 6 H), 3.35(s, 3H), 2.64(m, 1H), 2.11(m, 1H), 1.83(m, 1H), 1.20(t, J=7.1 Hz, 3H).

EXAMPLE 8(8)

N-hydroxy-5-ethoxymethoxy-2(R)-ethoxymethyl-4 (S)-[N-(4-cyanophenylcarbonyl)amino]pentanamide

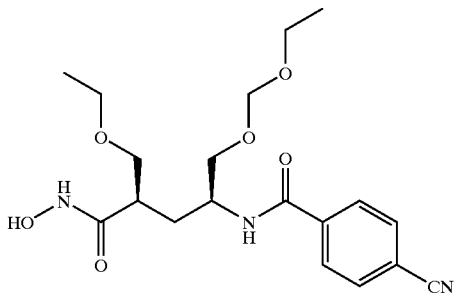

TLC: Rf 0.50 (chloroform:methanol=9:1);

NMR (300 MHz, $d_6$-DMSO): $\delta$10.44(1H, s), 8.75(1H, s), 8.40(1H, d, J=8.4 Hz), 7.97(2H, d, J=8.4 Hz), 7.94(2H, d, J=8.4 Hz), 4.58(2H, s), 4.15–4.04(1H, m), 3.53–3.30(8H, m), 2.37(1H, quint, J=5.3 Hz), 1.81–1.70(1H, m), 1.68–1.55 (1H, m), 1.07(3H, t, J=7.2 Hz), 1.05(3H, t, J=6.9 Hz).

EXAMPLE 8(9)

N-hydroxy-5-ethoxymethoxy-2(S)-methoxymethyl-4 (R)-[N-(4-nitrophenylcarbonyl)amino]pentanamide

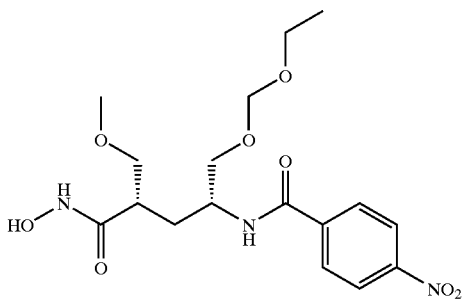

TLC: Rf 0.22 (chloroform:methanol=19:1);

NMR (300 MHz, $d_6$-DMSO): $\delta$10.60–10.30(brs, 1H), 8.85–8.62(brs, 1H), 8.52(d, J=8.7 Hz, 1H), 8.30(d, J=8.7 Hz, 2H), 8.06(d, J=8.7 Hz, 2H), 4.59(s, 2H), 4.17–4.03(m, 1H), 3.58–3.28(m, 6H), 3.18(s, 3H), 2.44–2.33(m, 1H), 1.81–1.56(m, 2H), 1.08(t, J=6.9 Hz, 3H).

EXAMPLE 8(10)

N-hydroxy-5-ethoxymethoxy-2(S)-methoxymethyl-4 (R)-[N-(4-chlorophenylcarbonyl)amino]pentanamide

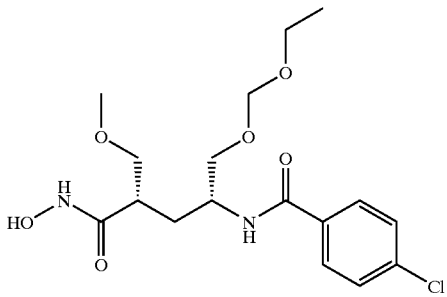

TLC: Rf 0.31 (chloroform:methanol=9:1);

NMR (300 MHz, $d_6$-DMSO): $\delta$10.52–10.35(brs, 1H), 8.84–8.67(brs, 1H), 8.22(d, J=8.4 Hz, 1H), 7.85(d, J=8.7 Hz, 2H), 7.52(d, J=8.7 Hz, 2H), 4.58(s, 2H), 4.15–4.00(m, 1H), 3.53–3.29(m, 6H), 3.17(s, 3H), 2.43–2.32(m, 1H), 1.80–1.54(m, 2H), 1.07(t, J=7.2 Hz, 3H).

EXAMPLE 8(11)

N-hydroxy-5-ethoxymethoxy-2(S)-methoxymethyl-4 (R)-[N-(4-bromophenylcarbonyl)amino]pentanamide

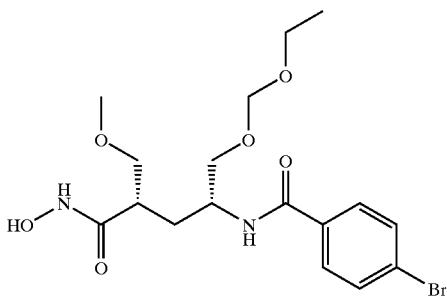

TLC: Rf 0.31 (chloroform:methanol=9:1);

NMR (300 MHz, $d_6$-DMSO): $\delta$10.43(s, 1H), 8.74(brs, 1H), 8.21(d, J=8.4 Hz, 1H), 7.78(d, J=8.7 Hz, 2H), 7.66(d, J=8.7 Hz, 2H), 4.58(s, 2H), 4.13–4.01(m, 1H), 3.50–3.31(m, 6H), 3.16(s, 3H), 2.42–2.12(m, 1H), 1.79–1.53(m, 2H), 1.07(t, J=7.2 Hz, 3H).

EXAMPLE 8(12)

N-hydroxy-5-ethoxymethoxy-2(S)-methoxymethyl-4 (R)-[N-(4-cyanophenylcarbonyl)amino]pentanamide

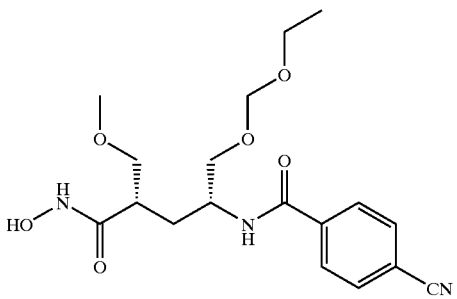

TLC: Rf 0.38 (chloroform:methanol=9:1);

NMR (300 MHz, d$_6$-DMSO): δ10.44(1H, s), 8.75(1H, s), 8.40(1H, d, J=8.7 Hz), 7.97(2H, d, J=8.8 Hz), 7.95(2H, d, J=8.8 Hz), 4.58(2H, s), 4.16–4.03(1H, m), 3.54–3.28(6H, m), 3.17(3H, s), 2.44–2.33(1H, m), 1.80–1.69(1H, m), 1.68–1.55(1H, m), 1.07(3H, t, J=7.1 Hz).

EXAMPLE 8(13)

N-hydroxy-5-ethoxymethoxy-2(S)-benzyl-4(S)-[N-(4-chlorocyclohexylcarbonyl)amino]pentanamide

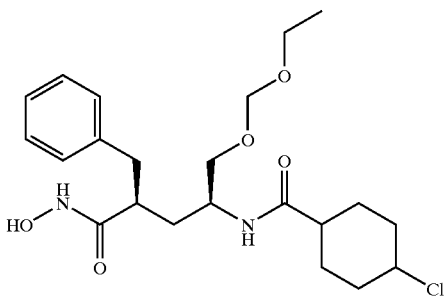

TLC: Rf 0.35 (chloroform:methanol=9:1).

EXAMPLE 9

5-ethoxymethoxy-4(S)-[N-(4-nitrophenylcarbonyl)amino]pentanoic acid

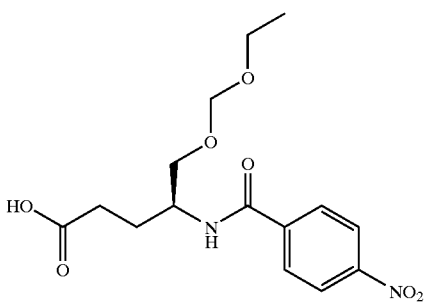

The title compound having the following physical data was obtained by the same procedure as a series of reaction of Example 6, using the compound prepared in Example 3(1).

TLC: Rf 0.34 (chloroform:methanol=9:1);

NMR (200 MHz, CDCl$_3$): δ8.28(d, J=8.8 Hz, 2H), 7.97(d, J=8.8 Hz, 2H), 7.08(d, J=8.8 Hz, 1H), 4.75(d, J=7. Hz, 1H), 4.70(d, J=7.0 Hz, 1H), 4.43–4.27(m, 1H), 3.83(dd, J=10.6, 3.4 Hz, 1H), 3.72–3.57(m, 3H), 2.65–2.38(m, 2H), 2.17–1.94(m, 2H), 1.21(t, J=7.0 Hz, 3H).

EXAMPLE 10

N-hydroxy-5-ethoxymethoxy-4(S)-[N-(4-nitrophenylcarbonyl)amino]pentanamide

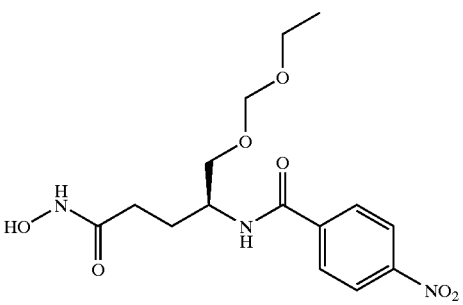

The title compound having the following physical data was obtained by the same procedure as a series of reaction of Example 7→Example 8, using the compound prepared in Example 9.

TLC: Rf 0.34 (chloroform:methanol=9:1);

NMR (200 MHz, d$_6$-DMSO): δ10.35(s, 1H), 8.57(d, J=8.4 Hz, 1H), 8.31(d, J=8.8 Hz, 2H), 8.07(d, J=8.8 Hz, 2H), 4.60(s, 2H), 4.23–3.99(m, 1H), 3.62–3.40(m, 4H), 2.10–1.60(m, 4H), 1.08(t, J=7.0 Hz, 3H).

Reference Example 4

4(S)-(4-amino-5-methoxyethoxymethoxy)pentanoic acid benzyl ester

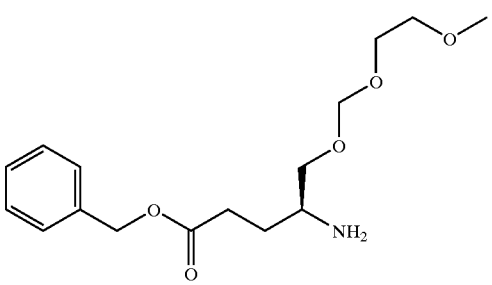

To a solution of 4(S)-[5-methoxyethoxymethoxy-4-(N-t-butoxycarbonyl amino)]pentanoic acid benzyl ester (8.83 g) that was obtained by the same procedure as a series of reaction of Reference example 1→Reference example 2 (using methoxyethoxymethyl chloride instead of ethoxymethyl chloride), using 4(S)-carboxy-4-(N-t-butoxycarbonylamino)butanoic acid benzyl ester, in methylene chloride (15 ml) in ice-bath, trifluoroacetic acid (15 ml) was added. The mixture was stirred for 80 minutes at 0° C. The reaction mixture was diluted with ethyl acetate/toluene and concentrated to give the title compound (8.84 g) having the following physical data.

TLC: Rf 0.36 (chloroform:methanol=9:1).

EXAMPLE 11

5-methoxyethoxymethoxy-2(S)-methyl-4(S)-[N-methyl-N-(4-nitrophenylcarbonyl)amino]pentanoic acid benzyl ester

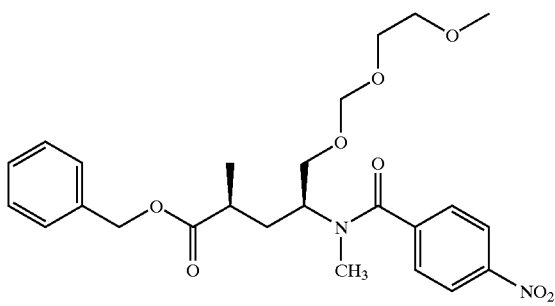

To a solution of 5-methoxyethoxymethoxy-2(S)-methyl-4(S)-[N-(4-nitrophenylcarbonyl)amino]pentanoic acid benzyl ester (820 mg) that was obtained by the same procedure as a series of reaction of Example 1 (using 4-nitrobenzoyl chloride instead of 4-iodobenzoyl chloride)→Example 5 (using methyl iodide instead of methoxymethyl chloride), using the compound prepared in Reference example 4, in THF (15 ml), methyl iodide (0.6 ml) was added. Then 60% sodium hydride (84 mg) was added to the mixture under cooling with ice. The mixture was stirred for 4 hours at 0° C. The reaction mixture was poured into 5% aqueous solution of citric acid, and extracted with ethyl acetate. The extract was dried over anhydrous magnesium sulfate and concentrated to give the title compound having the following physical data.

TLC: Rf 0.20 (toluene:methanol=2:1).

EXAMPLE 12

5-methoxyethoxymethoxy-2(S)-methyl-4(S)-[N-methyl-N-(4-nitrophenylcarbonyl)amino]pentanoic acid

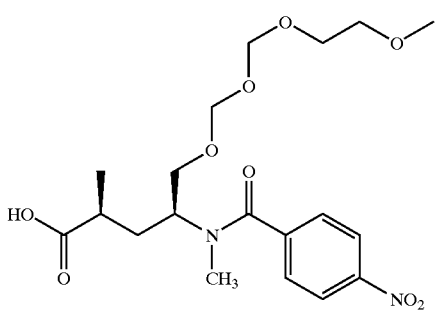

To a solution of the compound prepared in Example 11 (319 mg) in THF/methanol (1:1, 6 ml), 2N aqueous solution of sodium hydroxide (0.6 ml) was added. The mixture was stirred for 150 minutes at room temperature. The reaction mixture was neutralized by adding 2N aqueous solution of hydrochloric acid, and extracted with ethyl acetate. The extract was dried over anhydrous magnesium sulfate and concentrated to give the title compound having the following physical data.

MASS (APCI, neg, 20 V): 397(M−H)⁻.

EXAMPLE 13

N-hydroxy-2(S)-methyl-5-methoxyethoxymethoxy-4(S)-[N-methyl-N-(4-nitrophenylcarbonyl)amino]pentanamide

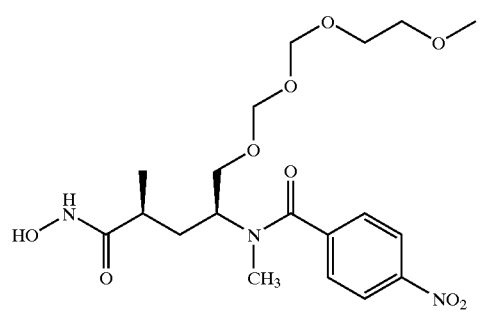

The following compound having the following physical data was obtained by the same procedure as a series of reaction of Example 7→Example 8, using the compound prepared in Example 12.

TLC: Rf 0.73 (chloroform:methanol=9:1);

NMR (300 MHz, $d_6$-DMSO): δ10.50 and 10.43 (s, 1H), 8.90–8.50 (brs, 1H), 8.28 and 8.25(d, J=8.8 Hz, 2H), 7.63 and 7.59(d, J=8.8 Hz, 2H), 4.83–4.69 and 3.84–3.75(m, 1H), 4.69–4.57(m, 2H), 3.63–3.49(m, 2H), 3.48–3.37(m, 4H), 3.24 and 3.22(s, 3H), 2.82 and 2.63(s, 3H), 2.20–2.08 and 2.06–1.94(m, 1H), 1.89–1.71(m, 1H), 1.54–1.43 and 1.40–1.29(m, 1H), 1.05 and 0.76(d, J=6.6 Hz, 3H).

EXAMPLE 14

5-hydroxy-4(S)-[N-(4-nitrophenylcarbonyl)amino]pentanoic acid allyl ester

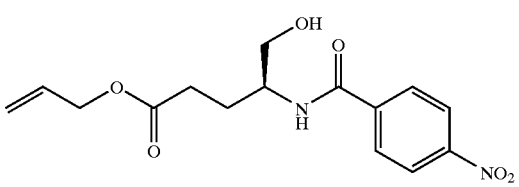

To a solution of the compound prepared in Example 3(1) (5.02 g) in allyl alcohol (15 ml), concentrated hydrochloric acid (40 drops) was added, and the mixture was stirred for 30 minutes at 50° C. The reaction mixture was cooled to room temperature, neutralized by adding sodium bicarbonate and extracted with ethyl acetate. The extract was dried over anhydrous magnesium sulfate to give the title compound having the following physical data.

TLC: Rf 0.35 (toluene:ethyl acetate=1:4);

MASS (APCI, pos, 20 V): 323(M+H)⁺.

Reference Example 5

5-t-butyldimethylsilyloxy-4(S)-[N-(4-nitrophenylcarbonyl)amino]pentanoic acid allyl ester

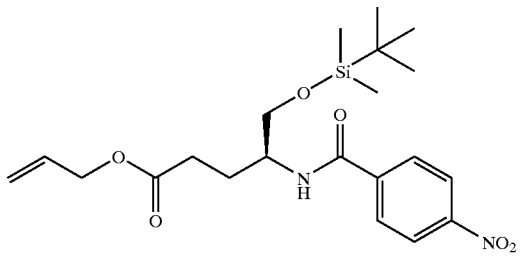

To a solution of the compound prepared in Example 14 (4.24 g) in DMF (13 ml), imidazole (2.15 g) and t-butyldimethylsilyl chloride (2.38 g) were added, and the mixture was stirred for 30 minutes. The reaction mixture was extracted with ethyl acetate. The extract was dried over anhydrous magnesium sulfate and concentrated to give the title compound (4.75 g) having the following physical data.

NMR (CDCl$_3$): δ8.29(2H, d, J=8.9 Hz), 7.93(2H, d, J=8.9 Hz), 6.80(1H, d, J=8.8 Hz), 5.97–5.76(1H, m), 5.34–5.16 (2H, m), 4.59–4.52(2H, m), 4.28–4.08(1H, m), 3.77–3.72 (2H, m), 2.67–2.37(2H, m), 2.17–1.91(2H, m), 0.90(9H, s), 0.05(6H, s).

Reference Example 6

5-t-butyldimethylsilyloxy-2(R)-methoxymethyl-4(S)-[N-(4-nitrophenylcarbonyl)amino]pentanoic acid allyl ester

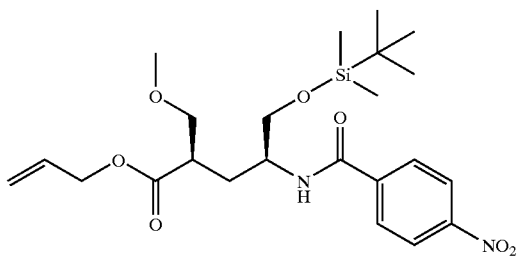

The title compound having the following physical data was obtained by the same procedure as a series of reaction of Example 5, using the compound prepared in Reference example 5.

TLC: Rf 0.50 (toluene ethyl acetate=3:1);

NMR (CDCl$_3$): δ8.29(2H, d, J=8.9 Hz), 7.92(2H, d, J=8.9 Hz), 6.60(1H, d, J=8.1 Hz), 5.88–5.74(1H, m), 5.27–5.13 (2H, m), 4.62–4.43(2H, m), 4.29–4.17(1H, m), 3.76–3.69 (2H, m), 3.68–3.56(2H, m), 3.34(3H, s), 2.83–2.73(1H, m), 2.23–2.10(1H, m), 1.96–1.87(1H, m), 0.89(9H, s), 0.07(3H, s), 0.04(3H, s).

Reference Example 7

2(S)-(benzothiophen-3-yl)methyl-5-t-butyldimethylsilyloxy-4(S)-[N-(4-nitrophenylcarbonyl)amino]pentanoic acid allyl ester

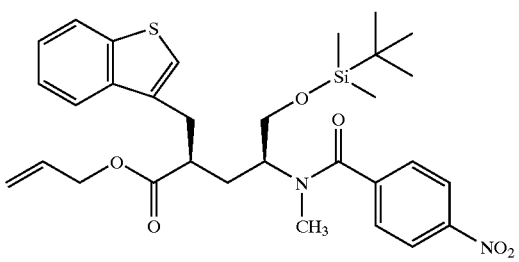

The title compound having the following physical data was obtained by the same procedure as a series of reaction of Example 5→Example 11, using the compound prepared in Reference example 5 and a corresponding compound.

TLC: Rf 0.54 (toluene:ethyl acetate=4:1);

MASS (APCI, pos, 20 V.): 597(M+H)$^+$, 465.

Reference Example 8

5-t-butyldimethylsilyloxy-2(R)-methoxymethyl-4(S)-[N-(4-nitrophenylcarbonyl)amino]pentanoic acid

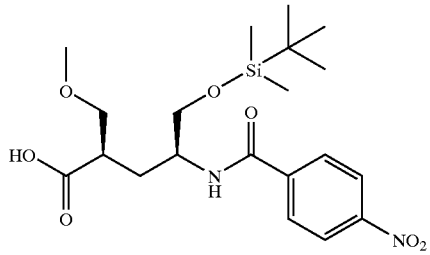

The title compound having the following physical data was obtained by the same procedure as a series of reaction of Example 6, using the compound prepared in Reference example 6.

NMR (d$_6$-DMSO): δ12.18(1H, s), 8.44(1H, d, J=9.0 Hz), 8.30(2H, d, J=9.0 Hz), 8.03(2H, d, J=9.0 Hz), 4.12–3.98(1H, m), 3.63–3.52(2H, m), 3.46(2H, d, J=6.3 Hz), 3.19(3H, s), 2.59–2.48(1H, m), 1.86–1.67(2H, m), 0.82(9H, s), 0.03(6H, s).

EXAMPLE 15

N-hydroxy-5-hydroxy-2(R)-methoxymethyl-4(S)-[N-(4-nitrophenylcarbonyl)amino]pentanamide

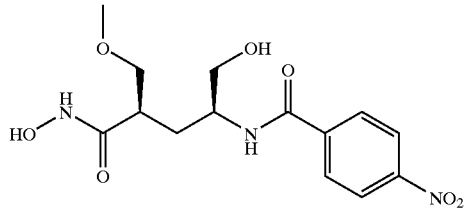

The title compound having the following physical data was obtained by the same procedure as a series of reaction of Example 7→Example 8, using the compound prepared in Reference example 8.

TLC: Rf 0.18 (chloroform:methanol=9:1);

NMR (300 MHz, $d_6$-DMSO): δ10.43(1H, s), 8.73(1H, brs), 8.35(1H, d, J=8.1 Hz), 8.29(2H, d, J=8.7 Hz), 8.07(2H, d, J=8.7 Hz), 4.74(1H, t, J=5.7 Hz), 4.02–3.89(1H, m), 3.50–3.31(4H, m), 3.17(3H, s), 2.45–2.34(1H, m), 1.82–1.70(1H, m), 1.64–1.51(1H, m).

EXAMPLE 15(1)

N-hydroxy-5-hydroxy-2(R)-methoxymethyl-4(S)-[N-(4-chlorophenylcarbonyl)amino]pentanamide

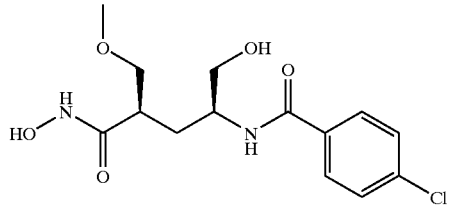

The title compound having the following physical data was obtained by the same procedure as a series of reaction of Reference example 1→Reference example 2→Reference example 3→Example 1 (using 4-chiorobenzoyl chloride instead of 4-iodobenzoyl chloride)→Example 2→Example 3→Example 14→Reference example 5-→Reference example 6→Reference example 8→Example 15, using a corresponding compound.

TLC: Rf 0.20 (chloroform:methanol=9:1);

NMR (300 MHz, $d_6$-DMSO): δ10.41(1H, s), 8.72(1H, s), 8.05(1H, d, J=8.4 Hz), 7.86(2H, d, J=8.4 Hz), 7.51(2H, d, J=8.4 Hz), 4.69(1H, t, J=5.7 Hz), 4.00–3.86(1H, m), 3.49–3.27(4H, m), 3.17(3H, s), 2.44–2.30(1H, m), 1.82–1.69(1H, m), 1.61–1.49(1H, m).

EXAMPLE 15(2)

N-hydroxy-2(S)-(2-benzothiophen-3-yl)methyl)-5-hydroxy-4(S)-[N-methyl-N-(4-nitrophenylcarbonyl)amino]pentanamide

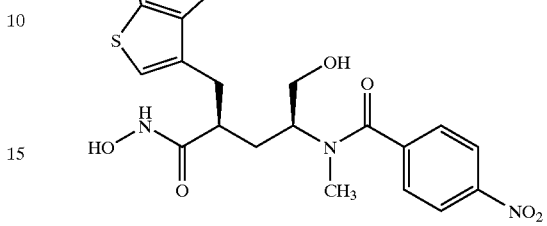

The title compound having the following physical data was obtained by the same procedure as a series of reaction of Reference example 8→Example 15, using the compound prepared in Reference example 7.

TLC: Rf 0.40 (chloroform:methanol=9:1);

NMR (300 MHz, $d_6$-DMSO): δ10.52 and 10.50(brs, 1H), 8.74(s, 1H), 8.29 and 7.95(d, J=8.7 Hz, 2H), 7.96–7.93(m, 1H), 7.87–7.85 and 7.62–7.59(m, 1H), 7.69 and 7.47(d, J=8.7 Hz, 2H), 7.37–7.29(m, 3H), 4.99–4.96 and 4.88–4.85 (m, 1H), 4.81–4.72 and 3.52–3.46(m, 1H), 3.57–3.40 and 3.30–3.23(m, 2H), 3.05–3.02 and 2.92–2.87(m, 2H), 2.83 and 2.66(s, 3H), 2.49–2.35(m, 1H), 1.87–1.65 and 1.57–1.46 (m, 2H).

EXAMPLE 16(1)~16(5)

The following compounds were obtained by the same procedure as a series of reaction of Example 14 Reference example 5→Example 5 (using a corresponding compound instead of methoxymethyl chloride)→Example 11→Example 12→Example 7→Example 8, using the compound prepared in Example 1 or a corresponding compound thereof.

EXAMPLE 16(1)

N-hydroxy-2(S)-allyl-5-hydroxy-4(S)-[N-methyl-N-(4-nitrophenylcarbonyl)amino]pentanamide

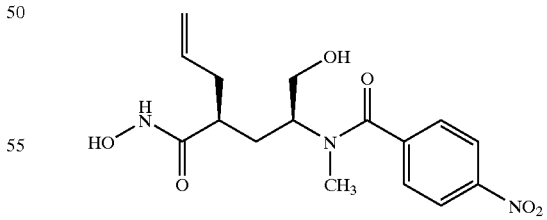

TLC: Rf 0.25 (chloroform:methanol:water=9:1:0.1);

NMR (300 MHz, $d_6$-DMSO): δ10.51 and 10.44(s, 1H), 8.76 and 8.70(s, 1H), 8.27 and 8.24(d, J=8.1 Hz, 2H), 7.65 and 7.61(d, J=8.1 Hz, 2H), 5.81–5.50(m, 1H), 5.08–4.78(m, 3H), 4.64–4.55 and 3.50–3.39(s, 1H), 3.54–3.37(m, 2H), 2.81 and 2.62(s, 3H), 2.24–2.18 and 2.16–2.06(m, 1H), 2.07–1.88(m, 2H), 1.77–1.52 and 1.44–1.31(m, 2H).

EXAMPLE 16(2)

N-hydroxy-2(S)-(3-phenylpropyl)-5-hydroxy-4(S)-[N-methyl-N-(4-bromophenylcarbonyl)amino]pentanamide

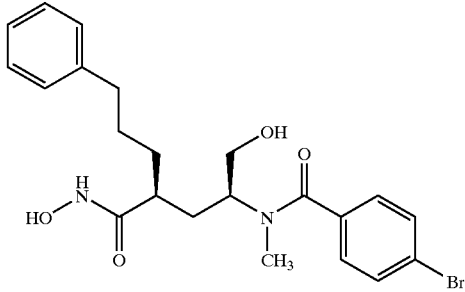

TLC: Rf 0.54 (chloroform:methanol:acetic acid=9:1:0.5);

NMR (300 MHz, $d_6$-DMSO): δ10.50 and 10.45(s, 1H), 8.74 and 8.70(s, 1H), 7.66–7.57(m, 2H), 7.39–7.34(m, 2H), 7.30–7.21(m, 2H), 7.19–7.08(m, 3H), 4.96 and 4.76(t, J=5.4 Hz, 1H), 4.58–4.37 and 3.68–3.57(m, 1H), 3.51–3.41 and 3.34–3.25(m, 2H), 2.77 and 2.63(s, 3H), 2.39–2.25(m, 2H), 2.08–1.98 and 1.86–1.77(m, 1H), 1.74–1.44(m, 2H), 1.38–1.13(m, 4H).

EXAMPLE 16(3)

N-hydroxy-2(S)-(3-phenylpropyl)-5-hydroxy-4(S)-[N-methyl-N-(4-nitrophenylcarbonyl)amino]pentanamide

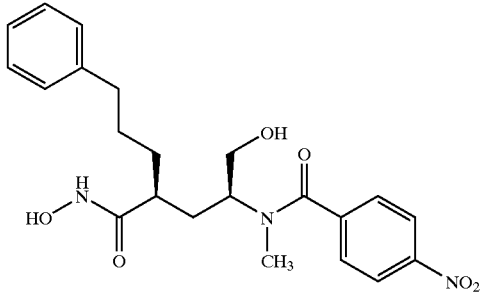

TLC: Rf 0.33 (chloroform:methanol:water=9:1:0.1);

NMR (300 MHz, $d_6$-DMSO): δ10.52 and 10.43(s, 1H), 8.77 and 8.70(s, 1H), 8.27 and 8.24 (d, J=8.6 Hz, 2H), 7.65 and 7.61 (d, J=8.6 Hz, 2H), 7.30–7.07(m, 5H), 4.99 and 4.81(t, J=5.3 Hz, 1H), 4.64–4.51 and 3.53–3.44(m, 1H), 3.52–3.41(m, 2H), 2.81 and 2.61(s, 3H), 2.41–2.32(m, 2H), 2.10–2.00 and 1.89–1.78(m, 1H), 1.74–1.47(m, 2H), 1.39–1.22(m, 4H).

EXAMPLE 16(4)

N-hydroxy-2(S)-methyl-5-hydroxy-4(S)-[N-methyl-N-[(5-nitro-2-thienyl)carbonyl]amino]pentanamide

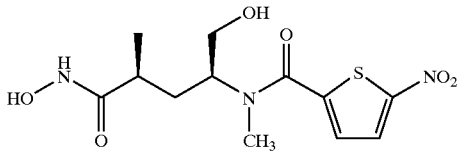

TLC: Rf 0.19 (chloroform:methanol:acetic acid=90:10:1);

NMR (300 MHz, $d_6$-DMSO): δ10.43(brs, 1H), 8.69(brs, 1H), 8.09 and 8.04(d, J=3.9 Hz, 1H), 7.52 and 7.50(d, J=3.9 Hz, 1H), 5.14 and 4.80(brs, 1H), 4.58–4.48 and 4.05–3.93 (m, 1H), 3.50–3.36(m, 2H), 2.90 and 2.80(s, 3H), 2.09–1.95 (m, 1H), 1.80–1.64(m, 1H), 1.52–1.35(m, 1H), 1.00–0.82(d, J=6.6 Hz, 3H).

EXAMPLE 16(5)

N-hydroxy-2(S)-benzyl-5-hydroxy-4(S)-[N-methyl-N-[(5-bromo-2-thienyl)carbonyl]amino]pentanamide

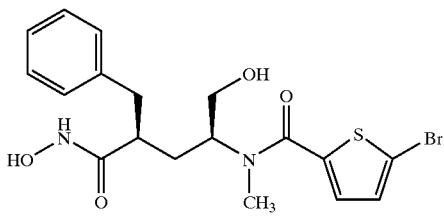

TLC: Rf 0.41 (chloroform:methanol:acetic acid=90:10:1);

NMR (300 MHz, $d_6$-DMSO): δ10.34(brs, 1H), 8.65(brs, 1H), 7.40–6.98(m, 7H), 5.06 and 4.77(brs, 1H), 4.72–4.61 and 4.36–4.21(m, 1H), 3.52–3.38(m, 2H), 3.02 and 2.77(s, 3H), 2.76–2.52 and 2.49–2.23(m, 1H), 2.21–2.09(m, 1H), 1.76–1.45(m, 2H).

EXAMPLE 17(1)~17(3)

The following compounds were obtained by the same procedure as a series of reaction of Example 1, using trans-2-aminomethylcyclohexanoic acid that was described in J. Chem. Soc. Perkin Trans I, 2563 (1982), or 2-aminocyclohexane carboxylic acid that was described in J. Chem. Soc. Perkin Trans I, 2555 (1982), and a corresponding acyl chloride.

EXAMPLE 17(1)

trans-2-[(4-nitrophenylcarbonyl)aminomethyl]
cyclohexanoic acid

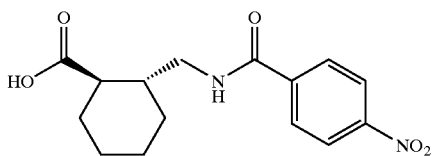

TLC: Rf 0.50 (chloroform:methanol=9:1).

EXAMPLE 17(2)

trans-2-[(4-(3-methoxy-1-propynyl)phenylcarbonyl)
aminomethyl]cyclohexanoic acid

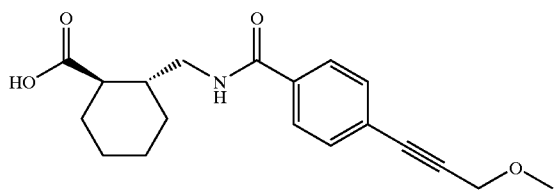

TLC: Rf 0.55 (chloroform:methanol=9:1).

EXAMPLE 17(3)

trans-2-[(4-nitrophenylcarbonyl)amino]
cyclohexylacetic acid

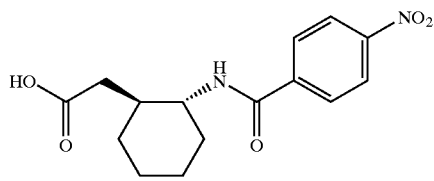

EXAMPLE 18(1)~18(3)

The following compounds were obtained by the same procedure as a series of reaction of Example 7→Example 8, using the compound prepared in Example 17(1)~17(3).

EXAMPLE 18(1)

trans-1-(N-hydroxyaminocarbonyl)-2-[(4-
nitrophenylcarbonyl)aminomethyl]cyclohexane

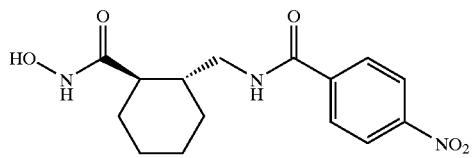

TLC: Rf 0.38 (chloroform:methanol=9:1);
NMR (300 MHz, $d_6$-DMSO): $\delta$10.43(s, 1H), 8.57(t, J=5.4 HZ, 1H), 8.28(d, J=8.9 Hz, 2H), 8.05(d, J=8.9 Hz, 2H), 3.20–3.02(m, 2H), 1.95–1.55(m, 6H), 1.55–1.30(m, 1H), 1.30–1.02(m, 2H), 1.00–0.80(m, 1H).

EXAMPLE 18(2)

trans-1-(N-hydroxyaminocarbonyl)-2-[(4-(3-
methoxy-1-propynyl)phenylcarbonyl)aminomethyl]
cyclohexane

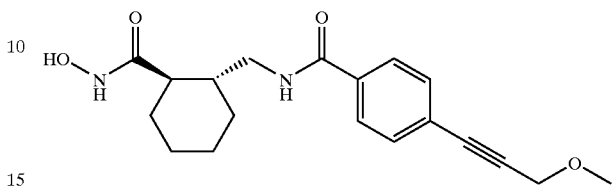

TLC: Rf 0.41 (chloroform:methanol=9:1);

NMR (300 MHz, $d_6$-DMSO): $\delta$10.42(s, 1H), 9.00–8.35 (br, 1H), 8.29(t, J=5.6 Hz, 1H), 7.82(d, J=8.9 Hz, 1H), 7.52(d, J=8.9 Hz, 2H), 4.34(s, 2H), 3.33(s, 3H, overlap with H2O in DMSO), 3.18–3.02(m, 2H), 1.90–1.55(m, 6H), 1.55–1.30(m, 1H), 1.28–1.02(m, 2H), 1.00–0.78(m, 1H).

EXAMPLE 18(3)

trans-1-(N-hydroxyaminocarbonylmethyl)-2-[(4-
nitrophenylcarbonyl)amino]cyclohexane

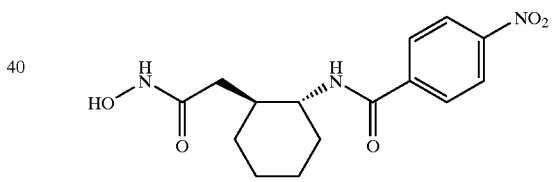

TLC: Rf 0.37 (chloroform:methanol=9:1);

NMR (300 MHz, $d_6$-DMSO): $\delta$10.33(s, 1H), 8.62(d, J=8.7 Hz, 1H), 8.29(d, J=8.7 Hz, 2H), 8.05(d, J=8.7 Hz, 2H), 3.70–3.50(m, 1H, overlap with $H_2O$ in DMSO), 2.16(dd, J=14.1, 3.3 Hz, 1H), 2.00–1.60(m, 6H), 1.45–0.85(m, 4H).

EXAMPLE 19(1)~19(3)

The following compounds were obtained by the same procedure as a series of reaction of Example 5 (using a corresponding compound instead of methoxymethyl chloride)→Example 6, using the compound prepared in Example 3(1) or a corresponding compound thereof.

EXAMPLE 19(1)

5-ethoxymethoxy-2(R)-(2-propynyloxymethyl)-4(S)-[N-(4-nitrophenylcarbonyl)amino]pentanoic acid

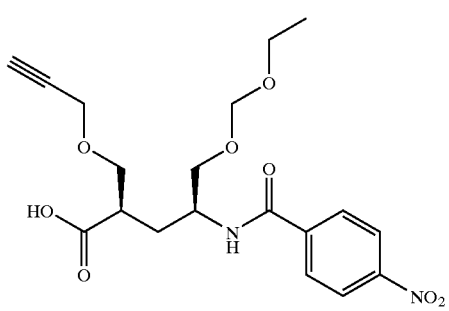

TLC: Rf 0.41 (chloroform:methanol=9:1);

NMR (200 MHz, CDCl$_3$): δ8.26 (d, J=8.8 Hz, 2H), 7.95 (d, J=8.8 Hz, 2H), 7.03(d, J=8.8 Hz, 1H), 4.73(d, J=6.8 Hz, 1H), 4.68(d, J=6.8 Hz, 1H), 4.50–4.31(m, 1H), 4.18(d, J=2.2 Hz, 2H), 3.88–3.52(m, 6H), 2.88–2.70(m, 1H), 2.46(t, J=2.2 Hz, 1H), 2.17(ddd, J=14.2, 9.6, 8.2 Hz, 1H), 1.92(dt, J=14.2, 5.4 Hz, 1H), 1.20(t, J=7.0 Hz, 3H).

EXAMPLE 19(2)

5-ethoxymethoxy-2(R)-(2-propenyloxymethyl)-4(S)-[N-(4-nitrophenylcarbonyl)amino]pentanoic acid

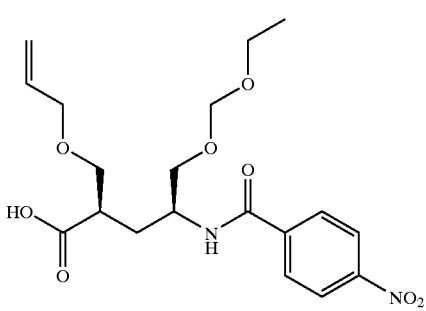

TLC: Rf 0.25 (chloroform:methanol=9:1);

NMR (300 MHz, CDCl$_3$): δ8.25(d, J=8.7 Hz, 2H), 7.95(d, J=8.7 Hz, 2H), 7.06(d, J=9.0 Hz, 1H), 5.94–5.78(m, 1H), 5.31–5.16(m, 2H), 4.73 (d, J=6.6 Hz, 1H), 4.67 (d, J=6.6 Hz, 1H), 4.44–4.32 (m, 1H), 4.02–3.98(m, 2H), 3.79(dd, J=10.5, 3.3 Hz, 1H), 3.75–3.55(m, 5H), 2.83–2.73(m, 1H), 2.15 (ddd, J=14.7, 10.2, 8.1 Hz, 1H), 1.90(dt, J=14.7, 5.4 Hz, 1H), 1.20(t, J=7.2 Hz, 3H).

EXAMPLE 19(3)

5-ethoxymethoxy-2(R)-(2-propynyloxymethyl)-4(S)-[N-(4-chlorophenylcarbonyl)amino]pentanoic acid

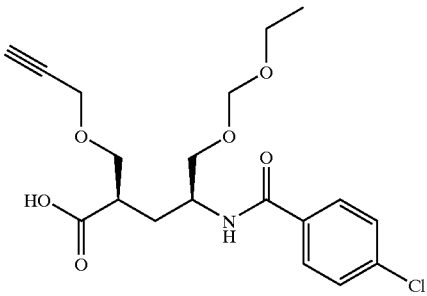

TLC: Rf 0.39 (chloroform:methanol=9:1);

NMR (200 MHz, CDCl$_3$): δ7.71(d, J=8.8 Hz, 2H), 7.37(d, J=8.8 Hz, 2H), 6.80(d, J=8.8 Hz, 1H), 4.71(d, J=6.6 Hz, 1H), 4.68(d, J=6.6 Hz, 1H), 4.47–4.30(m, 1H), 4.18(d, J=2.4 Hz, 2H), 3.85–3.68(m, 3H), 3.66–3.52(m, 3H), 2.84–2.70(m, 1H), 2.45(t, J=2.4 Hz, 1H), 2.15(ddd, J=14.4, 10.0, 7.8 Hz, 1H), 1.92(dt, J=14.4, 5.6 Hz, 1H), 1.20(t, J=7.2 Hz, 3H).

EXAMPLE 20(1)~20(3)

The following compounds were obtained by the same procedure as a series of reaction of Example 7→Example 8, using the compound prepared in Example 19(1)~19(3).

EXAMPLE 20(1)

N-hydroxy-5-ethoxymethoxy-2(R)-(2-propynyloxymethyl)-4(S)-[N-(4-nitrophenylcarbonyl)amino]pentanamide

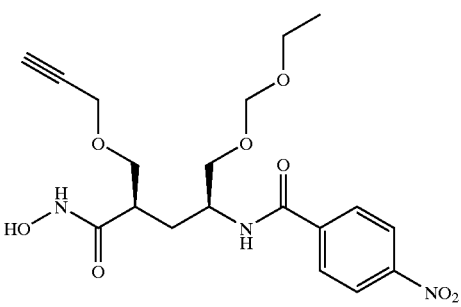

TLC: Rf 0.51 (chloroform:methanol=9:1);

NMR (200 MHz, CD$_3$OD): δ8.29(d, J=8.8 Hz, 2H), 8.00(d, J=8.8 Hz, 2H), 4.68(s, 2H), 4.38–4.20(m, 1H), 4.13(d, J=1.8 Hz, 2H), 3.70–3.48(m, 6H), 2.83(t, J=1.8 Hz, 1H), 2.60–2.42(m, 1H), 1.98–1.83(m, 2H), 1.16(t, J=7.2 Hz, 3H).

EXAMPLE 20(2)

N-hydroxy-5-ethoxymethoxy-2(R)-(2-propenyloxymethyl)-4(S)-[N-(4-nitrophenylcarbonyl)amino]pentanamide

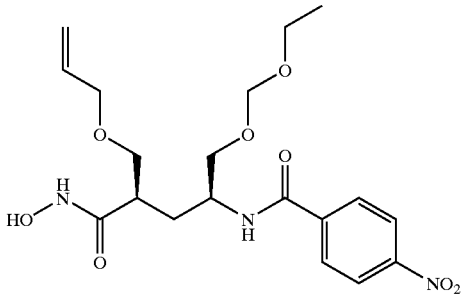

TLC: Rf 0.30 (chloroform:methanol=19:1);

NMR (300 MHz, $d_6$-DMSO): δ10.46(brs, 1H), 8.77(brs, 1H), 8.52(d, J=9.0 Hz, 1H), 8.30(d, J=8.7 Hz, 2H), 8.06(d, J=8.7 Hz, 2H), 5.90–5.74(m, 1H), 5.27–5.06(m, 2H), 4.59(s, 2H), 4.19–4.02(m, 1H), 3.96–3.80(m, 2H), 3.58–3.37(m, 6H), 2.44–2.34(m, 1H), 1.82–1.71(m, 1H), 1.70–1.58(m, 1H), 1.08(t, J=6.9 Hz, 3H).

EXAMPLE 20(3)

N-hydroxy-5-ethoxymethoxy-2(R)-(2-propynyloxymethyl)-4(S)-[N-(4-chlorophenylcarbonyl)amino]pentanamide

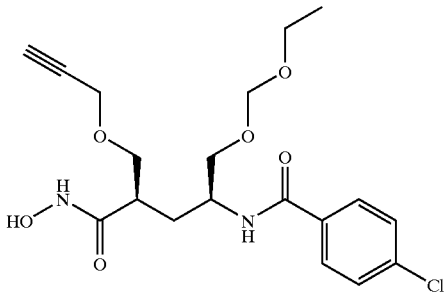

TLC: Rf 0.49 (chloroform:methanol=9:1);

NMR (300 MHz, $CD_3OD$): δ7.78(d, J=9.0 Hz, 2H), 7.44(d, J=9.0 Hz, 2H), 4.67(s, 2H), 4.30–4.20(m, 1H), 4.18–4.03(m, 2H), 3.70–3.50(m, 6H), 2.82(t, J=2.7 Hz, 1H), 2.57–2.43(m, 1H), 1.97–1.80(m, 2H), 1.15(t, J=6.9 Hz, 3H).

EXAMPLE 21(1)~21(4)

The following compounds were obtained by the same procedure as a series of reaction of Example 14→Reference example 5→Example 5 (using 2-propynyl bromide instead of methoxymethyl chloride)→Example 11→Example 12→Example 7→Example 8, using the compound prepared in Example 1 or a corresponding compound thereof.

EXAMPLE 21(1)

N-hydroxy-2(S)-(2-propynyl)-5-hydroxy-4(S)-[N-methyl-N-(4-nitrophenylcarbonyl)amino]pentanamide

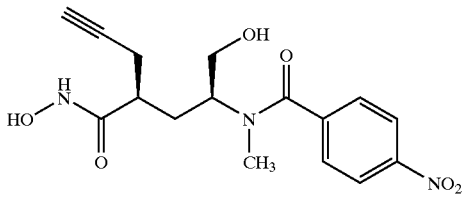

TLC: Rf 0.33 (chloroform:methanol:acetic acid=9:1:0.5);

NMR (300 MHz, $d_6$-DMSO): δ10.56(brs, 1H), 8.87 and 8.82(s, 1H), 8.33–8.16(m, 2H), 7.72–7.56(m, 2H), 5.00 and 4.86(t, J=5.6 Hz, 1H), 4.61–4.50 and 3.55–3.22 (m, 1H), 3.52–3.25 (m, 2H), 2.85 and 2.69(s, 1H), 2.81 and 2.63(s, 3H), 2.38–2.23(m, 2H), 1.91–1.61 and 1.48–1.38(m, 2H).

EXAMPLE 21(2)

N-hydroxy-2(S)-(2-propynyl)-5-hydroxy-4(S)-[N-methyl-N-(4-bromophenylcarbonyl)amino]pentanamide

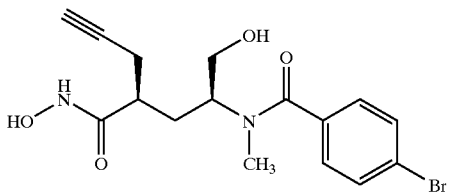

TLC: Rf 0.39 (chloroform:methanol:acetic acid=9:1:0.5);

NMR (300 MHz, $d_6$-DMSO): δ10.59(brs, 1H), 8.83(brs, 1H), 7.63 and 7.58(d, J=8.4 Hz, 2H), 7.36 and 7.32(d, J=8.4 Hz, 2H), 4.94 and 4.80(t, J=4.9 Hz, 1H), 4.58–4.47 and 3.63–3.52(m, 1H), 3.51–3.36 and 3.29–3.24(m, 2H), 2.80 and 2.71(s, 1H), 2.78 and 2.64(s, 3H), 2.38–2.03(m, 3H), 1.84–1.58 and 1.47–1.36(m, 2H).

EXAMPLE 21(3)

N-hydroxy-5-hydroxy-2(S)-(2-propynyl)-4(S)-[N-methyl-N-(4-chlorophenylcarbonyl)amino]pentanamide

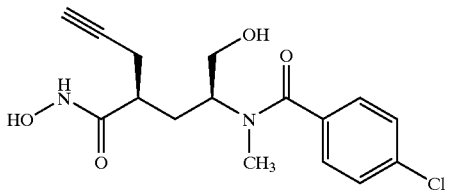

TLC: Rf 0.26 (chloroform:methanol:acetic acid=90:10:1);

NMR (300 MHz, $d_6$-DMSO): δ10.59(s, 1H), 8.83 and 8.82(s, 1H), 7.50–7.37(m, 4H), 4.95 and 4.80(t, J=5.4 Hz, 1H), 4.59–4.48 and 3.61–3.55(m, 1H), 3.51–3.39 and 3.32–3.23(m, 2H), 2.64 and 2.78(s, 3H), 2.38–2.29(m, 2 H), 2.20–2.01(m, 1H), 1.73–1.57(m, 2H).

EXAMPLE 21(4)

N-hydroxy-5-ethoxymethoxy-2(S)-(2-propynyl)-4(S)-[N-(4-cyanophenylcarbonyl)amino]pentanamide

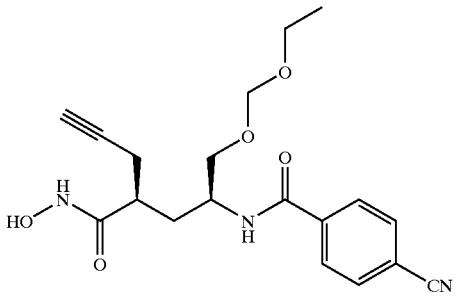

TLC: Rf 0.37 (chloroform:methanol=9:1);

NMR (300 MHz, $d_6$-DMSO): δ10.53(1H, s), 8.80(1H, brs), 8.41(1H, d, J=8.4 Hz), 7.98(2H, d, J=8.7 Hz), 7.94(2H, d, J=8.7 Hz), 4.59(2H, s), 4.17–4.04(1H, m), 3.54–3.43(4H, m), 2.80(1H, s), 2.36–2.23(3H, m), 1.90–1.78(1H, m), 1.73–1.61(1H, m), 1.07(3H, t, J=7.2 Hz).

Formulation Example

Formulation Example 1

The following components were admixed in conventional method and punched out to obtain 100 tablets each containing 50 mg of active ingredient.

| | |
|---|---|
| N-hydroxy-5-ethoxymethoxy-2(R)-methoxymethyl-4(S)-[N-(4-cyanophenyl carbonyl)amino]pentanamide | 5.0 g |
| Carboxymethyl Cellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| N-hydroxy-5-ethoxymethoxy-2(R)-methoxymethyl-4(S)-[N-(4-cyanophenyl carbonyl)amino]pentanamide | 2.0 g |
| Mannitol | 20 g |
| distilled water | 500 ml |

What is claimed is:

1. Aminobutyric acid derivatives of the formula (I):

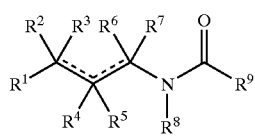

(I)

wherein
$R^1$ is —COOR$^{10}$, —CONHOR$^{10}$, —CONHNHR$^{10}$, —(CH$_2$)$_n$SR$^{50}$ or —Y—PO(OR$^{51}$)$_2$; R$^{10}$ is (i) hydrogen, (ii) C1–8 alkyl, (iii) C2–8 alkenyl, (iv) phenyl, (v) C1–8 alkyl substituted by phenyl or C1–8 alkoxy, or (vi) oxycarbonyl substituted by phenyl, benzyl or C1–8 alkyl;

n is 0–3;

$R^{50}$ is (i) hydrogen, (ii) C1–8 alkyl, (iii) —COR$^{52}$, in which R$^{52}$ is C1–8 alkyl or phenyl, (iv) —SR$^{53}$, in which R$^{53}$ is hydrogen, C1–8 alkyl or phenyl;

$R^{51}$ is hydrogen, C1–8 alkyl or phenyl;

Y is a single bond, —CH$_2$— or —O—;

$R^2$, $R^3$, $R^4$, $R^5$, $R^6$ and $R^7$ each, independently, is
(1) hydrogen,
(2) C1–8 alkyl,
(3) C2–8 alkenyl,
(4) —OR$^{11}$,
(5) —SR$^{11}$,
(6) —NR$^{12}$R$^{13}$,
(7) Cyc1,
(8) C1–8 alkyl substituted by one or more groups selected from —OR$^{11}$, —SR$^{11}$, —NR$^{12}$R$^{13}$, —COR$^{14}$, guanidino and Cyc1,
(9) C2–8 alkenyl substituted by one or more groups selected from —OR$^{11}$, —SR$^{11}$, —NR$^{12}$R$^{13}$, —COR$^{14}$, guanidino and Cyc1,
(10) C2–8 alkynyl,
(11) C1–8 alkyl substituted by one or more groups selected from C3–8 alkenyloxy, with the proviso that a group having a double bond at 1-position is excluded; and C3–8 alkynyloxy, with the proviso that a group having a triple bond at 1-position is excluded; or $R^3$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene;

in which Cyc1 is carbocyclic ring and carbocyclic ring may be substituted by one or more of (i) C1–8 alkyl, (ii) C1–8 alkoxy, (iii) nitro, (iv) guanidino, (v) amidino, (vi) halogen atoms, (vii) cyano (viii) hydroxy, (ix) benzyloxy, (x) —NR$^{101}$R$^{102}$, in which R$^{101}$ and R$^{102}$ each, independently, is hydrogen or C1–8 alkyl, (xi) —COOR$^{103}$, in which R$^{103}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR$^{104}$R$^{105}$, in which R$^{104}$ and R$^{105}$ each, independently, is hydrogen, C1–8 alkyl or phenyl;

$R^{11}$ is
(i) hydrogen,
(ii) C1–8 alkyl,
(iii) Cyc1,
(iv) —COR$^{18}$,
(v) C1–8 alkyl substituted by one or more groups selected from —OR$^{15}$, —SR$^{15}$, —NR$^{16}$R$^{17}$, —COR$^{18}$, guanidino and Cyc1;

$R^{15}$ is hydrogen, C1–8 alkyl, Cyc1 or C1–8 alkyl substituted by Cyc1 or C1–8 alkoxy;

$R^{16}$ is hydrogen or C1–8 alkyl;

$R^{17}$ is hydrogen, C1–8 alkyl or —COR$^{19}$, in which R$^{19}$ is C1–8 alkyl, Cyc1, C1–8 alkyl substituted by Cyc1;

$R^{18}$ is hydroxy, C1–8 alkyl, C1–8 alkoxy or —NR$^{20}$R$^{21}$, in which R$^{20}$ and R$^{21}$, each independently, is hydrogen, C1–8 alkyl, Cyc1 or C1–8 alkyl substituted by Cyc1;

$R^{12}$ is hydrogen, C1–8 alkyl, Cyc1 or C1–8 alkyl substituted by Cyc1;

$R^{13}$ is hydrogen, C1–8 alkyl, Cyc1, C1–8 alkyl substituted by Cyc1, or —COR$^{22}$, in which R$^{22}$ is C1–8 alkyl, Cyc1 or C1–8 alkyl substituted by Cyc1;

$R^{14}$ is hydroxy, C1–8 alkyl, C1–8 alkoxy, Cyc1, C1–8 alkyl substituted by Cyc1, or —NR$^{23}$R$^{24}$, in which R$^{23}$ and R$^{24}$, each independently, is (i) hydrogen, (ii) C1–8 alkyl, (iii) Cyc1 or (iv) C1–8 alkyl substituted by Cyc1 or hydroxy;

(1) when $R^8$ is
1) hydrogen,
2) C1–8 alkyl,
3) C1–8 alkoxycarbonyl,
4) C1–8 alkyl substituted by one or more groups selected from —OR$^{26}$, —SR$^{26}$, —NR$^{27}$R$^{28}$ and —COR$^{29}$, or
5) C1–8 alkoxycarbonyl substituted by Cyc2, $R^9$ is

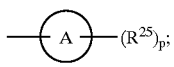

(2) when $R^8$ is

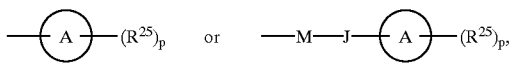

$R^9$ is
1) C1–8 alkyl,
2) C1–8 alkoxy,
3) C1–8 alkoxy substituted by Cyc2,
4) C1–8 alkyl substituted by one or more groups selected from —OR$^{26}$, —SR$^{26}$, —NR$^{27}$R$^{28}$, —COR$^{29}$ and Cyc2, or
5)

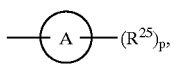

in which Cyc2 is carbocyclic ring and carbocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR$^{201}$R$^{202}$, in which R$^{201}$ and R$^{202}$ each, independently, is hydrogen or C1–8 alkyl, (xi) —COOR$^{203}$, in which R$^{203}$ is hydrogen or C1–8 alkyl (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR$^{204}$R$^{205}$, in which R$^{204}$ and R$^{205}$ each, independently, is hydrogen, C1–8 alkyl or phenyl;

$R^{26}$ is hydrogen, C1–8 alkyl, Cyc2 or C1–8 alkyl substituted by Cyc2;

$R^{27}$ is hydrogen, C1–8 alkyl, Cyc2 or C1–8 alkyl substituted by Cyc2;

$R^{28}$ is hydrogen, C1–8 alkyl, Cyc2, C1–8 alkyl substituted by Cyc2, or —COR$^{30}$, in which R$^{30}$ is C1–8 alkyl, Cyc2 or C1–8 alkyl substituted by Cyc2;

$R^{29}$ is hydroxy, C1–8 alkyl, Cyc2, C1–8 alkyl substituted by Cyc2, or —NR$^{31}$R$^{32}$, in which R$^{31}$ and R$^{32}$, each independently, is hydrogen, C1–8 alkyl, Cyc2 or C1–8 alkyl substituted by Cyc2;

is carbocyclic ring;

$R^{25}$ is —E—G;

E is
1) a single bond,
2) —CONR$^{33}$—,
3) —NR$^{33}$CO—,
4) —CO—O—,
5) —O—CO—,
6) —NR$^{33}$—CO—NR$^{34}$—,
7) —CO—CH$_2$—,
8) —CO—,
9) —O—CO—NR$^{33}$—,
10) —NR$^{33}$—CO—O—,
11) —O—CO—O—,
12) —CS—NR$^{33}$—,
13) —NR$^{33}$—CS—,
14) —CS—O—,
15) —O—CS—,
16) —NR$^{33}$—CS—NR$^{34}$—,
17) —CS—CH$_2$—,
18) —CS—,
19) —O—CS—NR$^{33}$—,
20) —NR$^{33}$—CS—O—,
21) —O—CS—O—,
22) —CH$_2$—CH$_2$—,
23) —HC=CH—,
24) —C≡C—,
25) —SO$_2$—NR$^{33}$—,
26) —NR$^{33}$—SO$_2$—,
27) —SO$_2$—CH$_2$— or
28) —CH$_2$—SO$_2$—;

$R^{33}$ and $R^{34}$, each independently, is hydrogen, C1–8 alkyl, Cyc3 or C1–8 alkyl substituted by Cyc3;

Cyc3 is carbocyclic ring and carbocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR$^{301}$R$^{302}$, in which R$^{301}$ and R$^{302}$ each, independently, is hydrogen or C1–8 alkyl, (xi) —COOR$^{303}$, in which R$^{303}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR$^{304}$R$^{305}$, in which R$^{304}$ and R$^{305}$ each, independently, is hydrogen, C1–8 alkyl or phenyl;

G is
1) hydrogen,
2) C1–8 alkyl,
3) Cyc4,
4) —OR$^{35}$,
5) —SR$^{35}$,
6) halogen atoms,
7) nitro,
8) cyano,
9) —NR$^{36}$R$^{37}$,
10) —COR$^{38}$,
11) C1–8 alkyl substituted by one or more groups selected from Cyc4, —OR$^{35}$, —SR$^{35}$, halogen atoms, —NR$^{36}$R$^{37}$ and —COR$^{38}$;

in which Cyc4 is carbocyclic ring and carbocyclic ring may be substituted by one or more of (i) C1–8 alkyl, (ii) C1–8 alkoxy, (iii) nitro, (iv) guanidino, (v) amidino, (vi) halogen atoms, (vii) cyano, (viii) hydroxy, (ix) benzyloxy, (x) —NR$^{401}$R$^{402}$, in which R$^{401}$ and R$^{402}$ each, independently, is hydrogen or C1–8 alkyl, (xi) —COOR$^{403}$, in which R$^{403}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or cyano, (xix) heterocyclic ring, (xx) keto, (xxi) C1–8 alkoxy substituted by —CONR$^{404}$R$^{405}$, in which R$^{404}$ and R$^{405}$ each, independently, is hydrogen, C1–8 alkyl or phenyl;

R$^{35}$ is hydrogen, C1–8 alkyl, C1–8 alkoxy, Cyc4 or C1–8 alkyl substituted by Cyc4;

R$^{36}$ is hydrogen, C1–8 alkyl, Cyc4, C1–8 alkyl substituted by Cyc4;

R$^{37}$ is hydrogen, C1–8 alkyl, Cyc4, C1–8 alkyl substituted by Cyc4, or —COR$^{39}$, in which R$^{39}$ is C1–8 alkyl, Cyc4 or C1–8 alkyl substituted by Cyc4;

R$^{38}$ is hydroxy, C1–8 alkyl, Cyc4, C1–8 alkyl substituted by Cyc4, or —NR$^{40}$R$^{41}$, in which R$^{40}$ and R$^{41}$, each independently, is hydrogen, C1–8 alkyl, Cyc4 or C1–8 alkyl substituted by Cyc4; or —E—G taken together, is C1–4 alkylidene;

p is 1–5;

M is C1–8 alkylene;

J is a single bond, an oxygen atom, a sulfur atom or —NR$^{42}$—, in which R$^{42}$ is hydrogen or C1–8 alkyl;

===== is a single bond, or a double bond which prepared by two hydrogens are released, in the case of two of R$^{2}$, R$^{3}$, R$^{4}$, R$^{5}$, R$^{6}$ and R$^{7}$ which do not bond to a same carbon atom but bond to a neighboring carbon, are hydrogens; with the proviso that ===== is not a double bond, when R$^{3}$ and R$^{4}$, taken together is C1–8 alkylene, R$^{5}$ and R$^{6}$, taken together is C1–8 alkylene, R$^{3}$ and R$^{6}$, taken together is C1–8 alkylene;

with the proviso that (1) at least one of R$^{2}$, R$^{3}$, R$^{4}$, R$^{5}$, R$^{6}$ and R$^{7}$ is C2–8 alkynyl, or C1–8 alkyl substituted by one or more groups selected from C3–8 alkenyloxy and C3–8 alkynyloxy, (2) when

is benzene, and E is a single bond, then G is not hydrogen;

(3) the following compound is excluded:
the compound wherein R$^{2}$ is 2-propynyl, and R$^{3}$, R$^{4}$, R$^{5}$, R$^{6}$ and R$^{7}$ each, independently, is the above groups (1) to (9) or R$^{3}$ and R$^{4}$, taken together is C1–8 alkylene, R$^{5}$ and R$^{6}$, taken together is C1–8 alkylene, R$^{3}$ and R$^{6}$, taken together is C1–8 alkylene, R$^{4}$ and R$^{5}$, taken together is C2–8 alkylene, or R$^{6}$ and R$^{7}$, taken together is C2–8 alkylene; non-toxic acid thereof.

2. The compound according to claim 1, wherein R$^{2}$, R$^{3}$, R$^{4}$, R$^{5}$, R$^{6}$ and R$^{7}$ are the same as defined in claim 1 and at least one of R$^{2}$, R$^{3}$, R$^{4}$, R$^{5}$, R$^{6}$ and R$^{7}$ is C1–8 alkyl substituted by one or more groups selected from C3–8 alkenyloxy and C3–8 alkynyloxy.

3. The compound according to claim 1, wherein R$^{2}$, R$^{3}$, R$^{4}$, R$^{5}$, R$^{6}$ and R$^{7}$ each, independently, is (1) hydrogen, (2) C1–8 alkyl, (3) C2–8 alkenyl, (4) —OR$^{11}$, (5) —SR$^{11}$, (6) —NR$^{12}$R$^{13}$, (7) Cyc1, (8) C1–8 alkyl substituted by one or more groups selected from —OR$^{11}$, —SR$^{11}$, —NR$^{12}$R$^{13}$, —COR$^{14}$, guanidino and Cyc1, (9) C2–8 alkenyl substituted by one or more groups selected from —OR$^{11}$, —SR$^{11}$, —NR$^{12}$R$^{13}$, —COR$^{14}$, guanidino and Cyc1, (10) C2–8 alkynyl, or R$^{3}$ and R$^{4}$, taken together is C1–8 alkylene, R$^{5}$ and R$^{6}$, taken together is C1–8 alkylene, R$^{3}$ and R$^{6}$, taken together is C1–8 alkylene, R$^{2}$ and R$^{3}$, taken together is C2–8 alkylene, R$^{4}$ and R$^{5}$, taken together is C2–8 alkylene, or R$^{6}$ and R$^{7}$, taken together is C2–8 alkylene, and at least one of R$^{2}$, R$^{3}$, R$^{4}$, R$^{5}$, R$^{6}$ and R$^{7}$ is C2–8 alkynyl.

4. A compound according to claim 2, which is selected from
(1) 5-ethoxymethoxy-2(R)-(2-propynyloxymethyl)-4(S)-[N-(4-nitrophenylcarbonyl)amino]pentanoic acid,
(2) 5-ethoxymethoxy-2(R)-(2-propenyloxymethyl)-4(S)-[N-(4-nitrophenylcarbonyl)amino]pentanoic acid,
(3) 5-ethoxymethoxy-2(R)-(2-propynyloxymethyl)-4(S)-[N-(4-chlorophenylcarbonyl)amino]pentanoic acid,
(4) N-hydroxy-5-ethoxymethoxy-2(R)-(2-propynyloxymethyl)-4(S)-[N-(4-nitrophenylcarbonyl)amino]pentanamide,
(5) N-hydroxy-5-ethoxymethoxy-2(R)-(2-propenyloxymethyl)-4(S)-[N-(4-nitrophenylcarbonyl)amino]pentanamide,
(6) N-hydroxy-5-ethoxymethoxy-2(R)-(2-propynyloxymethyl)-4(S)-[N-(4-chlorophenylcarbonyl)amino]pentanamide, or methyl ester, t-butyl ester, benzyl ester, allyl ester, and non-toxic salts thereof.

5. A matrix metalloproteinase inhibitor composition comprising the compound of the formula (I) according to claim 1, as active ingredient.

6. A pharmaceutical composition for treatment of rheumatoid diseases, arthrosteitis, osteoarthritis, unusual bone resorption, osteoporosis, periodontitis, interstitial nephritis, arteriosclerosis, pulmonary emphysema, cirrhosis, cornea injury, cornea ulcer, metastasis, invasion or growth of tumor cells, autoimmune disease, disease caused by vascular emigration or infiltration of leukocytes, arterialization, multiple sclerosis, aorta aneurysm, endometriosis, restenosis after PTCA, unstable angina, acute myocardial infarction, or transient ischemic attack, which comprises the compound of the formula (I) according to claim 1 as active ingredient and a pharmaceutically acceptable carrier.

7. A compound which is selected from
(1) 5-ethoxymethoxy-4(S)-[N-(4-iodophenylcarbonyl)amino]pentanoic acid,
(2) 5-ethoxymethoxy-4(S)-[N-(4-cyanophenylcarbonyl)amino]-2(R)-methoxymethylpentanoic acid,
(3) 2(R)-ethoxymethyl-5-ethoxymethoxy-4(S)-[N-(4-nitrophenylcarbonyl)amino]pentanoic acid,
(4) 5-ethoxymethoxy-2(S)-(3-thienylmethyl)-4(S)-[N-(4-nitrophenylcarbonyl)amino]pentanoic acid,
(5) 5-ethoxymethoxy-2(S)-(3-furylmethyl)-4(S)-[N-(4-nitrophenylcarbonyl)amino]pentanoic acid,
(6) 2(S)-benzyl-5-pivaroyloxy-4(S)-[N-(4-nitrophenylcarbonyl)amino]pentanoic acid,
(7) 5-acetyloxy-2(S)-benzyl-4(S)-[N-(4-nitrophenylcarbonyl)amino]pentanoic acid,
(8) 5-ethoxymethoxy-2(R)-methoxymethyl-4(S)-[N-(4-phenoxy-phenylcarbonyl)amino]pentanoic acid,
(10) 5-ethoxymethoxy-4(S)-[N-(4-cyanophenylcarbonyl)amino]-2(R)-ethoxymethylpentanoic acid,
(11) 5-ethoxymethoxy-2(S)-methoxymethyl-4(R)-[N-(4-nitrophenylcarbonyl)amino]pentanoic acid,

(12) 5-ethoxymethoxy-2(S)-methoxymethyl-4(R)-[N-(4-chlorophenylcarbonyl)amino]pentanoic acid,

(13) 5-ethoxymethoxy-2(S)-methoxymethyl-4(R)-[N-(4-bromophenylcarbonyl)amino]pentanoic acid,

(14) 5-ethoxymethoxy-2(S)-methoxymethyl-4(R)-[N-(4-cyanophenylcarbonyl)amino]pentanoic acid,

(15) 5-ethoxymethoxy-2(S)-benzyl-4(S)-[N-(4-chlorocyclohexylcarbonyl)amino]pentanoic acid,

(16) 5-ethoxymethoxy-4(S)-[N-(4-nitrophenylcarbonyl)amino]pentanoic acid,

(17) 5-methoxyethoxymethoxy-2(S)-methyl-4(S)-[N-methyl-N-(4-nitrophenylcarbonyl)amino]pentanoic acid,

(18) trans-2-[(4-nitrophenylcarbonyl)aminomethyl]cyclohexanoic acid,

(19) trans-2-[(4-(3-methoxy-1-propynyl)phenylcarbonyl)aminomethyl]cyclohexanoic acid,

(20) trans-2-[(4-nitrophenylcarbonyl)amino]cyclohexanoic acid,

(21) N-hydroxy-5-ethoxymethoxy-2(R)-methoxymethyl-4(S)-[N-(4-cyanophenylcarbonyl)amino]pentanamide,

(22) N-hydroxy-2(R)-ethoxymethyl-5-ethoxymethoxy-4(S)-[N-(4-nitrophenylcarbonyl)amino]pentanamide,

(23) N-hydroxy-5-ethoxymethoxy-2(S)-(3-thienylmethyl)-4(S)-[N-(4-nitrophenylcarbonyl)amino]pentanamide,

(24) N-hydroxy-5-ethoxymethoxy-2(S)-(3-furylmethyl)-4(S)-[N-(4-nitrophenylcarbonyl)amino]pentanamide,

(25) N-hydroxy-2(S)-benzyl-5-pivaroyloxy-4(S)-[N-(4-nitrophenylcarbonyl)amino]pentanamide,

(26) N-hydroxy-5-acetyloxy-2(S)-benzyl-4(S)-[N-(4-nitrophenylcarbonyl)amino]pentanamide,

(27) N-hydroxy-5-ethoxymethoxy-2(R)-methoxymethyl-4(S)-[N-(4-phenoxyphenylcarbonyl)amino]pentanamide,

(29) N-hydroxy-5-ethoxymethoxy-2(R)-ethoxymethyl-4(S)-[N-(4-cyanophenylcarbonyl)amino]pentanamide,

(30) N-hydroxy-5-ethoxymethoxy-2(S)-methoxymethyl-4(R)-[N-(4-nitrophenylcarbonyl)amino]pentanamide,

(31) N-hydroxy-5-ethoxymethoxy-2(S)-methoxymethyl-4(R)-[N-(4-chlorophenylcarbonyl)amino]pentanamide,

(32) N-hydroxy-5-ethoxymethoxy-2(S)-methoxymethyl-4(R)-[N-(4-bromophenylcarbonyl)amino]pentanamide,

(33) N-hydroxy-5-ethoxymethoxy-2(S)-methoxymethyl-4(R)-[N-(4-cyanophenylcarbonyl)amino]pentanamide,

(34) N-hydroxy-5-ethoxymethoxy-2(S)-benzyl-4(S)-[N-(4-chlorocyclohexylcarbonyl)amino]pentanamide,

(35) N-hydroxy-5-ethoxymethoxy-4(S)-[N-(4-nitrophenylcarbonyl)amino]pentanamide,

(36) N-hydroxy-2(S)-methyl-5-methoxyethoxymethoxy-4(S)-[N-methyl-N-(4-nitrophenylcarbonyl)amino]pentanamide,

(37) N-hydroxy-5-hydroxy-2(R)-methoxymethyl-4(S)-[N-(4-nitrophenylcarbonyl)amino]pentanamide,

(38) N-hydroxy-5-hydroxy-2(R)-methoxymethyl-4(S)-[N-(4-chlorophenylcarbonyl)amino]pentanamide,

(39) N-hydroxy-2(S)-(2-benzothiophen-3-yl)methyl)-5-hydroxy-4(S)-[N-methyl-N-(4-nitrophenylcarbonyl)amino]pentanamide,

(40) N-hydroxy-2(S)-allyl-5-hydroxy-4(S)-[N-methyl-N-(4-nitrophenylcarbonyl)amino]pentanamide,

(41) N-hydroxy-2(S)-(3-phenylpropyl)-5-hydroxy-4(S)-[N-methyl-N-(4-bromophenylcarbonyl)amino]pentanamide,

(42) N-hydroxy-2(S)-(3-phenylpropyl)-5-hydroxy-4(S)-[N-methyl-N-(4-nitrophenylcarbonyl)amino]pentanamide,

(45) trans-1-(N-hydroxyaminocarbonyl)-2-[(4-nitrophenylcarbonyl)aminomethyl]cyclohexane,

(46) trans-1-(N-hydroxyaminocarbonyl)-2-[(4-(3-methoxy-1-propynyl)phenylcarbonyl)aminomethyl]cyclohexane,

(47) trans-1-(N-hydroxyaminocarbonylmethyl)-2-[(4-nitrophenylcarbonyl)amino]cyclohexane,

(48) N-hydroxy-2(S)-(2-propynyl)-5-hydroxy-4(S)-[N-methyl-N-(4-nitrophenylcarbonyl)amino]pentanamide,

(49) N-hydroxy-2(S)-(2-propynyl)-5-hydroxy-4(S)-[N-methyl-N-(4-bromophenylcarbonyl)amino]pentanamide,

(50) N-hydroxy-5-hydroxy-2(S)-(2-propynyl)-4(S)-[N-methyl-N-(4-chlorophenylcarbonyl)amino]pentanamide, and

(51) N-hydroxy-5-ethoxymethoxy-4(S)-[N-(4-cyanophenylcarbonyl)amino]-2(S)-(2-propynyl)pentanamide, or methyl ester, t-butyl ester, benzyl ester, allyl ester, and non-toxic salts thereof.

8. A matrix metalloproteinase inhibitor composition comprising the compound according to claim 7, as active ingredient.

9. A pharmaceutical composition for treatment of rheumatoid diseases, arthrosteitis, osteoarthritis, unusual bone resorption, osteoporosis, periodontitis, interstitial nephritis, arteriosclerosis, pulmonary emphysema, cirrhosis, cornea injury, cornea ulcer, metastasis, invasion or growth of tumor cells, autoimmune disease, disease caused by vascular emigration or infiltration of leukocytes, arterialization, multiple sclerosis, aorta aneurysm, endometriosis, restenosis after PTCA, unstable angina, acute myocardial infarction, or transient ischemic attack, which comprises the compound according to claim 7 as active ingredient and a pharmaceutically acceptable carrier.

\* \* \* \* \*